United States Patent
Tao et al.

(10) Patent No.: US 9,345,699 B2
(45) Date of Patent: May 24, 2016

(54) ISOQUINOLINE, QUINOLINE, AND QUINAZOLINE DERIVATIVES AS INHIBITORS OF HEDGEHOG SIGNALING

(75) Inventors: Chunlin Tao, Los Angeles, CA (US); Xiaowen Sun, Shanghai (CN); Hongna Han, Irvine, CA (US); Lukasz Koroniak, Poznan (PL); Neil Desai, Los Angeles, CA (US)

(73) Assignee: NantBioScience, Inc., Culver City, CA (US)

( * ) Notice: Subject to any disclaimer, the term of this patent is extended or adjusted under 35 U.S.C. 154(b) by 309 days.

(21) Appl. No.: 13/376,813

(22) PCT Filed: Jun. 9, 2010

(86) PCT No.: PCT/US2010/037986
§ 371 (c)(1),
(2), (4) Date: Jul. 3, 2012

(87) PCT Pub. No.: WO2010/144586
PCT Pub. Date: Dec. 16, 2010

(65) Prior Publication Data
US 2012/0270858 A1    Oct. 25, 2012

Related U.S. Application Data

(60) Provisional application No. 61/185,412, filed on Jun. 9, 2009.

(51) Int. Cl.
| | | |
|---|---|---|
| C07D 217/16 | (2006.01) | |
| A61K 31/472 | (2006.01) | |
| A61K 31/47 | (2006.01) | |
| A61K 31/517 | (2006.01) | |
| C07D 239/74 | (2006.01) | |
| C07D 401/12 | (2006.01) | |
| C07D 401/14 | (2006.01) | |
| C07D 403/12 | (2006.01) | |
| C07D 407/12 | (2006.01) | |
| C07D 409/12 | (2006.01) | |
| C07D 413/12 | (2006.01) | |
| C07D 413/14 | (2006.01) | |
| C07D 417/12 | (2006.01) | |
| C07D 417/14 | (2006.01) | |
| C07D 471/04 | (2006.01) | |

(52) U.S. Cl.
CPC ............... *A61K 31/47* (2013.01); *A61K 31/517* (2013.01); *C07D 217/16* (2013.01); *C07D 239/74* (2013.01); *C07D 401/12* (2013.01); *C07D 401/14* (2013.01); *C07D 403/12* (2013.01); *C07D 407/12* (2013.01); *C07D 409/12* (2013.01); *C07D 413/12* (2013.01); *C07D 413/14* (2013.01); *C07D 417/12* (2013.01); *C07D 417/14* (2013.01); *C07D 471/04* (2013.01)

(58) Field of Classification Search
CPC ............................ C07D 217/16; A61K 31/472
USPC ..................................... 546/166, 144; 514/307
See application file for complete search history.

(56) References Cited

U.S. PATENT DOCUMENTS

| | | | |
|---|---|---|---|
| 5,451,596 A | 9/1995 | Ullrich et al. | |
| 5,854,264 A | 12/1998 | Anthony et al. | |
| 5,916,596 A | 6/1999 | Desai et al. | |
| 6,429,213 B1 | 8/2002 | Xue et al. | |
| 6,506,405 B1 | 1/2003 | Desai et al. | |
| 6,537,579 B1 | 3/2003 | Desai et al. | |
| 6,635,655 B1 | 10/2003 | Jayyosi et al. | |
| 6,653,332 B2 | 11/2003 | Jaen et al. | |
| 6,858,626 B2 | 2/2005 | Xue et al. | |
| 6,890,915 B2 | 5/2005 | Sheppeck et al. | |
| 6,906,053 B2 | 6/2005 | Sheppeck | |
| 6,933,272 B1 | 8/2005 | Helmerhorst et al. | |
| 6,960,685 B2 | 11/2005 | Watkins et al. | |
| 7,005,440 B1 | 2/2006 | Jayyosi et al. | |
| 7,041,693 B2 | 5/2006 | Sheppeck | |
| 7,067,539 B2 | 6/2006 | Kozlowski et al. | |
| 7,151,118 B2 | 12/2006 | Angell et al. | |
| 7,157,487 B2 | 1/2007 | Nakayama et al. | |
| 7,211,671 B2 | 5/2007 | Sheppeck et al. | |
| 7,294,624 B2 | 11/2007 | Duan et al. | |
| 7,309,800 B2 | 12/2007 | Angell et al. | |
| 7,312,226 B2 | 12/2007 | Hurley et al. | |
| 7,326,712 B2 | 2/2008 | Hurley et al. | |

(Continued)

FOREIGN PATENT DOCUMENTS

| | | |
|---|---|---|
| AU | 2006-275160 A1 | 2/2007 |
| JP | 2005-529876 A | 10/2005 |
| JP | 2007-535569 A | 12/2007 |
| JP | 2007-537275 A | 12/2007 |
| JP | 2008-511675 A | 4/2008 |
| JP | 2008-519044 A | 6/2008 |

(Continued)

OTHER PUBLICATIONS

Aldrich, Catalalouge Handbook of Fine Chemicals Australian Ed., CAS RN 7568-93-6 STN (1998-1999).

(Continued)

*Primary Examiner* — Yong Chu
*Assistant Examiner* — Sonya Wright
(74) *Attorney, Agent, or Firm* — Leydig, Voit & Mayer, Ltd.

(57) ABSTRACT

The invention provides isoquinoline, quinoline, and quinazoline derivatives to treat a variety of disorders, diseases and pathologic conditions, and more specifically to the use of isoquinoline, quinoline, and quinazoline derivatives to inhibit the hedgehog signaling pathway and to the use of those compounds to the treatment of hyperproliferative diseases and pathologic angiogenesis.

24 Claims, No Drawings

(56) References Cited

U.S. PATENT DOCUMENTS

| | | | |
|---|---|---|---|
| 7,326,713 | B2 | 2/2008 | Hurley et al. |
| 7,335,662 | B2 | 2/2008 | Hurley et al. |
| 7,345,178 | B2 | 3/2008 | Nunes et al. |
| 7,396,843 | B2 | 7/2008 | Angell et al. |
| RE40,558 | E | 10/2008 | Jayyosi et al. |
| 7,482,372 | B2 | 1/2009 | Sheppeck et al. |
| 7,507,767 | B2 | 3/2009 | Kozlowski et al. |
| 7,569,724 | B2 | 8/2009 | Watkins et al. |
| 7,585,846 | B2 | 9/2009 | Sheu et al. |
| 7,595,317 | B2 | 9/2009 | Duan et al. |
| 2003/0199516 | A1 | 10/2003 | Moser et al. |
| 2003/0220373 | A1 | 11/2003 | Jaye et al. |
| 2004/0087798 | A1 | 5/2004 | Yamada |
| 2004/0259918 | A1 | 12/2004 | Jaen et al. |
| 2005/0065195 | A1 | 3/2005 | Angell et al. |
| 2005/0222087 | A1 | 10/2005 | Beachy et al. |
| 2005/0260126 | A1 | 11/2005 | Kudo et al. |
| 2006/0004010 | A1 | 1/2006 | Habashita et al. |
| 2006/0009528 | A1 | 1/2006 | Kozlowski |
| 2006/0035897 | A1 | 2/2006 | Caravatti et al. |
| 2006/0035928 | A1 | 2/2006 | Jaen et al. |
| 2006/0122267 | A1 | 6/2006 | Brookes et al. |
| 2006/0160748 | A1 | 7/2006 | Sheu et al. |
| 2006/0293336 | A1 | 12/2006 | Sutton et al. |
| 2007/0049559 | A1 | 3/2007 | Pfeffer et al. |
| 2007/0185152 | A1 | 8/2007 | Yamashita et al. |
| 2007/0185156 | A1* | 8/2007 | Napier et al. ............... 514/304 |
| 2007/0249665 | A1* | 10/2007 | Lee ............................ 514/307 |
| 2007/0287707 | A1 | 12/2007 | Arrington et al. |
| 2007/0299067 | A1 | 12/2007 | Liu et al. |
| 2008/0051414 | A1 | 2/2008 | Hurley et al. |
| 2008/0096883 | A1 | 4/2008 | Caravatti et al. |
| 2008/0182847 | A1 | 7/2008 | Augeri et al. |
| 2009/0036419 | A1 | 2/2009 | Chen et al. |
| 2009/0099165 | A1 | 4/2009 | Hurley et al. |
| 2009/0099170 | A1 | 4/2009 | Nunes et al. |
| 2009/0099175 | A1 | 4/2009 | Arrington et al. |
| 2009/0137594 | A1 | 5/2009 | Frank et al. |
| 2009/0143399 | A1 | 6/2009 | Hurley et al. |
| 2009/0163476 | A1 | 6/2009 | Milburn et al. |

FOREIGN PATENT DOCUMENTS

| | | |
|---|---|---|
| JP | 2009-517442 A | 4/2009 |
| JP | 2012-500853 A | 1/2012 |
| WO | WO 99/20275 A1 | 4/1999 |
| WO | WO 00/64876 A1 | 11/2000 |
| WO | WO 00/64888 A1 | 11/2000 |
| WO | WO 01/25220 A1 | 4/2001 |
| WO | WO 01/66098 A2 | 9/2001 |
| WO | WO 01/82916 A2 | 11/2001 |
| WO | WO 02/062750 A1 | 8/2002 |
| WO | WO 2005/037285 A1 | 4/2005 |
| WO | WO 2005/113513 A2 | 12/2005 |
| WO | WO 2005/118580 A2 | 12/2005 |
| WO | WO-2005113513 * | 12/2005 |
| WO | WO 2006/028958 A2 | 3/2006 |
| WO | WO 2006/050506 A1 | 5/2006 |
| WO | WO 2006/078283 A2 | 7/2006 |
| WO | WO 2006/094236 A1 | 9/2006 |
| WO | WO 2007/014607 A1 | 2/2007 |
| WO | WO 2007/056016 A2 | 3/2007 |
| WO | WO 2007/063071 A1 | 6/2007 |
| WO | WO 2008/012326 A1 | 1/2008 |
| WO | WO 2008/026704 A1 | 3/2008 |
| WO | WO 2008/112913 A1 | 9/2008 |
| WO | WO 2008/116920 A2 | 10/2008 |
| WO | WO 2009/006389 A2 | 1/2009 |
| WO | WO 2009/030952 A2 | 3/2009 |

OTHER PUBLICATIONS

CAS RN 448936-87-6 STN Entry Date Sep. 10, 2002.
CAS RN 448936-97-8 STN Entry Date Sep. 10, 2002.
CAS RN 448936-79-6 STN Entry Date Sep. 10, 2002.
CAS RN 448936-82-1 STN Entry Date Sep. 10, 2002.
CAS RN 448936-75-2 STN Entry Date Sep. 10, 2002.
CAS RN 448936-92-3 STN Entry Date Sep. 10, 2002.
CAS RN 448936-77-4 STN Entry Date Sep. 10, 2002.
CAS RN 448936-90-1 STN Entry Date Sep. 10, 2002.
CAS RN 448936-91-2 STN Entry Date Sep. 10, 2002.
CAS RN 448936-73-0 STN Entry Date Sep. 10, 2002.
CAS RN 448936-84-3 STN Entry Date Sep. 10, 2002.
CAS RN 448936-80-9 STN Entry Date Sep. 10, 2002.
Search Report AU Patent Application No. 2010258800 (Sep. 20, 2012).
Altaba et al., *Development*, 126, 3205-3216 (1999).
Argenti et al., *J. Neuroscience*, 25(36), 8338-8346 (Sep. 7, 2005).
Balordi et al., *J. Neuroscience*, 27(52), 14248-14259 (Dec. 26, 2007).
Belloni et al., *Nat. Genet.*, 14, 353-356 (Nov. 1996).
Berman et al., *Science*, 297, 1559-1561 (Aug. 30, 2002).
Bhatia et al., *J. Biol. Chem.*, 281(28), 19320-19326 (Jul. 14, 2006).
Bhattacharya et al., *Clin. Cancer Res.*, 14(23), 7659-7666 (Dec. 1, 2008).
Blake et al., *J. Biol. Chem.*, 273(22), 14037-14045 (May 29, 1998).
Chapoulaud et al., *Tetrahedron*, 56, 5499-5507 (2000).
Chi et al., *Cancer Lett.*, 244, 53-60 (2006).
Clayden et al., *Organic Chemistry*, 276-296, Oxford Univ. Press (2001).
Clement et al., *Curr. Biol.*, 17, 165-172 (Jan. 23, 2007).
Dahmane et al., *Development*, 128, 5201-5212 (2001).
Dai et al., *J. Biol. Chem.*, 274(12), 8143-8152 (Mar. 19, 1999).
Dimarcotullio et al., *PNAS*, 101(29), 10833-10838 (Jul. 20, 2004).
Echelard et al., *Cell*, 75, 1417-1430 (Dec. 31, 1993).
Fan et al., *Endocrinology*, 145(8), 3961-3970 (2004).
Feng et al., *Clin. Cancer Res.*, 13(5), 1389-1398 (2007).
Funabashi et al., *J. Am. Chem. Soc.*, 123, 10784-10785 (2001).
Hahn et al., *Nat. Med.*, 4(5), 619-622 (May 1998).
Hanson et al., *J. Med. Chem.*, 50, 3928-3936 (2007).
Hatta et al., *J. Cutan. Pathol.*, 32, 131-136 (2005).
Hennequin et al., *J. Med. Chem.*, 42, 5369-5389 (1999).
Horning, E.C. (Ed. In Chief), *Organic Syntheses*, Collective vol. 3, pp. 788-790, John Wiley & Sons, Inc. (1955).
Hudlický, Miloš, Reductions in Organic Chemistry, $2^{nd}$ ed., ACS Monograph 188, 19-30 (1996).
Hui et al., *Nat. Genet.*, 3, 241-246 (Mar. 1993).
Hunter, Tony, *Cell*, 88, 333-346 (Feb. 7, 1997).
Hynes et al., *Neuron*, 19, 15-26 (Jul. 1997).
Ingham et al., *Genes & Dev.*, 15, 3059-3087 (2001).
Ji et al., *J. Biol. Chem.*, 282(19), 14048-14055 (May 11, 2007).
Johnson et al., *Science*, 272, 1668-1671 (Jun. 14, 1996).
Karhadkar et al., *Nature*, 431, 707-712 (Oct. 7, 2004).
Karlstrom et al., *Development*, 130, 1549-1564 (2003).
Kinzler et al., *Science*, 236, 70-73 (Apr. 3, 1987).
Kolterud et al., *Drug Disc. Today: Ther. Strat.*, 4(4), 229-235 (2007).
Lai et al., *Nature Neurosci.*, 6(1), 21-27 (Jan. 2003).
Lavine et al., *J. Clin. Invest.*, 118(7), 2404-2414 (Jul. 2008).
Lee et al., *Science*, 266, 1528-1537 (Dec. 2, 1994).
Machold et al., *Neuron*, 39, 937-950 (Sep. 11, 2003).
Manning et al., *Organic Lett.*, 4(7), 1075-1078 (2002).
Mao et al., *J. Biol. Chem.*, 277(38), 35156-35161 (2002).
Mcgarvey et al., *Oncogene*, 17, 1167-1172 (1998).
Mo et al., *Development*, 124, 113-123 (1997).
Mongin et al., *J. Org. Chem.*, 69, 6766-6771 (2004).
Mori et al., *Oncology*, 70, 378-389 (2006).
Morrison Robert T. and Robert N. Boyd, Organic Chemistry, $6^{th}$ ed., 666-762, Englewood Cliffs, N.J., Prentice Hall (1992).
Morton et al., *PNAS*, 104(12), 5103-5108 (Mar. 20, 2007).
Nilsson et al., *PNAS*, 97(7), 3438-3443 (Mar. 28, 2000).
Nüsslein-Volhard et al., *Nature*, 287, 795-801 (Oct. 30, 1980).
Park et al., *Development*, 127, 1593-1605 (2000).
Pepinsky et al., *J. Biol. Chem.*, 273(22), 14037-14045 (May 29, 1998).
Pomeroy et al., *Nature*, 415, 436-442 (Jan. 24, 2002).
Porter et al., *Science*, 274, 255-259 (Oct. 11, 1996).
Qualtrough et al., *Int. J. Cancer*, 110, 831-837 (2004).
Rabjohn, Norman (Ed. in Chief), *Organic Syntheses*, Collective vol. 4, pp. 108-110, John Wiley & Sons, Inc. (1963).

(56) References Cited

OTHER PUBLICATIONS

Rabjohn, Norman (Ed. in Chief), *Organic Syntheses*, Collective vol. 4, pp. 984-986, John Wiley & Sons, Inc. (1963).
Riobo et al., *Cancer Res.*, 66(2), 839-845 (Jan. 15, 2006).
Romer et al., *Cancer Cell*, 6, 229-240 (Sep. 2004).
Sanchez et al., *Mech. Dev.*, 122, 223-230 (2005).
Sheng et al., *Mol. Cancer*, 3, 29 (2004).
Shin et al., *Proc. Nat. Acad. Sci. USA*, 96, 2880-2884 (Mar. 1999).
Stone et al., *Nature*, 384, 129-134 (Nov. 14, 1996).
Tabin et al., *Science*, 321, 350-352 (Jul. 18, 2008).
Taschner, Michael J., "Triphenylphosphine-Carbon Tetrachloride" *Encyclopedia of Reagents for Organic Syntheyis* (Apr. 15, 2001).
Thayer et al., *Nature*, 425, 851-856 (Oct. 23, 2003).
Tostar et al., *J. Pathol.*, 208, 17-25 (2006).
Varjosalo et al., *Cell*, 133, 537-548 (May 2, 2008).
Varjosalo et al., *Genes & Dev.*, 22, 2454-2472 (2008).
Venkataraman et al., *Tetrahedron Lett.*, 32, 3037-3040 (1979).
Watkins et al., *Nature*, 422, 313-317 (Mar. 20, 2003).
Whitesell et al., *Curr. Cancer Drug Targets*, 3, 349-358 (2003).
Xie et al., *Nature*, 391, 90-92 (Jan. 1, 1998).
Yoon et al., *J. Biol. Chem.*, 277(7), 5548-5555 (Feb. 15, 2002).
Yoon et al., *Int. J. Cancer*, 124, 109-119 (2009).
Zhang et al., *Nature*, 410, 599-604 (Mar. 29, 2001).
Nishida et al., *Chem. Lett.*, 34 (10), 1378-1379 (2005).
European Patent Application 10 78 6788 Search Report (Nov. 7, 2012).
Australian Patent Office, Office Action in AU Pat. App. No. 2010258800, 4 pp. (Feb. 19, 2013).
Canadian Intellectual Property Office, Office Action in CA Pat. App. No. 2765053, 3 pp. (Mar. 22, 2013).
Chinese Intellectual Property Office, Office Action in CN Pat. App. No. 201080032860.3, 14 pp. (May 13, 2013).
European Patent Office, Office Action in EP Pat. App. No. 10786788.9, 6 pp. (Aug. 23, 2013).
Korean Intellectual Property Office, Office Action in KR Pat. App. No. 10-2012-7000654, 16 pp. (Jul. 29, 2013).
Xie et al., *Organic Letters*, 6(1), 83-86 (2004).
Japanese Patent Application No. 515106/2012, Office Action (Jul. 29, 2014).

* cited by examiner

ISOQUINOLINE, QUINOLINE, AND QUINAZOLINE DERIVATIVES AS INHIBITORS OF HEDGEHOG SIGNALING

RELATED APPLICATIONS

This patent application claims the benefit of U.S. Provisional Patent Application No. 61/185,412, filed Jun. 9, 2009, which is incorporated by reference.

FIELD OF THE INVENTION

The present invention relates generally to the use of isoquinoline, quinoline, and quinazoline derivatives to treat a variety of disorders, diseases and pathologic conditions, and more specifically to the use of isoquinoline, quinoline, and quinazoline derivatives to inhibit the hedgehog signaling pathway and to the use of those compounds to the treatment of hyperproliferative diseases and angiogenesis mediated diseases.

BACKGROUND OF THE INVENTION

The hedgehog (Hh) gene was first identified during a search for embryonic lethal mutants of *Drosophila melanogaster*, which found that mutation of Hh resulted in altered segment patterning of the larva (Nusslein-Volhard, C.; Wieschaus, E. Nature 1980, 287, 795-801). Subsequently the gene was identified in many other invertebrates and vertebrates, including humans. Three mammalian counterparts of the Hh gene, termed Sonic hedgehog (Shh), Dessert hedgehog (Dhh), and cDNA libraries (Echelard, Y.; Epstein, D. J.; et al., Cell 1993, 75, 1417-1430). Hh undergoes multiple processing events, including autocatalytic cleavage of the C-terminal domain combined with addition of a cholesterol moiety at the cleavage site, and an N-terminal palmitoylation, to generate the active ligand (Lee, J. J.; Ekker, S. C.; et al., Science 1994, 266, 1528-1537; Porter, J. A.; Young, K. E.; et al., Science 1996, 274, 255-259; Pepinsky, R. B.; Zeng, C.; et al., J. Biol. Chem. 1998, 273, 14037-14045).

The receptor of secreted Hh protein is the multipass transmembrane protein Patched (Ptch). Of the two vertebrate homologues of Ptch (Ptch1 and Ptch2), the role of Ptch1 is better understood. In the absence of Hh ligand, Ptch inhibits the activity of the downstream effector Smoothened (Smo). The binding of Hh inactivates Ptch, resulting in activation of Smo (Stone, D. M.; Hynes, M.; et al., Nature 1996, 384, 129-134). In *Drosophila*, a complex of proteins comprising Fused (Fu), Suppressor of Fused (SuFu), and Costal-2 (Cos2) mediates signaling downstream of Smo and is aided by several kinases, such as protein kinase A (PKA), glycogen synthase kinase 3 (GSK3), and casein kinase 1 (CK1). Mammalian homologues of Fu and Cos2 have not yet been identified, suggesting that the signaling mechanisms differ in mammals and *Drosophila*. Several mammalian-specific kinases that is required for Shh signaling have been identified (Varjosalo, M.; Bjorklund, M.; et al., Cell 2008, 133, 537-548; Mao, J.; Maye, P.; et al., J. Biol. Chem. 2002, 277, 35156-35161; Riobo, N. A.; Haines, G. M.; et al., Cancer Res. 2006, 66, 839-845). These proteins modulate the function of Gli (Ci in *Drosophila*), the only transcription factor identified to date that operates directly downstream of Hh.

The first vertebrate Gli gene to be discovered was human Gli1, which was amplified about 50-fold in a malignant glioma (Kinzler, K. W.; Bigner, S. H.; et al., Science 1987, 236, 70-73). Vertebrates have three Gli proteins (Gli1, Gli2, and Gli3), all of which have five highly conserved tandem zinc fingers, a fairly conserved N-terminal domain, several potential PKA sites, and a number of additional small conserved regions in the C-terminal end. Despite these similarities, the functions of the Gli subtypes differ. Both Gli2 and Gli3 contain activation and repressor domains. Consequently, in the absence of upstream Hh signal, full-length Gli3 and, to a lesser extent, Gli2 are constitutively cleaved to generate a truncated repressor form (Dai, P.; Akimaru, H.; et al., J. Biol. Chem. 1999, 274, 8143-8152; Ruiz i Altaba, DeVelopment 1999, 126, 3205-3216; Shin, S. H.; Kogerman, P.; et al., Proc. Natl. Acad. Sci. U.S.A. 1999, 96, 2880-2884). Hh signaling inhibits this cleavage, resulting in full-length Gli2 and Gli3, which have activator function. Gli1, in contrast, does not undergo proteolytic cleavage and acts as a constitutive activator. The transcription of Gli1 gene is initiated by Hh and is also controlled by Gli3.27. Target genes of the Hh pathway other than Gli1 include Ptch, several Wnt and TGF superfamily proteins, cell cycle proteins such as cyclin D, and stem-cell marker genes such as NANOG and SOX2.30,31. Investigators are now attempting to comprehensively identify the Gli1-target genes (Yoon, J. W.; Kita, Y.; et al., J. Biol. Chem. 2002, 277, 5548-5555; Yoon, J. W.; Gilbertson, R.; Mt. J. Cancer 2008, 124, 109-119).

The Hh signaling pathway is crucial for proper embryonic development (Ingham, P. W.; McMahon, A. P. Genes Dev. 2001, 15, 3059-3087). It is also essential for restraining growth in the nervous system and other tissues and in maintenance of stem cells in adults (Machold, R.; Hayashi, S., et al., Neuron 2003, 39, 937-950; Lavine, K. J.; Kovacs, A.; et al., J. Clin. InVest. 2008, 118, 2404-2414. Balordi, F.; Fishell, G. et al., J. Neurosci. 2007, 27, 14248-14259). The expression and roles of Hh in vertebrate tissues/organs have been extensively described in the recent reviews (Varjosalo, M.; Taipale, J. Genes DeV. 2008, 22, 2454-2472).

Two of the functions of Hh in vertebrate embryonic development are both crucial and relatively well understood: neural tube differentiation and anteroposterior limb patterning. The predominant mechanism of Hh signaling in these functions is paracrine signaling, in which the Hh molecules act in a gradient fashion. For example, in vertebrate limb buds, exposure to different concentrations of Shh modulates patterning of the interdigital mesenchyme, which influences the proper growth of digits in a specific pattern (Tabin, C. J.; McMahon, A. P. Science 2008, 321, 350-352). In neural tube development, Shh produced by the floor plate causes dorsoventral patterning, the specification of ventral cell populations, and general cellular proliferation in the brain. 40 Holoprosencephaly, a disorder involving the development of forebrain and midface in which ventral cell types are lost, is caused in humans by mutations that lead to loss of Shh activity (Belloni, E.; Muenke, M.; et al., Nat. Genet. 1996, 14, 353-356).

Another important feature of Shh signaling is that the Gli subtypes have both unique and overlapping functions. While ectopic expression of Gli1 in the midbrain and hindbrain of transgenic mice results in expression of some ventral cell types, mice homozygous for a mutation in the region encoding the zinc finger domain of Gli1 develop normally (Hynes, M.; Stone, D. M.; et al., Neuron, 1997, 19, 15-26; Park, H. L.; Bai, C.; et al., Development 2000, 127, 1593-1605). However, Gli1/Gli2 double mutant mice have phenotypes with severe multiple defects, including variable loss of the ventral spinal cord, and smaller lungs; therefore, Gli2 plays a more important role in spinal cord and lung development than does Gli1. In contrast, Gli1/Gli3 double mutant mice did not have these phenotypes (Park, H. L.; Bai, C.; et al., DeVelopment 2000, 127, 1593-1605). Gli2 and Gli3 have both been implicated in skeletal development, with each subtype serving specific functional roles. Gli2 mutant mice exhibit severe skeletal abnormalities including cleft palate, tooth defects, absence of vertebral body and intervertebral discs, and shortened limb and sternum (Mo, R.; Freer, A. M.; et al., DeVelopment 1997, 124, 113-123). Gli3 appears to be the major mediator of Shh effect in the limbs, as Gli1/Gli2 double mutant mice had a normal digit number and pattern while Gli3 mutant mice showed polydactyly (Hui, C. C.; Joyner, A. L. Nat. Genet. 1993, 3, 241-246).

Genetic analyses of Gli mutants revealed that the requirement for Gli subtypes development is quite divergent even among vertebrates. In zebrafish, both detour (dtr) mutations (encoding loss-of-function alleles of Gli1) and you-too (yot) mutations (encoding C-terminally truncated Gli2) have defects in body axis formation and expression of Hh-target genes in the brain (Karlstrom, R. O.; Tyurina, O. V.; et al., DeVelopment 2003, 130, 1549-1564), suggesting divergent requirements for Gli1 and Gli2 in mouse and zebrafish.

In adults, the Hh pathway is essential for restraining growth in the nervous system and other tissues and in maintenance of stem cells. Zhang and Kalderon have shown that Hh acts specifically on stem cells in *Drosophila* ovaries and that these cells cannot proliferate in the absence of Hh (Zhang, Y.; Kalderon, D. Nature 2001, 410, 599-604). Other studies showed that Hh signaling in the postnatal telencephalon both promotes proliferation and maintains populations of neural progenitors, suggesting that Shh signaling in the mammalian telencephalon may participate in the maintenance of a neural stem cell niche. The role of Hh in proliferation of adult neural progenitor cells was confirmed by a study in which Shh was overexpressed and proliferation was inhibited by using a Smo antagonist (Lai, K.; Kaspar, B. K.; et al., Nat. Neurosci. 2003, 6, 21-27).

Hh genes have the ability to induce tissue proliferation. This function is important in embryogenesis and tissue maintenance, but inappropriate activation of the pathway can result in tumorigenesis (Hunter, T. Cell 1997, 88, 333-346). Tumors in about 25% of all cancer deaths are estimated to involve aberrant Hh pathway activation. Tumorigenesis or tumor growth can result from abnormal up-regulation of Hh ligand or from deregulation of the expression or function of downstream components by, for example, loss of Ptch, activating mutations of Smo (Xie, J.; Murone, M.; et al., Nature 1998, 391, 90-92), loss of SuFu, amplification or chromosomal translocation of Gli1 or Gli2 gene amplification or stabilization of Gli2 protein (Bhatia, N.; Thiyagarajan, S.; J. Biol. Chem. 2006, 281, 19320-19326).

The first Hh pathway gene found to be amplified in cancers was Gli1, which was expressed at high levels in human glioblastoma and derived cell lines. Subsequently, Gli1 was found to be consistently expressed in a variety of glial tumors, and Gli1 overexpression was shown to induce central-nerves system hyperproliferation (Dahmane, N.; Sanchez, P.; et al., Development 2001, 128, 5201-5212). Gli1 overexpression has also been observed in a panel of brain tumors ranging from low-grade to high-grade in a study that identified Gill expression as the only reliable marker of Hh pathway activity (Clement, V.; Sanchez, P.; Curr. Biol. 2007, 17, 165-172). Further, cell proliferation in primary cultures of many of these tumors was inhibited by Gli1 small-interfering RNA. Gli1 expression was correlated with tumor grade in PDGF-induced liomagenesis in mice. Hh signaling components other than Gli1 also contribute to tumorigenesis in specific subsets of glioblastomas. In PDGF induced tumors, expression level of Shh was correlated with the tumor grade. However, other studies found only a subset of gliomas to contain high levels of Shh.

Another cancer with defects in Hh pathway regulation is basal cell carcinoma (BCC). Human Ptch was first identified by virtue of its mutation in patients with Gorlin syndrome (GS), a genetic disease that gives rise to sporadic BCC (Johnson, R. L.; Rothman, A. L.; et al., Science 1996, 272, 1668-1671). The mutations of Ptch identified in BCC include deletions producing truncated proteins and insertion or nonsense mutations accompanied by loss of heterozygosity (LOH) or mutations in the other allele. These mutations inhibit the ability of Ptch to suppress Smo, resulting in constitutive Hh signaling. While Ptch1 abnormalities are detected in the majority of BCC patients, it is now clear that a subset of BCC is also driven by a mutation in Smo that decreases its sensitivity to inhibition by Ptch. In addition, overexpression of Gli1 protein causes BCC-like tumors in mice, establishing the importance of Gli1 transcription in BCC tumorigenesis (Nilsson, M.; Unden, A. B.; et al, Proc. Natl. Acad. Sci. U.S.A. 2000, 97, 3438-3443). The level of Gli1 transcript can be used to discriminate BCC from certain other skin tumors (Hatta, N.; Hirano, T.; et al., J. Cutaneous Pathol. 2005, 32, 131-136). However, blocking of Gli-based transcription has not yet been shown to arrest BCC growth.

Medulloblastoma, the most common malignant pediatric brain tumor, is linked with mutations in Ptch and Smo and mutations in other Hh pathway genes such as SuFu and Gli (Pomeroy, S. L.; Tamayo, P.; et al., Nature 2002, 415, 436442). Inactivation of the Ptch locus by deletion and mutation has been found in about 10% of sporadic medulloblastomas. Shh pathway involvement in these tumors was further confirmed by studies in which treatment of murine medulloblastomas with Smo inhibitors inhibited cell proliferation and reduced tumor growth in mice (Berman, D M.; Karhadkar, S. S.; et al., Science 2002, 297, 1559-1561; Sanchez, P.; Ruiz i Altaba, Mech. DeV. 2005, 122, 223-230; Romer, J. T.; Kimura, H. et al., Cancer Cell 2004, 6, 229-240). Taylor et al. identified SuFu as a tumorsuppressor gene whose mutation predisposes individuals to medulloblastoma. They found that a subset of children with medulloblastoma carry germline and somatic mutations in SuFu, accompanied by loss of heterozygosity of the wild-type allele. Several of these mutations encoded truncated SuFu proteins that are unable to export Gli protein from the nuclei. In addition, the tumor-suppressor REN has also been linked with medulloblastoma in which the allelic deletion and reduced expression of REN are frequently observed. It is suggested that it inhibits medulloblastoma growth by negatively regulating the Hh pathway (C.; Zazzeroni, F.; Gallo, R.; et al., Proc. Natl. Acad. Sci. U.S.A. 2004, 101, 10833-10838; Argenti, B.; Gallo, R.; et al., J. Neurosci. 2005, 25, 8338-8346).

Hh has also been shown to be an early and late mediator of pancreatic cancer tumorigenesis. Shh was not detected in normal adult human pancreata but was aberrantly expressed in 70% of pancreatic adenocarcinoma specimens (Thayer, S. P.; di Magliano, M. P.; et al., Nature 2003, 425, 851-856). Participation of Shh signaling has been indicated at multiple stages of pancreatic carcinogenesis and is accompanied by multiple oncogenic factors, including K-Ras, one of the most frequently mutated genes in pancreatic cancer (Morton, J. P.; Mongeau, M. E.; et al., Proc. Natl. Acad. Sci. U.S.A. 2007, 104, 5103-5108; Ji, Z.; Mei, F. C.; et al., J. Biol. Chem. 2007, 282, 14048-14055). Activated Hh signaling was detected in cell lines established from primary and metastatic pancreatic adenocarcinomas, and the Smo inhibitor cyclopamine induced apoptosis in a subset of the pancreatic cancer cell lines both in culture and in mice (Sheng, T.; Li, C.; et al., Mol. Cancer. 2004, 3, 29).

Numerous studies indicate that Hh signaling is involved in prostate cancer. Sanchez and others reported the expression of Shh-Gli pathway components in adult human prostate cancer. Treatment of primary prostate tumor cultures and metastatic prostate cancer cell lines with Smo inhibitors blocked the pathway and proliferation. Increased expression of Shh in prostate cancer cells up-regulates Gill expression and dramatically accelerates the growth of prostate tumor xenografts (Fan, L.; Pepicelli, C. V.; et al., Endocrinology 2004, 145, 3961-3970). Elevated Shh activity distinguished metastatic from localized prostate cancer, and manipulation of this pathway modulated the invasiveness and metastasis of these tumors (Karhadkar, S. S.; Bova, G. S.; et al., Nature 2004, 431, 707-712).

Hh signaling has also been implicated in various other cancers, such as lung, colorectal, bladder, endometrial, ovarian, and esophageal carcinomas and rhabdomyosarcoma (Chi, S.; Huang, S.; et al., Cancer Lett. 2006, 244, 53-60; Watkins, D. N.; Berman, D. M.; et al., Nature 2003, 422, 313-317; Qualtrough, D.; Buda, A.; et al., Mt. J. Cancer 2004, 110, 831-837; McGarvey, T. W.; Maruta, Y.; Oncogene 1998, 17, 1167-1172; Feng, Y. Z.; Shiozawa, T.; et al., Clin. Cancer Res. 2007, 13, 1389-1398; Bhattacharya, R.; Kwon, J.; et al., Clin. Cancer Res. 2008, 14, 7659-7666; Mori, Y.; Okumura, T.; et al., Oncology 2006, 70, 378-389; Tostar, U.; Malm, C. J.; et al., J. Pathol. 2006, 208, 17-25; Hahn, H.; Wojnowski, L.; et al., Nat. Med. 1998, 4, 619-622). The role of Hh-Gli signaling pathway in cancer and its potential as therapeutic target have been reviewed in more detail in recent articles.

The aberrant activation of Hh-Gli signaling in several cancers has made it an attractive target for anticancer drug discovery. Various inhibitors of hedgehog signaling have been investigated such as cyclopamine, a natural alkaloid that had been showed to arrest cell cycle at arrest cell cycle at $G_0$-$G_1$ and to induce apoptosis in SCLC. Cyclopamine is believed to inhibit Smo by binding to its heptahelical bundle. Currently cyclopamine is in preclinical and clinical studies as an anticancer agent (Kolterud, A.; Toftga°rd, R. Drug Discovery Today: Ther. Strategies 2007, 4, 229-235). A number of Smo inhibitors have now been reported and can be classified as cyclopamine analogues or synthetic Smo antagonists. Several pharmaceutical companies have identified new Smo inhibitors with druglike properties by optimization of high throughput screen hits.

One such small molecule, GDC-0449, was developed by Curis and Genentech, is currently in phase I/II clinical trials for advanced BCC and solid epithelial tumor (Gunzner, J.; Sutherlin, D.; et al., WO2006028958, Mar. 16, 2006). Despite with these compounds, there still remains a need for potent inhibitors of the hedgehog signaling pathway.

DETAILED DESCRIPTION OF THE INVENTION

The present invention is related to compounds as shown in Formula (I):

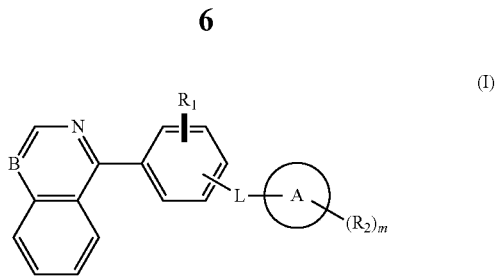

or a pharmaceutically acceptable salt thereof, wherein:

B is N or CH;

$R_1$ represents hydrogen, halogen, hydroxyl, amino, nitro, cyano, alkyl, alkenyl, alkoxy, alkoxycarbonyl, carbamoyl, alkylthio, sulfonyl, sulfinyl, cycloalkyl or a heterocycle;

L is oxygen, $NR_3$, $NR_3CO$, $NR_3SO$, $NR_3SO_2$, $SO_2NR_3$, $NR_3CONH$, $NR_3CSNH$, $CONR_3$, $CSNR_3$, $NR_3CHR_4$, $NR_3PO$ or $NR_3PO(OH)$;

Ring A is aryl, heterocycle, heteroaryl;

$R_2$ represents hydrogen, hydroxyl, halogen, amino, nitro, cyano, acvl, alkyl, alkenyl, alkynyl, alkylthio, sulfonyl, sulfinyl, alkoxy, alkoxycarbonyl, carbamoyl, acylamine, sulfamoyl or sulfonamide;

or $R_2$ is aryl, heterocycle or heteroaryl that is optionally substituted with hydroxyl, halogen, amino, nitro, cyano, acvl, alkyl, alkanoyl, sulfonyl, sulfinyl, alkoxy, carbamoyl, acylamine, sulfamoyl and sulfonamide;

$R_3$ and $R_4$ are independently selected from hydrogen or an optionally substituted $C_{1-4}$ alkyl group; and m is 0-4.

In a particular embodiment, compounds of the invention have the general formula Ia:

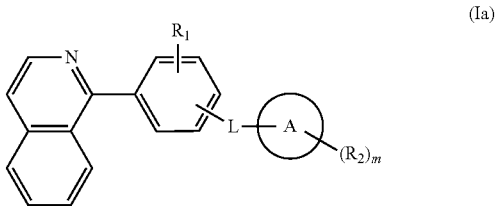

or a pharmaceutically acceptable salt thereof, wherein:

$R_1$ represents hydrogen, halogen, hydroxyl, amino, nitro, cyano, alkyl, alkenyl, alkoxy, alkoxycarbonyl, carbamoyl, alkylthio, sulfonyl, sulfinyl, cycloalkyl or a heterocycle;

L is oxygen, $NR_3$, $NR_3CO$, $NR_3SO$, $NR_3SO_2$, $SO_2NR_3$, $NR_3CONH$, $NR_3CSNH$, $CONR_3$, $CSNR_3$, $NR_3CHR_4$, $NR_3PO$ or $NR_3PO(OH)$;

Ring A is aryl, heterocycle, heteroaryl;

$R_2$ represents hydrogen, hydroxyl, halogen, amino, nitro, cyano, acyl, alkyl, alkenyl, alkynyl, alkylthio, sulfonyl, sulfinyl, alkoxy, alkoxycarbonyl, carbamoyl, acylamine, sulfamoyl or sulfonamide;

or $R_2$ is a aryl, heterocycle or heteroaryl that is optionally substituted with hydroxyl, halogen, amino, nitro, cyano, acyl, alkyl, alkanoyl, sulfonyl, sulfinyl, alkoxy, carbamoyl, acylamine, sulfamoyl and sulfonamide.

$R_3$ and $R_4$ are independently selected from hydrogen or an optionally substituted $C_{1-4}$ alkyl group; and m is 0-4.

In another particular embodiment, compounds of the invention have the general formula Ib.

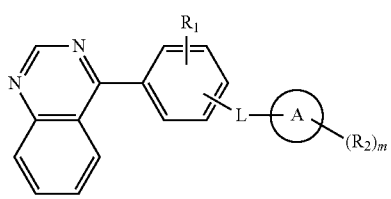

or a pharmaceutically acceptable salt thereof, wherein:

$R_1$ represents hydrogen, halogen, hydroxyl, amino, nitro, cyano, alkyl, alkenyl, alkoxy, alkoxycarbonyl, carbamoyl, alkylthio, sulfonyl, sulfinyl, cycloalkyl or a heterocycle;

L is oxygen, $NR_3$, $NR_3CO$, $NR_3SO$, $NR_3SO_2$, $SO_2NR_3$; $NR_3CONH$, $NR_3CSNH$, $CONR_3$, $CSNR_3$, $NR_3CHR_4$, $NR_3PO$ or $NR_3PO(OH)$;

Ring A is aryl, heterocycle, heteroaryl;

$R_2$ represents hydrogen, hydroxyl, halogen, amino, nitro, cyano, acyl, alkyl, alkenyl, alkynyl, alkylthio, sulfonyl, sulfinyl, alkoxy, alkoxycarbonyl, carbamoyl, acylamine, sulfamoyl or sulfonamide;

or $R_2$ is a aryl, heterocycle or heteroaryl that is optionally substituted with hydroxyl, halogen, amino, nitro, cyano, acyl, alkyl, alkanoyl, sulfonyl, sulfinyl, alkoxy, carbamoyl, acylamine, sulfamoyl and sulfonamide.

$R_3$ and $R_4$ are independently selected from hydrogen or an optionally substituted is $C_{1-4}$ alkyl group; and m is 0-4.

The following definitions refer to the various terms used above and throughout the disclosure.

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. Certain compounds are described herein using a general formula that include, variables (e.g. X, Ar.). Unless otherwise specified, each variable within such a formula is defined independently of any other variable, and any variable that occurs more than one time in a formula is defined independently at each occurrence.

The term "halo" or "halogen" refers to fluorine, chlorine, bromine or iodine. The term "alkyl" herein alone or as part of another group refers to a monovalent alkane (hydrocarbon) derived radical containing from 1 to 12 carbon atoms unless otherwise defined. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, dimethylpentyl, octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as $CCl_3$ or $CF_3$), alkoxy, alkylthio, hydroxy, carboxy (—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH). In some preferred embodiments of the present invention, alkyl groups are substituted with, for example, amino, heterocycloalkyl, such as morpholine, piperazine, piperidine, azetidine, hydroxyl, methoxy, or heteroaryl groups such as pyrrolidine.

The term "cycloalkyl" herein alone or as part of another group refers to fully saturated and partially unsaturated hydrocarbon rings of 3 to 9, preferably 3 to 7 carbon atoms. The examples include cyclopropyl, cyclobutyl, cyclopentyl and cyclohexyl, and like. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo (=O), hydroxy, alkoxy, thioalkyl, —$CO_2H$, —C(=O)H, $CO_2$-alkyl, —C(=O)alkyl, keto, =N—OH, =N—O-alkyl, aryl, heteroaryl, heterocyclo, —NR'R", —C(=O)NR'R", —$CO_2NR'R"$, —C(=O)NR'R", —NR'$CO_2R"$, —NR'C(=O)R", —$SO_2NR'R"$, and —NR'$SO_2R"$, wherein each of R' and R" are independently selected from hydrogen, alkyl, substituted alkyl, and cycloalkyl, or R' and R" together form a heterocyclo or heteroaryl ring.

The term "alkenyl" herein alone or as part of another group refers to a hydrocarbon radical straight, branched or cyclic containing from 2 to 12 carbon atoms and at least one carbon to carbon double bond. Examples of such groups include the vinyl, allyl, 1-propenyl, isopropenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, and the like. Alkenyl groups may also be substituted at any available point of attachment. Exemplary substituents for alkenyl groups include those listed above for alkyl groups, and especially include $C_3$ to $C_7$ cycloalkyl groups such as cyclopropyl, cyclopentyl and cyclohexyl, which may be further substituted with, for example, amino, oxo, hydroxyl, and the like.

The term "alkynyl" refers to straight or branched chain alkyne groups, which have one or more unsaturated carbon-carbon bonds, at least one of which is a triple bond. Alkynyl groups include $C_2$-$C_8$ alkynyl, $C_2$-$C_6$ alkynyl and $C_2$-$C_4$ alkynyl groups, which have from 2 to 8, 2 to 6 or 2 to 4 carbon atoms, respectively. Illustrative of the alkynyl group include ethenyl, propenyl, isopropenyl, butenyl, isobutenyl, pentenyl, and hexenyl. Alkynyl groups may also be substituted at any available point of attachment. Exemplary substituents for alkynyl groups include those listed above for alkyl groups such as amino, alkylamino, etc. The numbers in the subscript after the symbol "C" define the number of carbon atoms a particular group can contain.

The term "alkoxy" alone or as part of another group denotes an alkyl group as described above bonded through an oxygen linkage (—O—). Preferred alkoxy groups have from 1 to 8 carbon atoms. Examples of such groups include the methoxy, ethoxy, n-propoxy, isopropoxy, n-butoxy, isobutoxy, sec-butoxy, tert-butoxy, n-pentyloxy, isopentyloxy, n-hexyloxy, cyclohexyloxy, n-heptyloxy, n-octyloxy and 2-ethylhexyloxy.

The term "alkylthio" refers to an alkyl group as described above attached via a sulfur bridge. Preferred alkoxy and alkylthio groups are those in which an alkyl group is attached via the heteroatom bridge. Preferred alkylthio groups have from 1 to 8 carbon atoms. Examples of such groups include the methylthio, ethylthio, n-propylthio, n-butylthio, and like.

The term "oxo," as used herein, refers to a keto (C=O) group. An oxo group that is a substituent of a nonaromatic carbon atom results in a conversion of —$CH_2$— to —C(=O)—.

The term "alkanoyl" refers to groups of the formula: —C(O)R, where the R group is a straight or branched $C_1$-$C_6$ alkyl group, cycloalkyl, aryl, or heteroaryl.

The term "alkoxycarbonyl" herein alone or as part of another group denotes an alkoxy group bonded through a carbonyl group. An alkoxycarbonyl radical is represented by the formula: —C(O)OR, where the R group is a straight or branched $C_1$-$C_6$ alkyl group, cycloalkyl, aryl, or heteroaryl.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 20 atoms therein, with alternating (resonating) double bonds between adjacent carbon atoms or suitable heteroatoms. Aryl groups may optionally be substituted with one or more groups including, but not limited to halogen such as I, Br, F, or Cl; alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (where m=0, 1, 2), or thiol.

The term "amino" herein alone or as part of another group refers to —$NH_2$, an "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "heteroatom" refers to any atom other than carbon, for example, N, O, or S.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom.

The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or nonaromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —$CO_2$H, —C(=O)H, —$CO_2$-alkyl, —C(=O) alkyl, phenyl, benzyl, phenylethyl, phenyloxy, phenylthio, cycloalkyl, substituted cycloalkyl, heterocyclo, heteroaryl, —NR'R", —C(=O)NR'R", —$CO_2$NR'R", —C(=O)NR'R", —$NRCO_2$R", —$NR_1$C(=O)R", —$SO_2$NR'R", and —$NR'SO_2$R", wherein each of R' and R" is independently selected from hydrogen, alkyl, substituted alkyl, and cycloalkyl, or R' and R" together form a heterocyclo or heteroaryl ring.

Preferably monocyclic heteroaryl groups include pyrrolyl, pyrazolyl, pyrazolinyl, imidazolyl, oxazolyl, diazolyl, isoxazolyl, thiazolyl, thiadiazolyl, S isothiazolyl, furanyl, thienyl, oxadiazolyl, pyridyl, pyrazinyl, pyrimidinyl, pyridazinyl, triazinyl and the like.

Preferably bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, dihydroisoindolyl, tetrahydroquinolinyl and the like.

Preferably tricyclic heteroaryl groups include carbazolyl, benzidolyl, phenanthrollinyl, acridinyl, phenanthridinyl, xanthenyl and the like.

The term "heterocycle" or "heterocycloalkyl" herein alone or as part of another group refers to a cycloalkyl group (non-aromatic) in which one of the carbon atoms in the ring is replaced by a heteroatom selected from O, S or N. The "heterocycle" has from 1 to 3 fused, pendant or spiro rings, at least one of which is a heterocyclic ring (i.e., one or more ring atoms is a heteroatom, with the remaining ring atoms being carbon). The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy; lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. A heterocyclic group may generally be linked via any ring or substituent atom, provided that a stable compound results. N-linked heterocyclic groups are linked via a component nitrogen atom.

Typically, a heterocyclic ring comprises 1-4 heteroatoms; within certain embodiments to each heterocyclic ring has 1 or 2 heteroatoms per ring. Each heterocyclic ring generally contains from 3 to 8 ring members (rings having from to 7 ring members are recited in certain embodiments), and heterocycles comprising fused, pendant or spiro rings typically contain from 9 to 14 ring members which consists of carbon atoms and contains one, two, or three heteroatoms selected from nitrogen, oxygen and/or sulfur.

Examples of "heterocycle" or "heterocycloalkyl groups include piperazine, piperidine, morpholine, thiomorpholine, pyrrolidine, imidazolidine and thiazolide.

The term "carbamoyl" herein refers to aminocarbonyl containing substituent represented by the formula $C(O)N(R)_2$ in which R is H, hydroxyl, alkyl, a carbocycle, a heterocycle, carbocycle-substituted alkyl or alkoxy, or heterocycle-substituted alkyl or alkoxy wherein the alkyl, alkoxy, carbocycle and heterocycles are as herein defined. Carbomoyl groups include alkylaminocarbonyl (e.g. ethylaminocarbonyl, Et-NH—CO—), arylaminocarbonyl (e.g. phenylaminocarbonyl), aralkylaminocarbonyl (e.g. benzoylaminocarbonyl), heterocycleaminocarbonyl (e.g. piperizinylaminocarbonyl), and in particular a heteroarylaminocarbonyl (e.g. pyridylaminocarbonyl).

The term "sulfamoyl" herein refers to —$SO_2$—$N(R)_2$ wherein each R is independently H, alkyl, carbocycle, heterocycle, carbocycloalkyl or heterocycloalkyl. Particular sulfamoyl groups are alkylsulfamoyl, for example methylsulfamoyl (—SO$_2$—NHMe); arylsulfamoyl, for example phenylsulfamoyl; aralkylsulfamoyl, for example benzylsulfamoyl.

The term "sulfinyl" herein refers to —SOR wherein R is alkyl, carbocycle, heterocycle, carbocycloalkyl or heterocycloalkyl. Particular sulfinyl groups are alkylsulfinyl (i.e. —SO-alkyl), for example methylsulfinyl; arylsulfinyl (i.e. —SO— aryl) for example phenylsulfinyl; arakylsulfinyl, for example benzylsulfinyl.

The term "sulfoamide" herein refers to —NR—SO$_2$—R wherein each R is independently H, alkyl, carbocycle, heterocycle, carbocycloalkyl or heterocycloalkyl), a carbocycle or a heterocycle. Particular sulfonamide groups are alkylsulfonamide (e.g. —NH—SO$_2$-alkyl), for example methylsulfonamide; arylsulfonamide (e.g. —NH—SO$_2$-aryl), for example phenylsulfonamide; aralkylsulfonamide, for example benzylsulfonamide.

The term "sulfonyl" herein refers to —SO$_2$—R group wherein R is alkyl, carbocycle, heterocycle, carbocycloalkyl or heterocycloalkyl. Particular sulfonyl groups are alkylsulfonyl (e.g. —SO$_2$-alkyl), for example methylsulfonyl; arylsulfonyl, for example phenylsulfonyl; araalkylsulfonyl, for example benzylsulfonyl.

A dash ("-") that is not between two letters or symbols is used to indicate a point of attachment for a substituent. For example, —CONH$_2$ is attached through the carbon atom.

The term "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member.

The term "optionally substituted" as it refers that the aryl or heterocyclyl or other group may be substituted at one or more substitutable positions by one or more groups independently selected from alkyl (preferably lower alkyl), alkoxy (preferably lower alkoxy), nitro, monoalkylamino (preferably with one to six carbons), dialkylamino (preferably with one to six carbons), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy and lower alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Optional substitution is also indicated by the phrase "substituted with from 0 to X substituents," where X is the maximum number of possible substituents. Certain optionally substituted groups are substituted with from 0 to 2, 3 or 4 independently selected substituents.

The term "pharmaceutically acceptable salt" of a compound recited herein is an acid or base salt that is suitable for use in contact with the tissues of human beings or animals without excessive toxicity or carcinogenicity, and preferably without irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH$_2$)$_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein. In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, the use of nonaqueous media, such as ether, ethyl acetate, ethanol, isopropanol or acetonitrile, is preferred. It will be apparent that each compound of Formula I may, but need not, be formulated as a hydrate, solvate or non-covalent complex. In addition, the various crystal forms and polymorphs are within the scope of the present invention. Also provided herein are prodrugs of the compounds of Formula I.

Groups that are "optionally substituted" are unsubstituted or are substituted by other than hydrogen at one or more available positions. Such optional substituents include, for example, hydroxy, halogen, cyano, nitro, C$_1$-C$_6$ alkyl, C$_2$-C$_6$ alkenyl, C$_2$-C$_6$ alkynyl, C$_1$-C$_6$ alkoxy, C$_2$-C$_6$ alkyl ether, C$_3$-C$_6$ alkanone, C$_2$-C$_6$ alkylthio, amino, mono- or di-(C$_1$-C$_6$ alkyl)amino, C$_1$-C$_6$ haloalkyl, —COON, —CONH$_2$, mono- or di-(C$_1$-C$_6$ alkyl)-aminocarbonyl, —SO$_2$NH$_2$, and/or mono or di(C$_1$-C$_6$ alkyl) sulfonamido, as well as carbocyclic and heterocyclic groups.

Optional substitution is also indicated by the phrase "substituted with from 0 to X substituents," where X is the maximum number of possible substituents. Certain optionally substituted groups are substituted with from 0 to 2, 3 or 4 independently selected substituents.

In a particular embodiment A is a ring selected from the below groups:

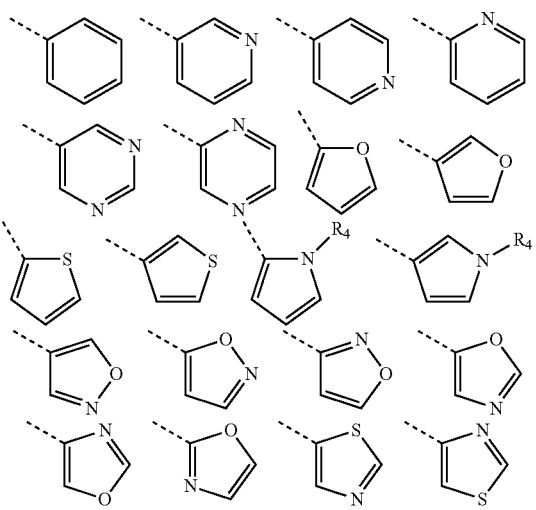

-continued
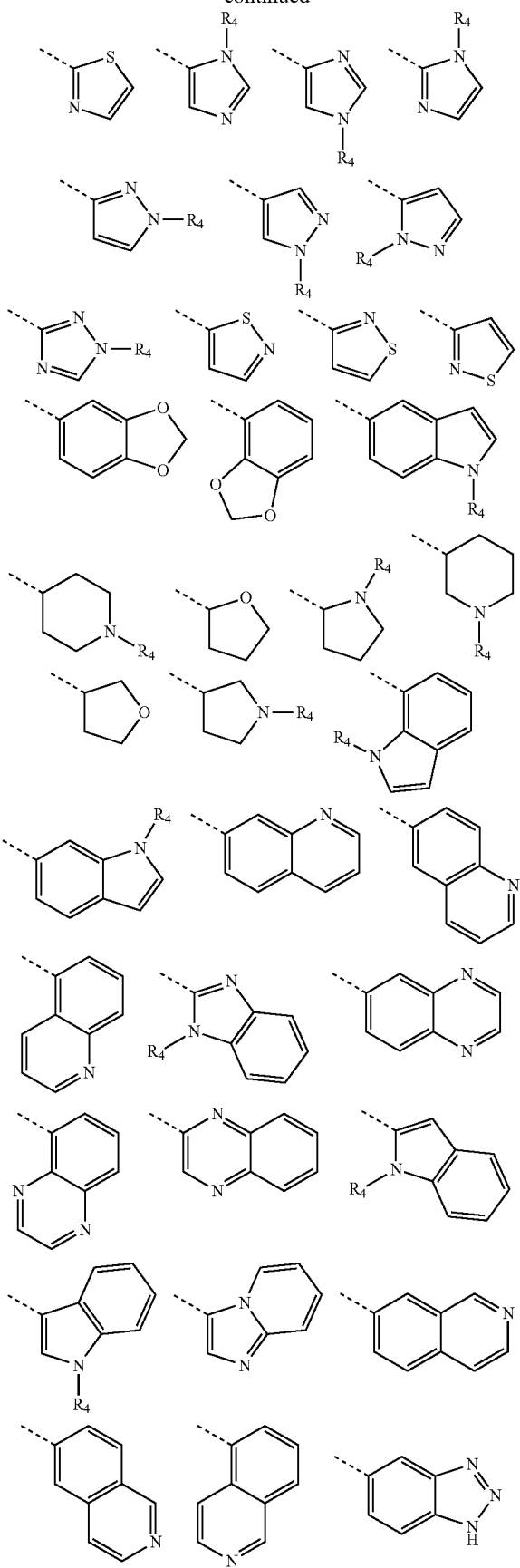
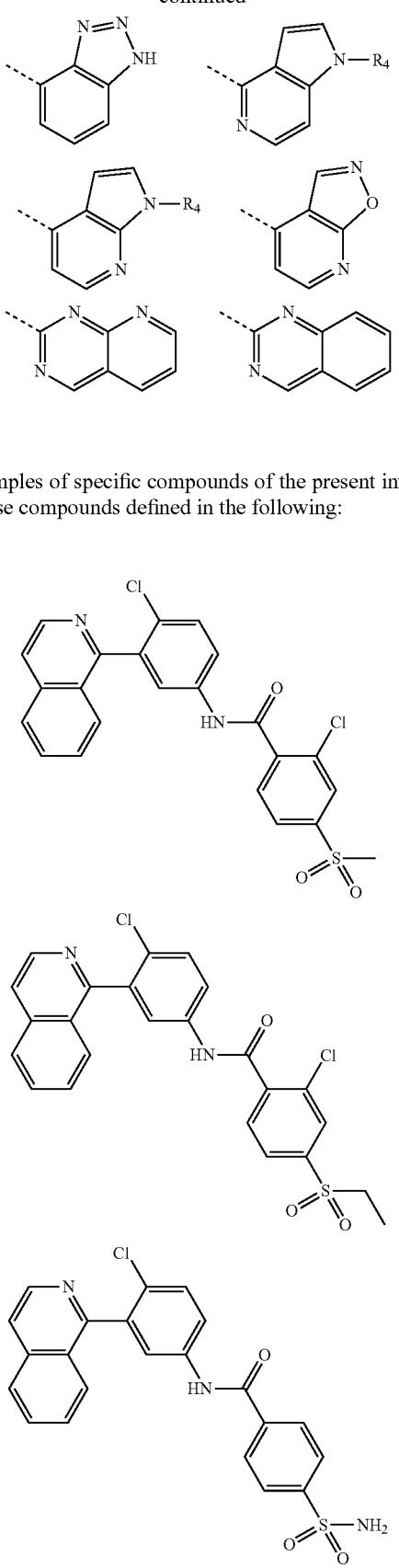
Examples of specific compounds of the present invention are those compounds defined in the following:

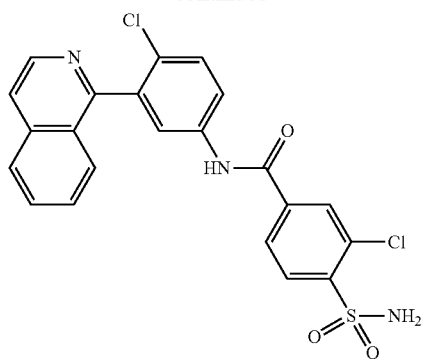
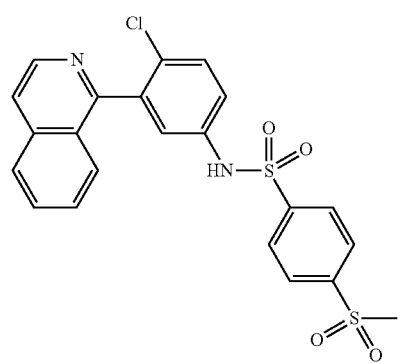
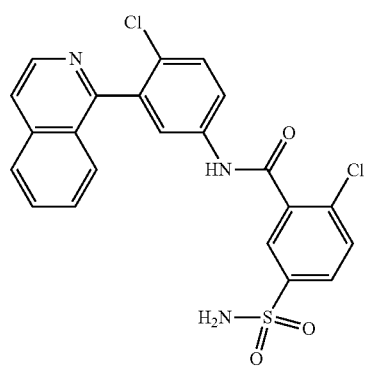
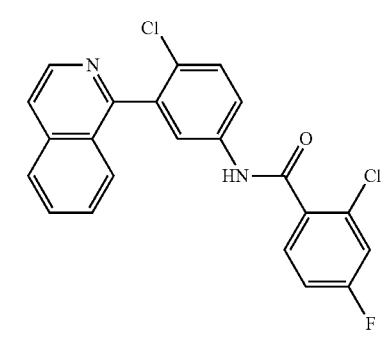
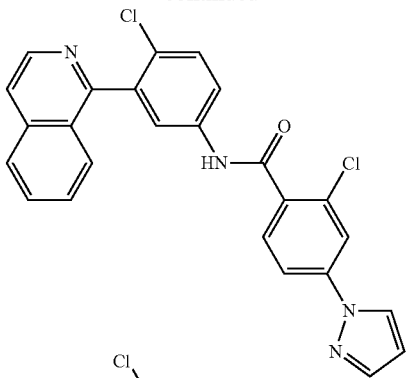
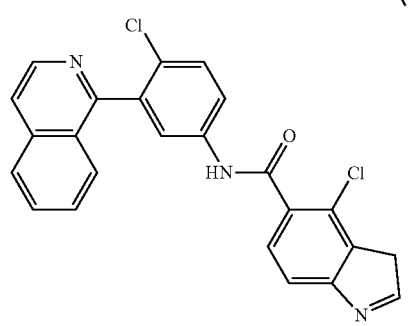
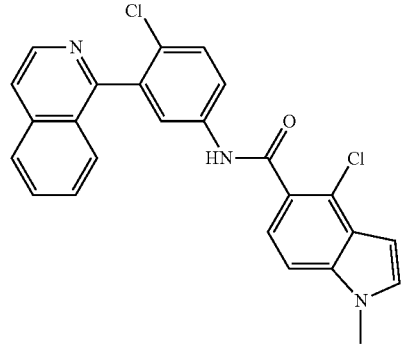
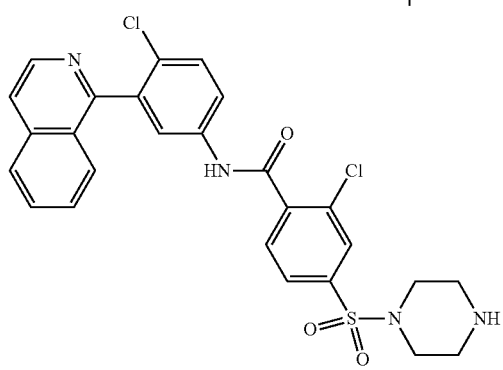

-continued
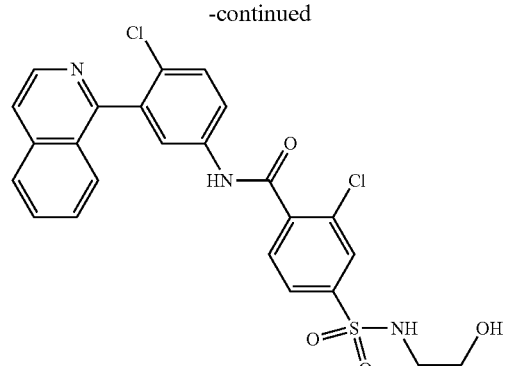
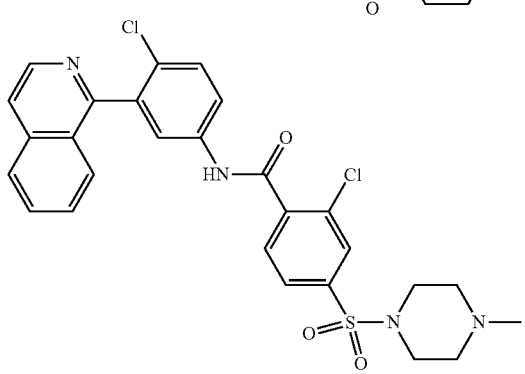
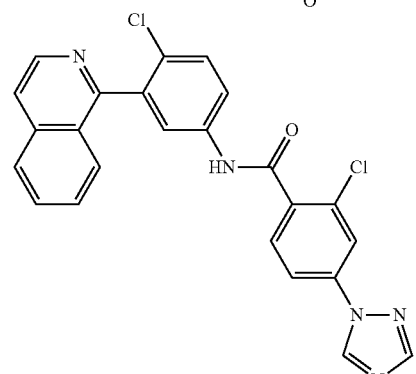
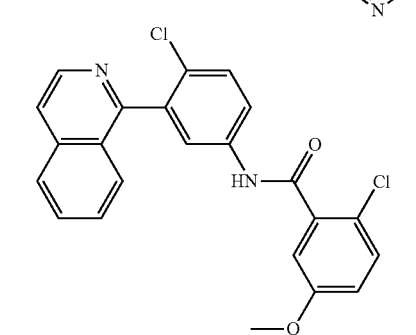
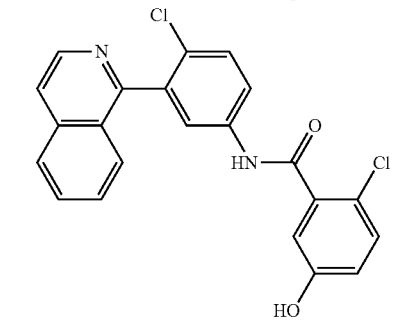
-continued
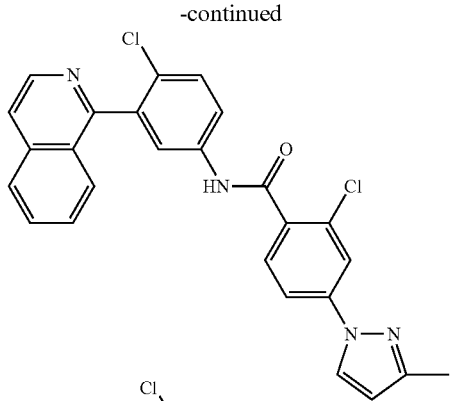
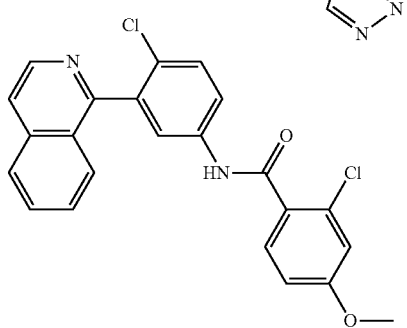
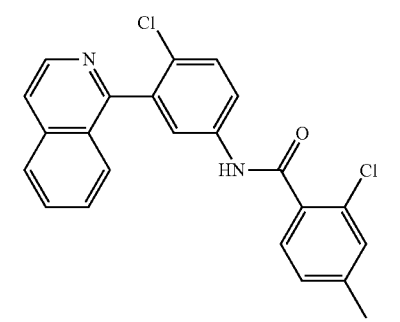
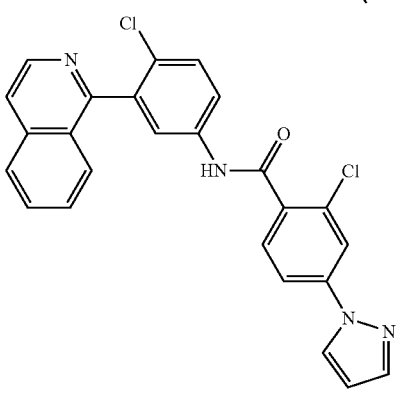

-continued
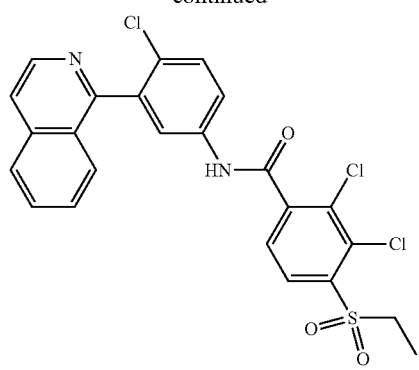
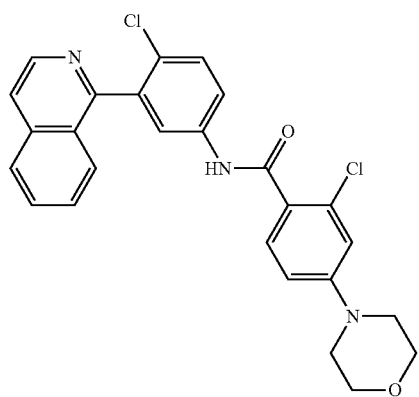
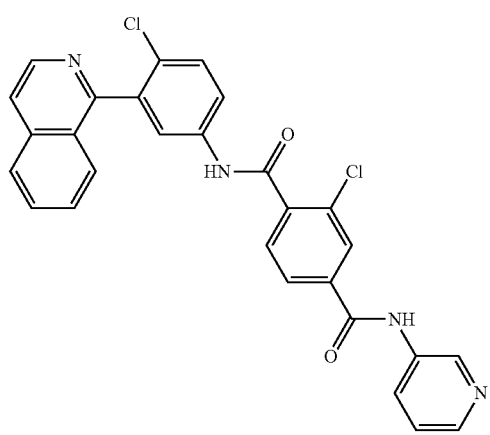
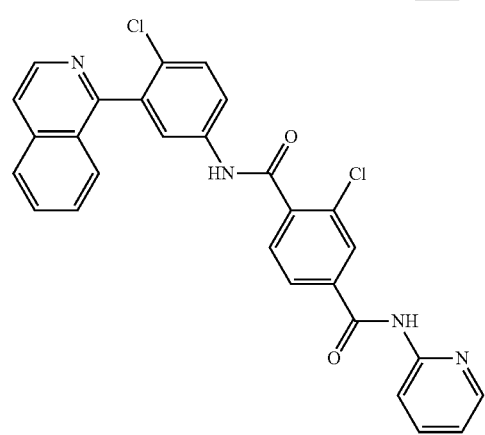
-continued
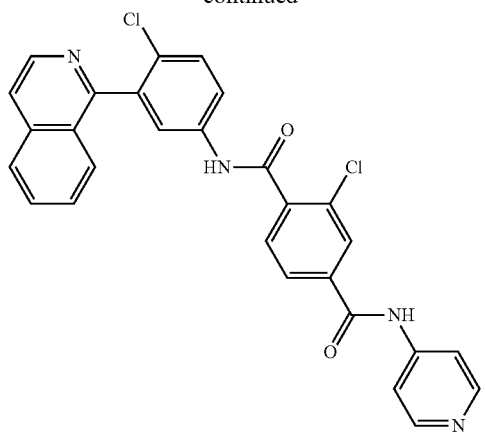
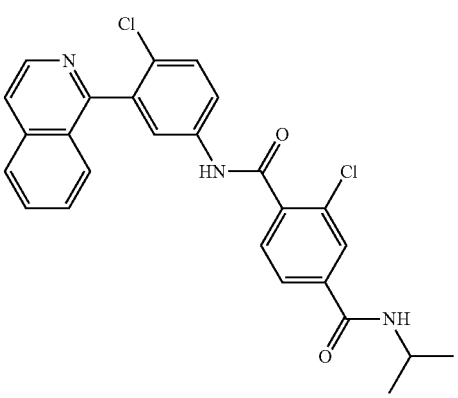
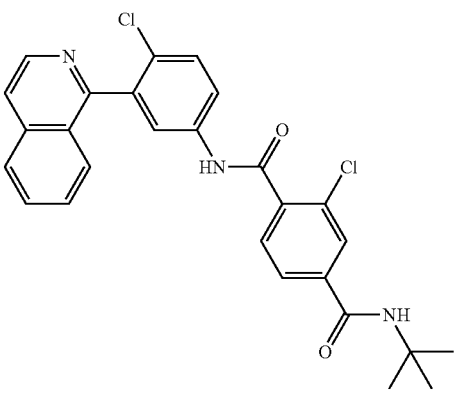
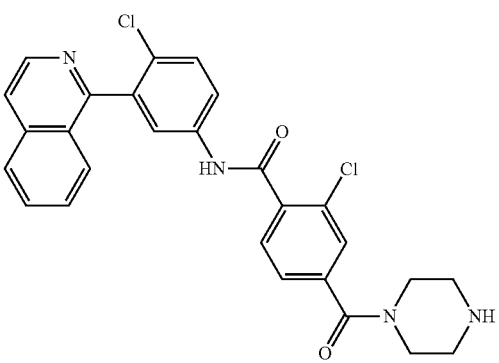

21
-continued
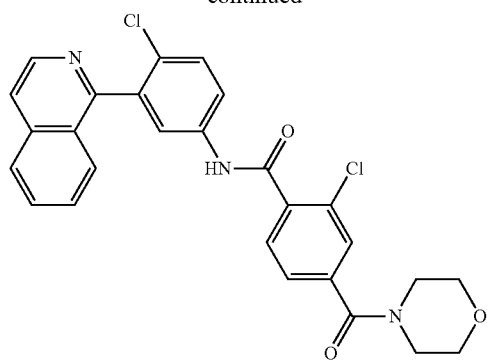
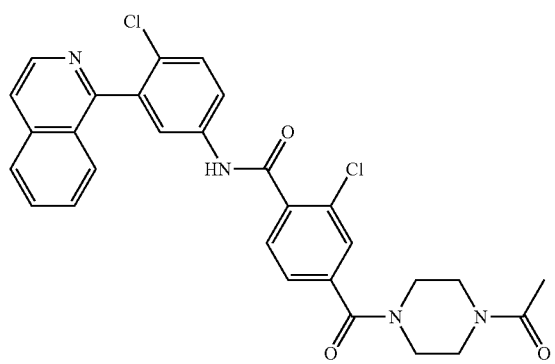
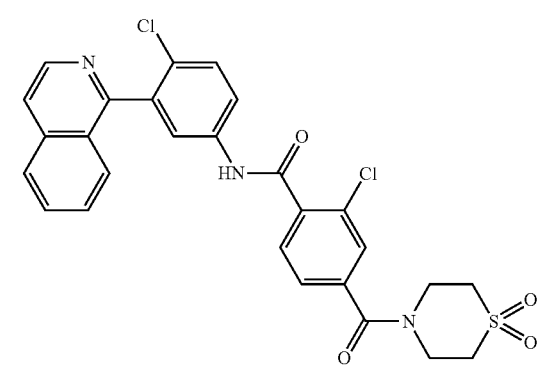
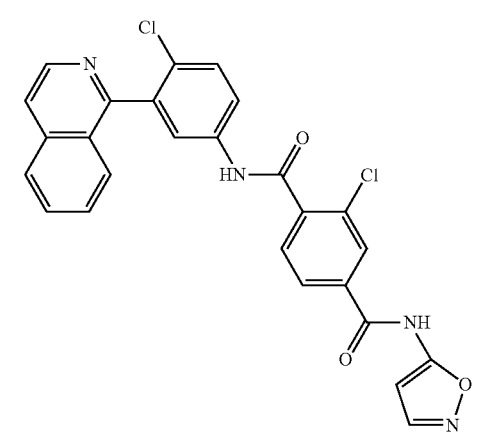
22
-continued
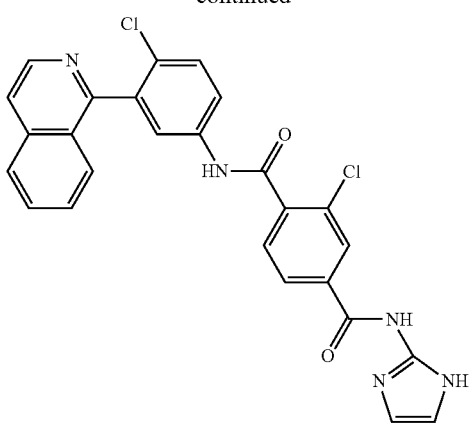
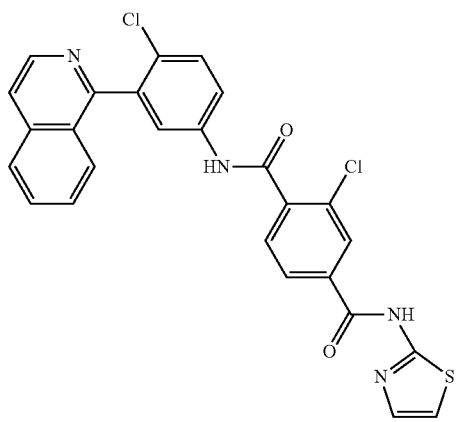
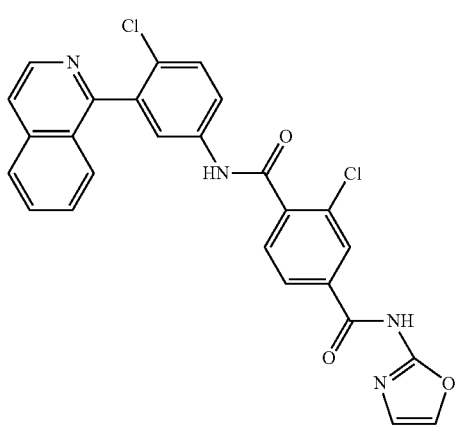
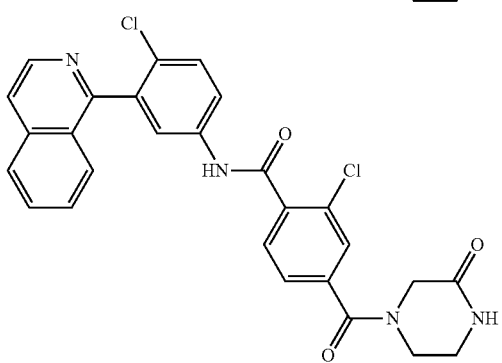

-continued
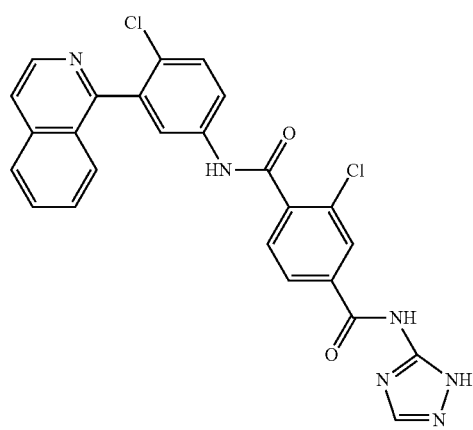
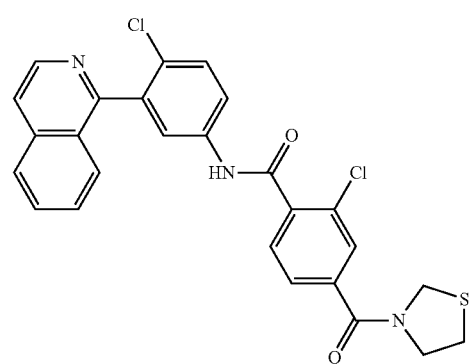
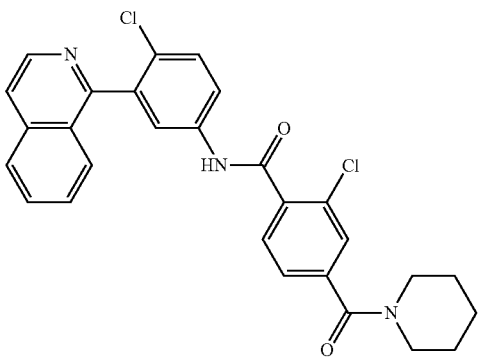
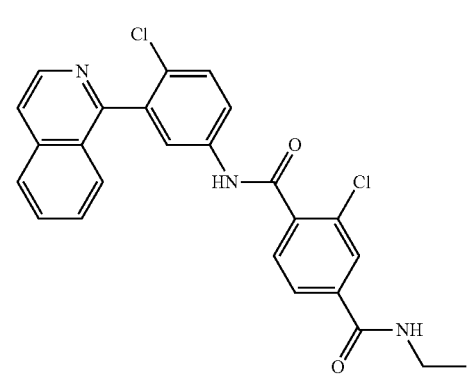
-continued
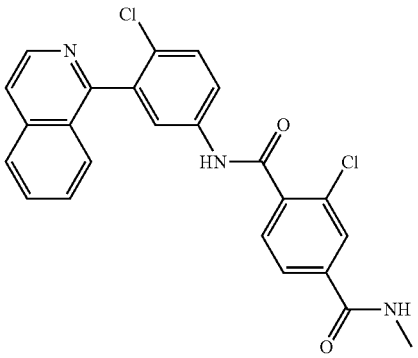
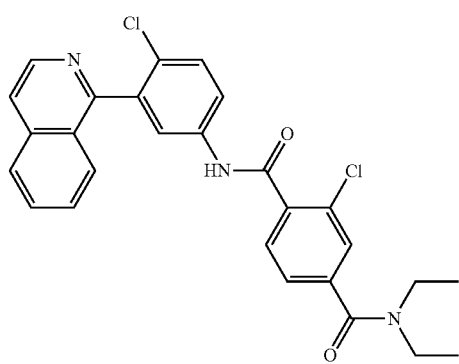
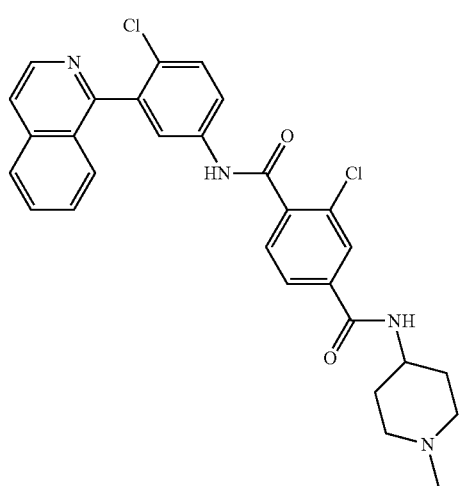
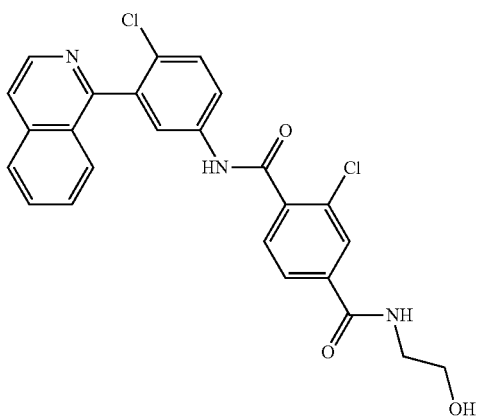

25
-continued
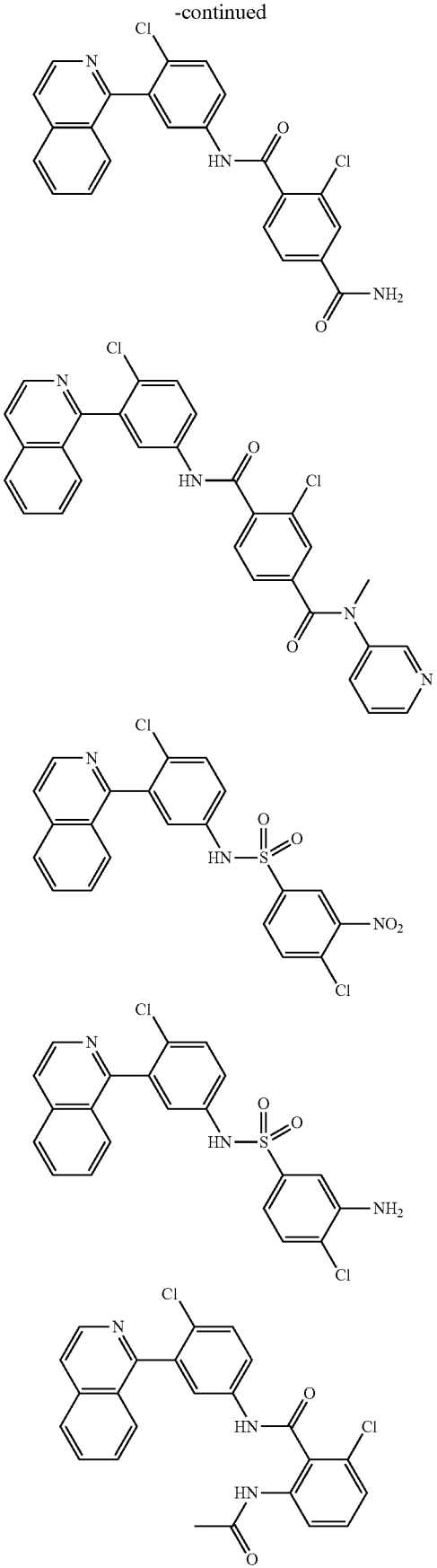
26
-continued
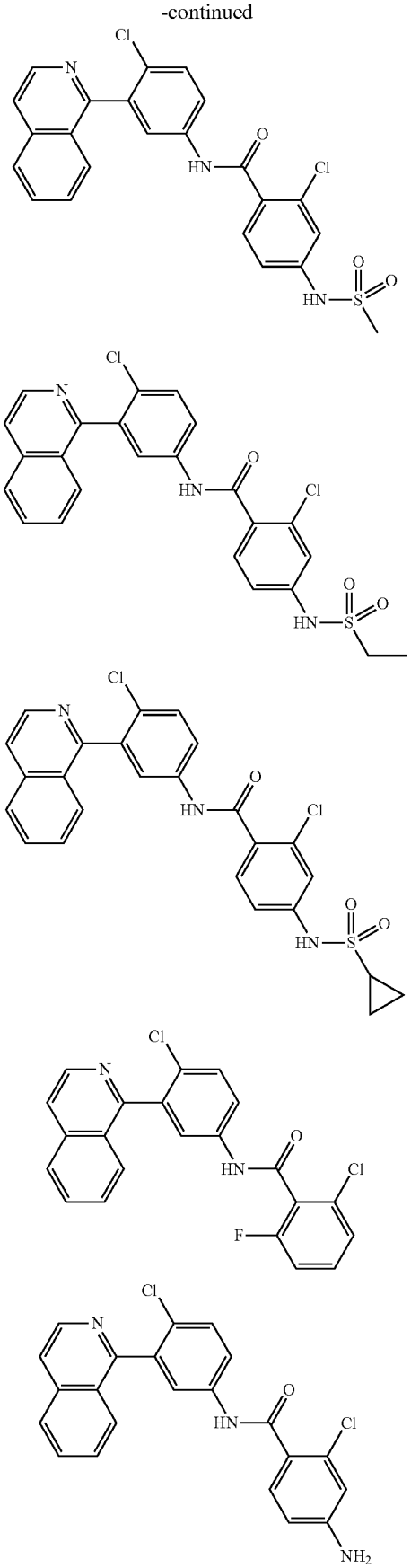

-continued
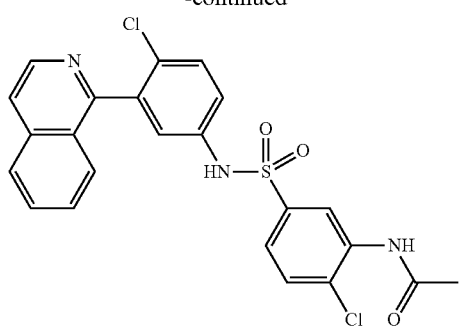
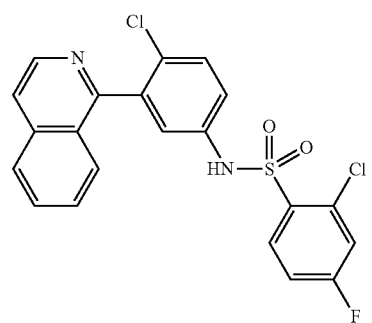
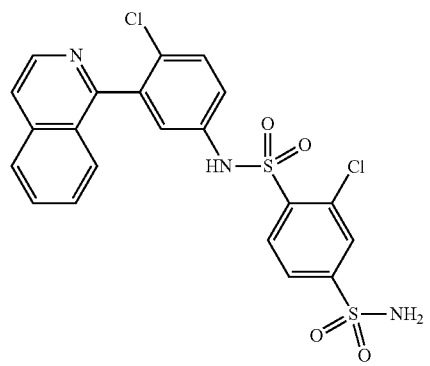
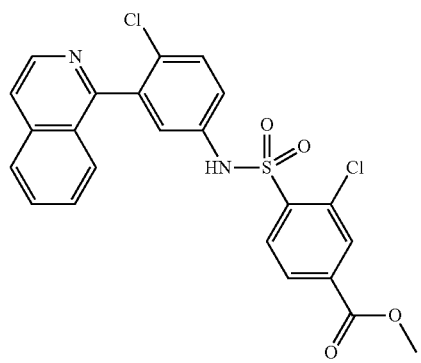
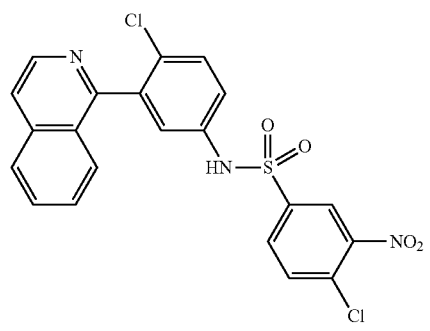
-continued
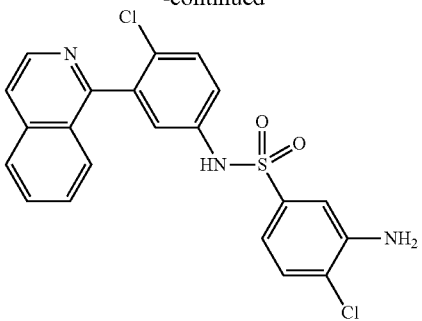
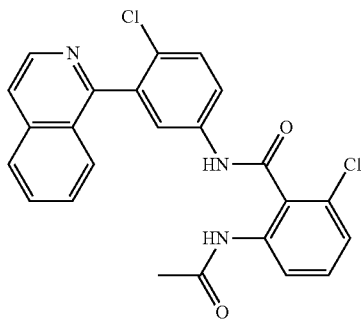
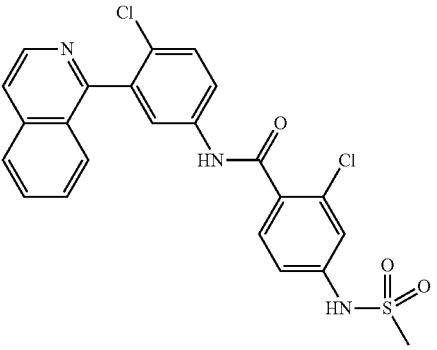
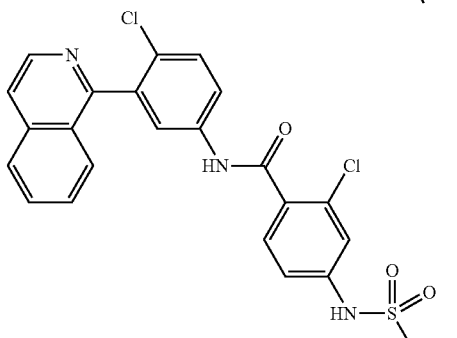
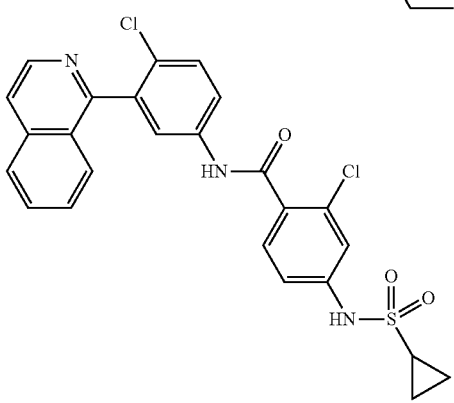

-continued
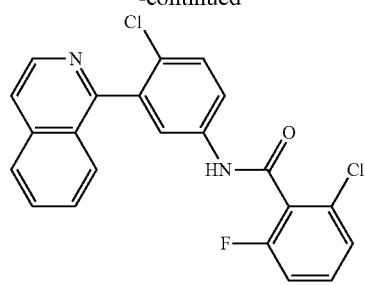
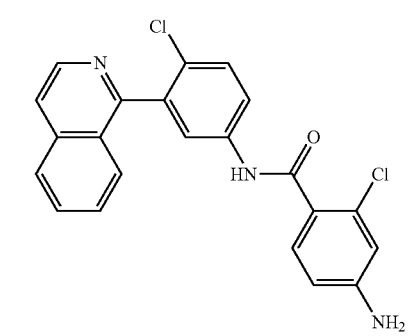
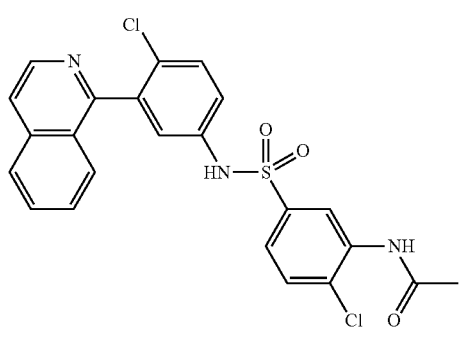
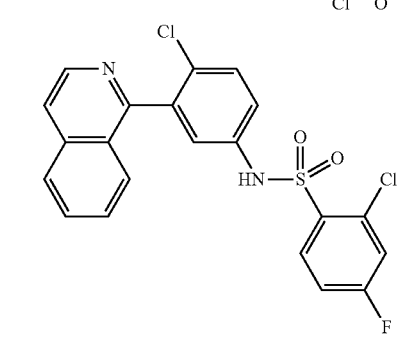
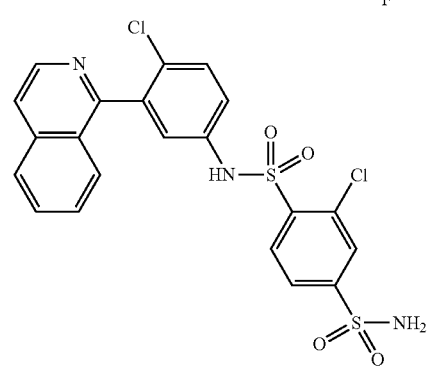
-continued
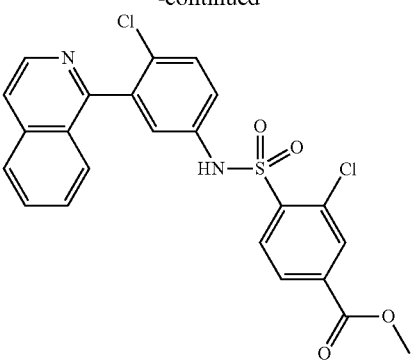
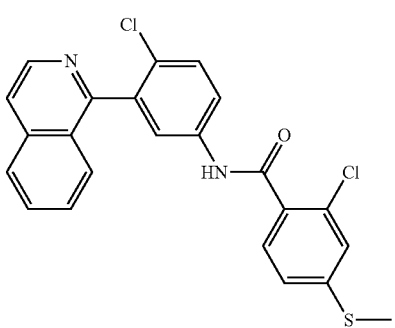
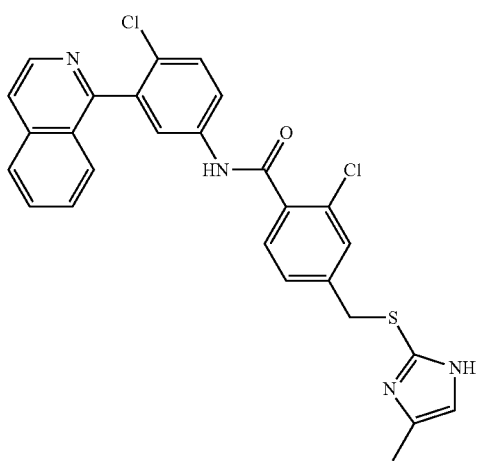
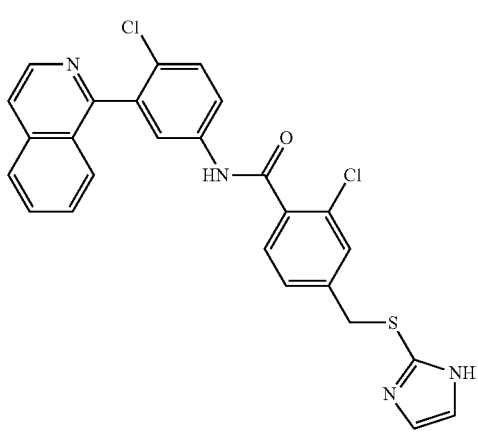

31
-continued
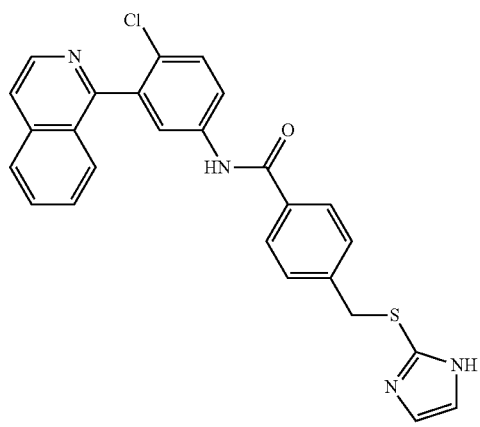
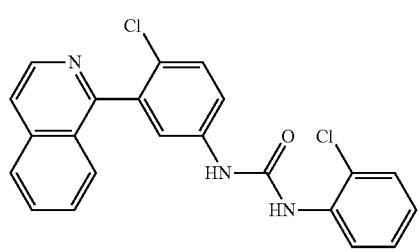
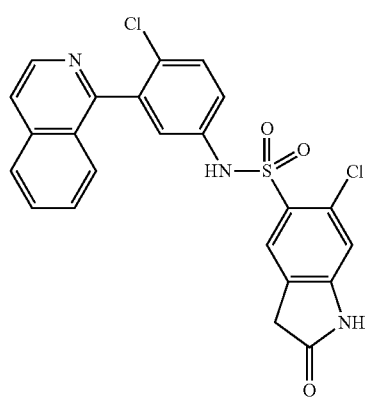
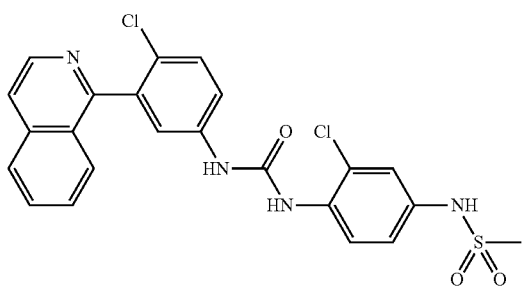
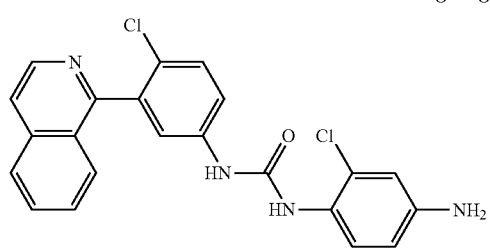
32
-continued
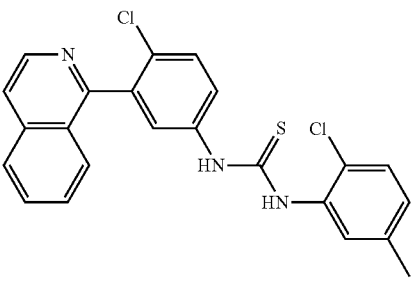
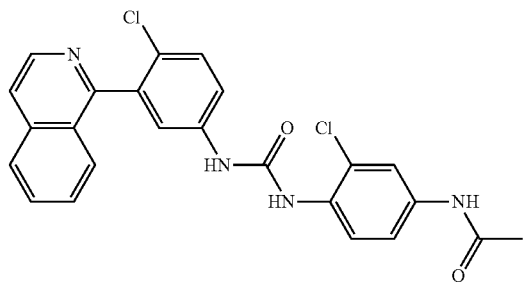
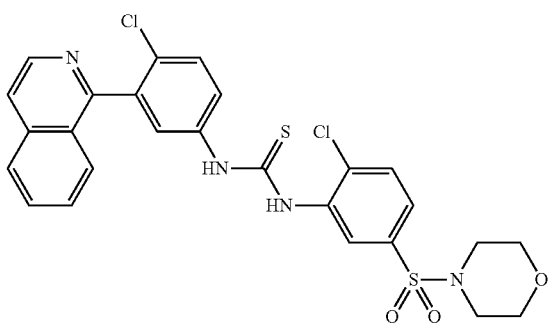
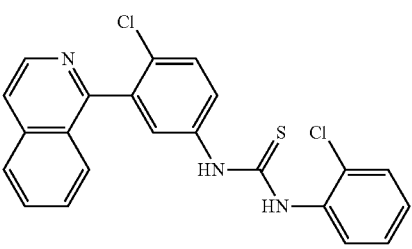
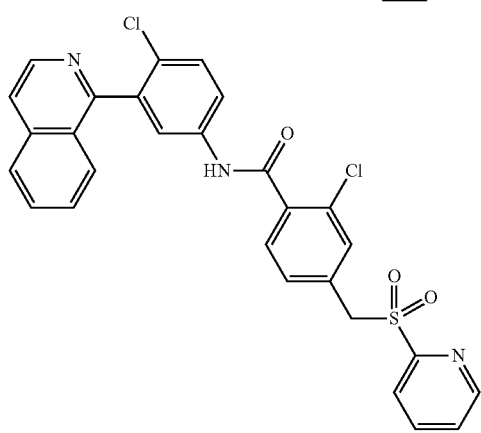

-continued
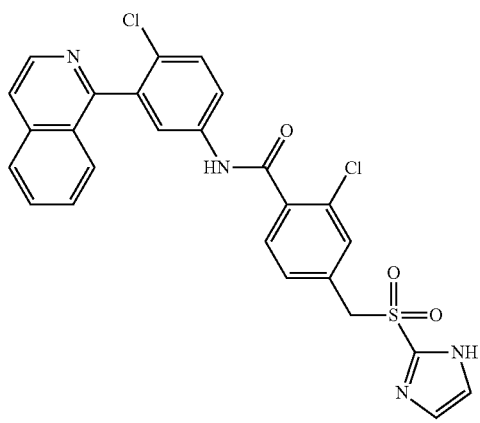
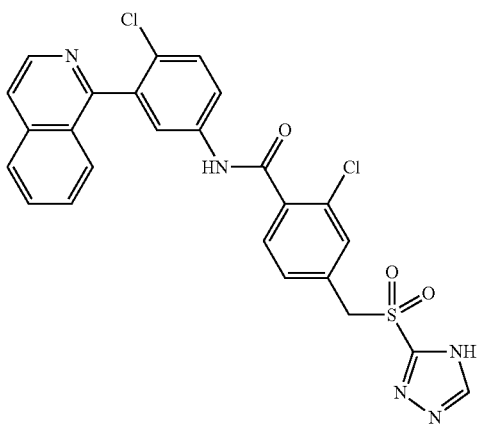
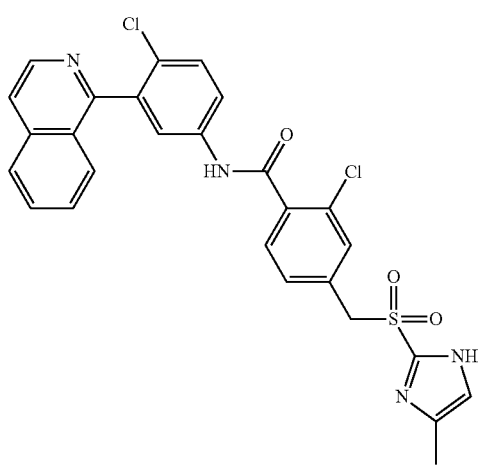
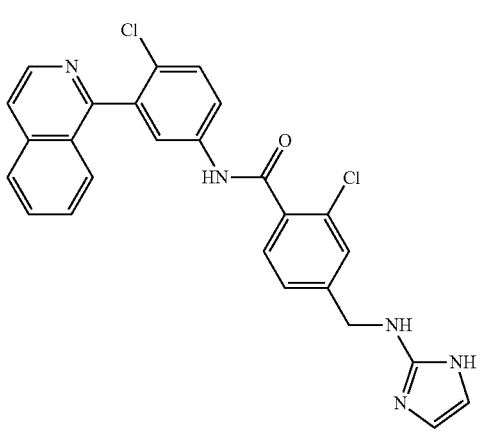
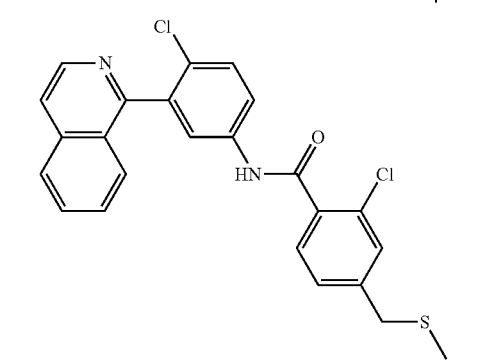
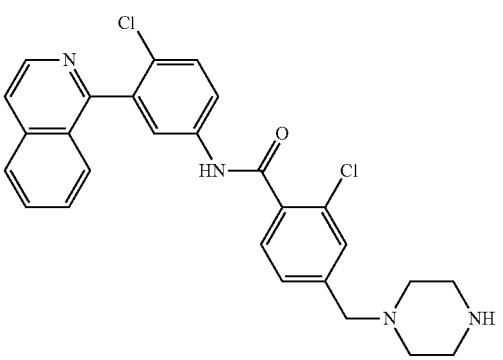
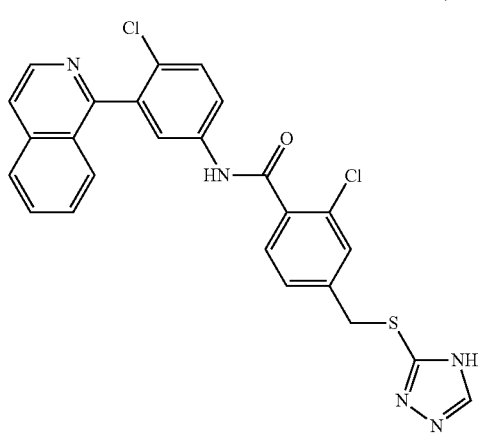
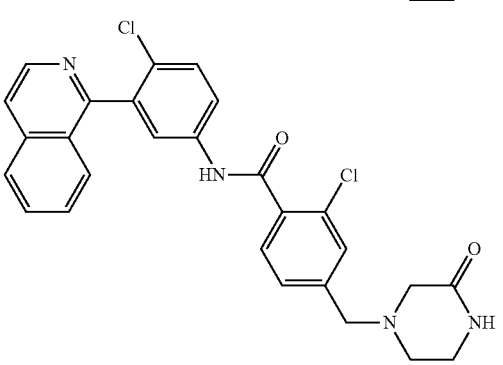

-continued
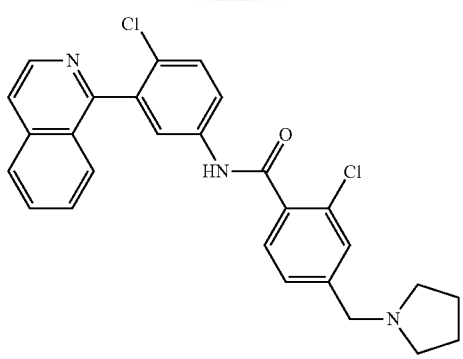
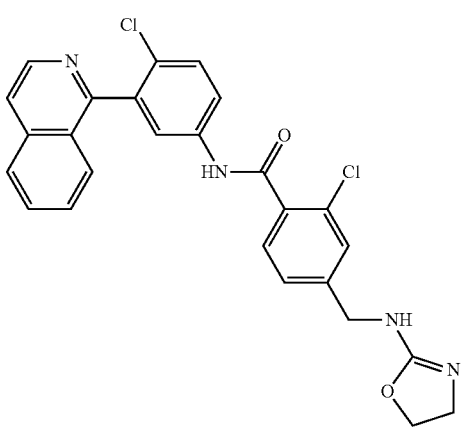
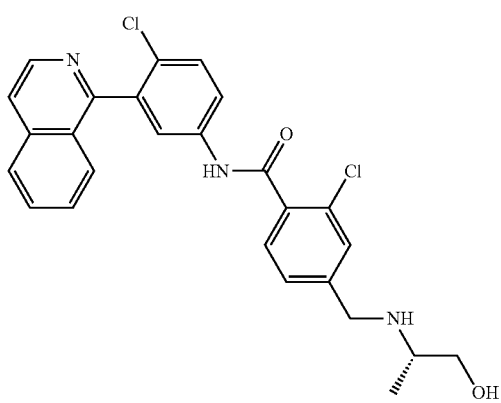
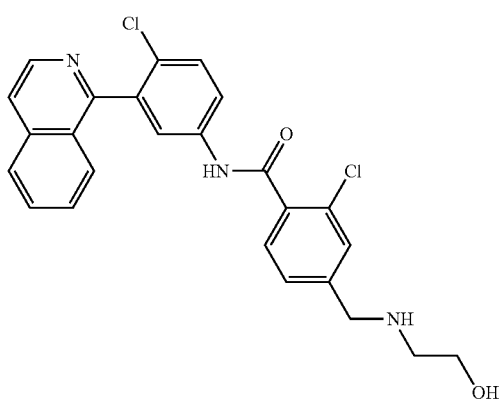
-continued
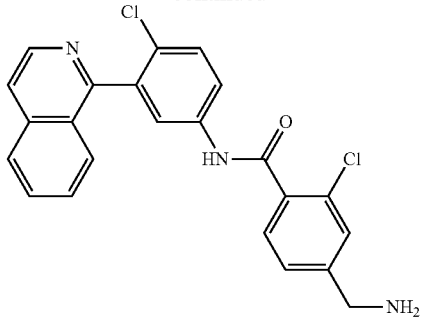
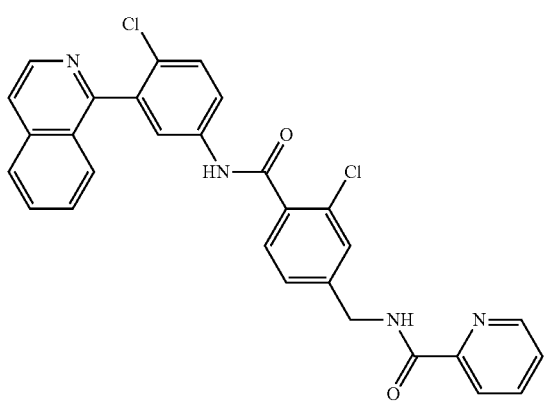
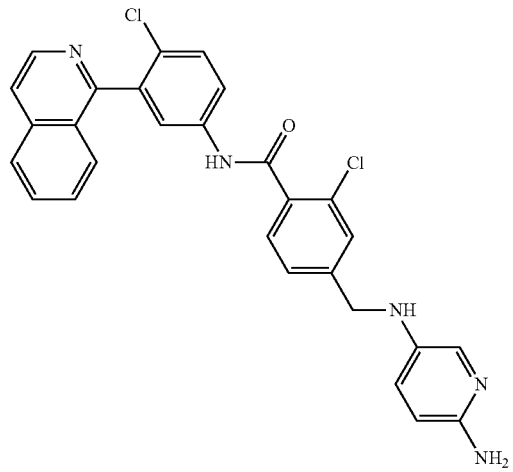
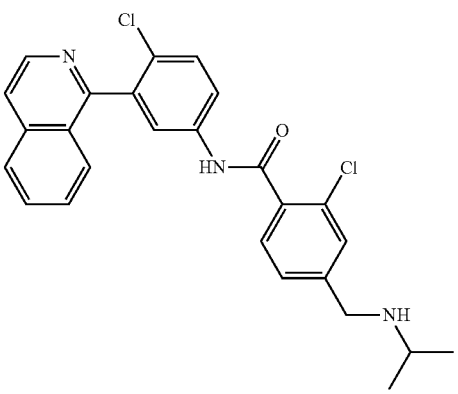

37
-continued
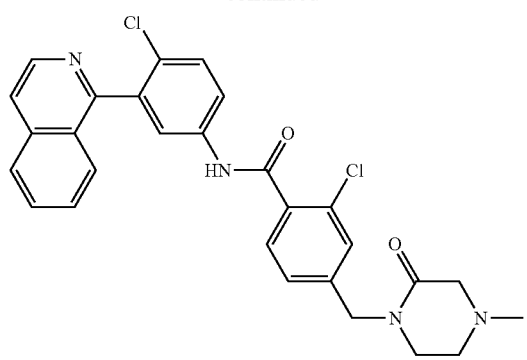
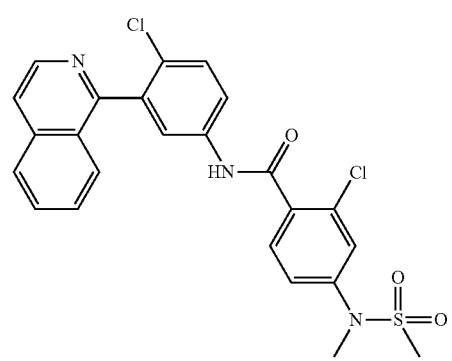
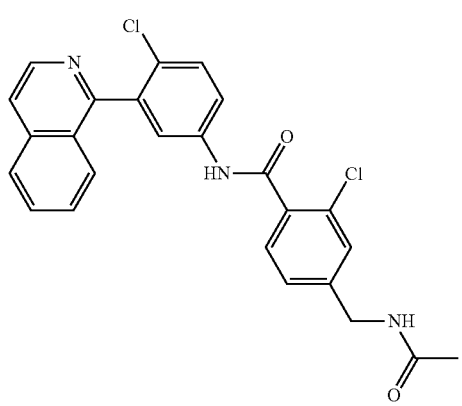
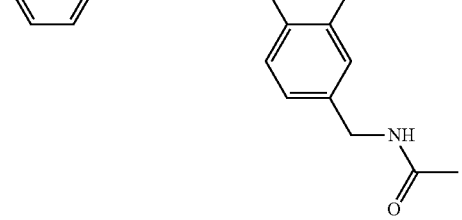
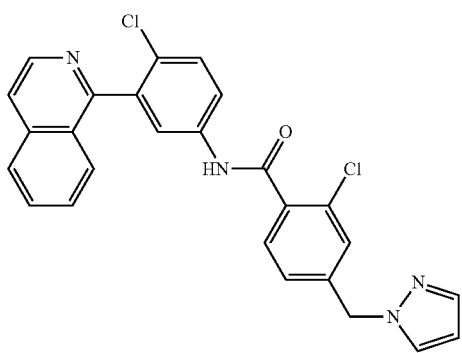
38
-continued
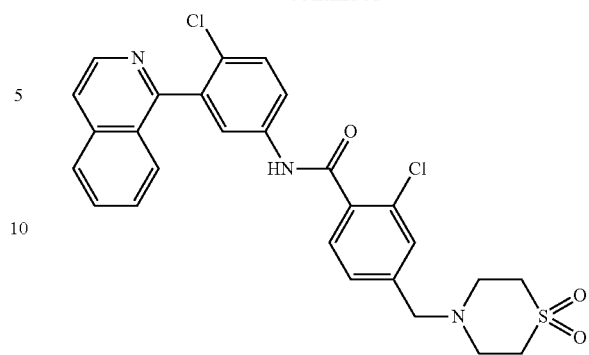
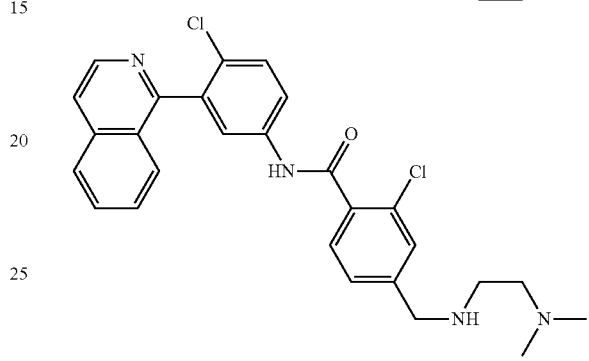
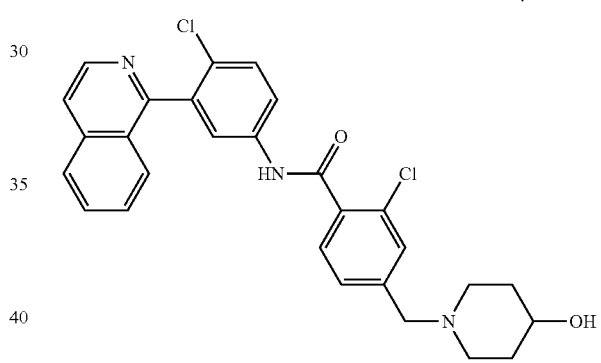
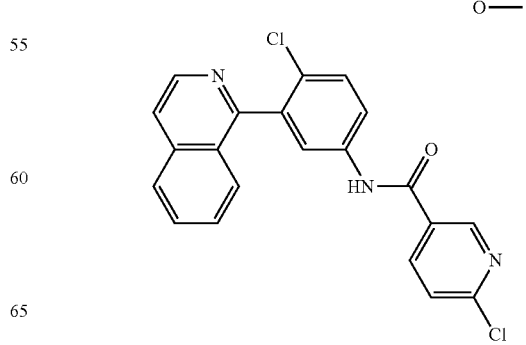

-continued
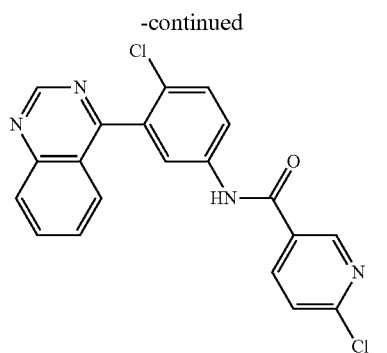
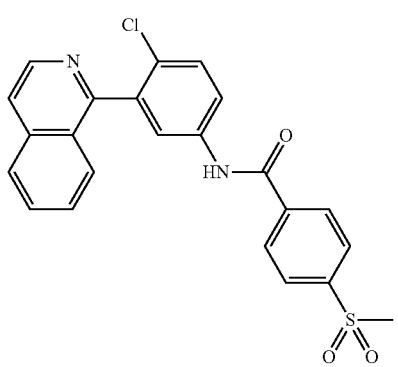
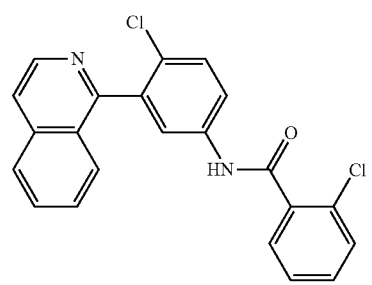
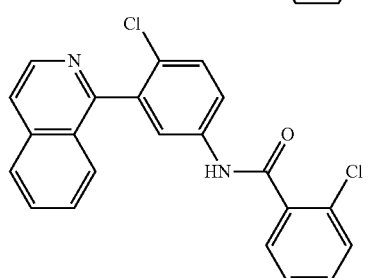
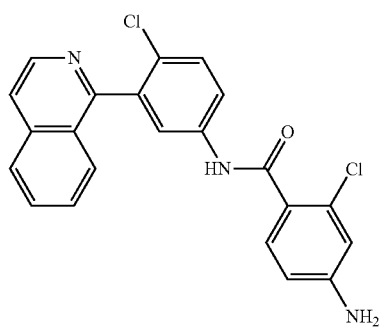
-continued
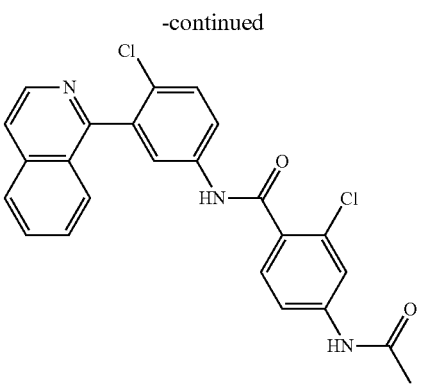
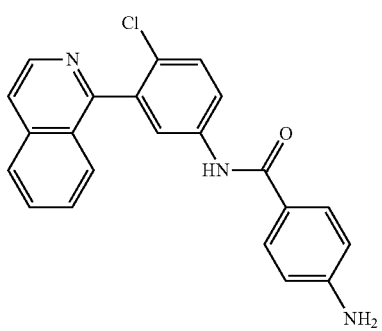
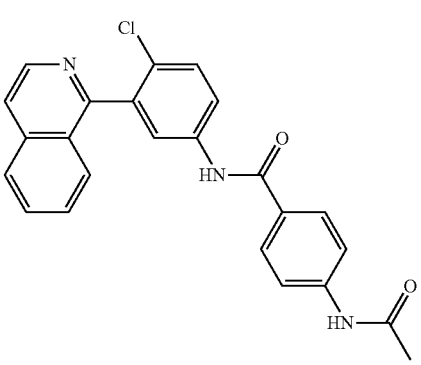
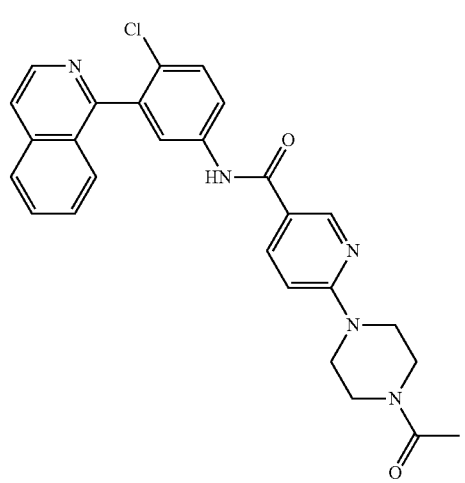

-continued
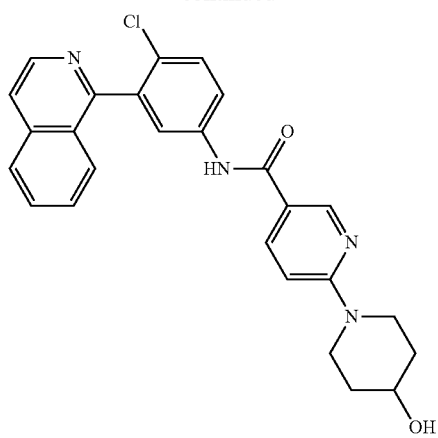
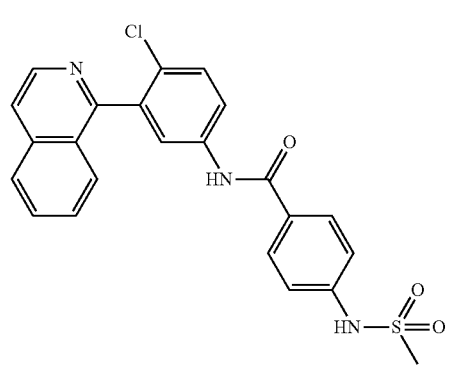
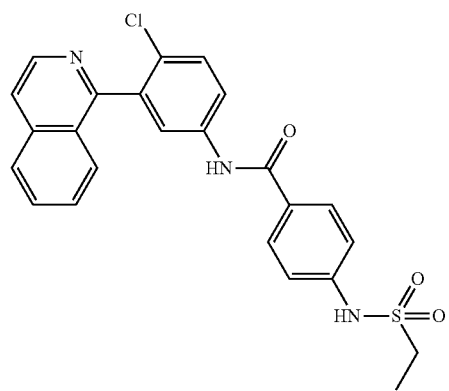
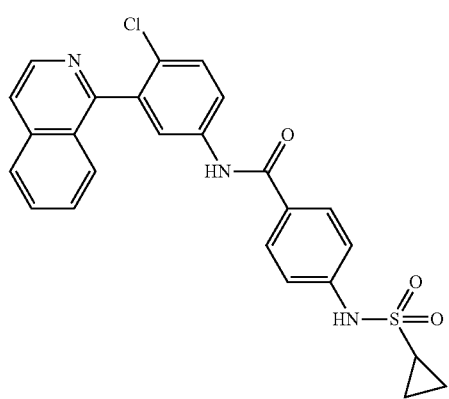
-continued
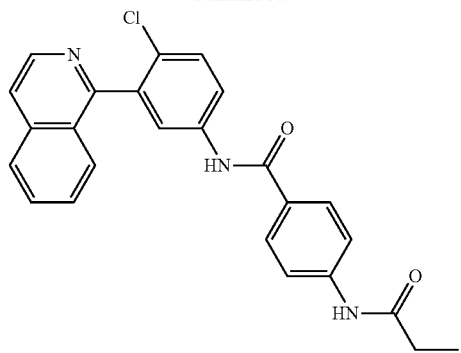
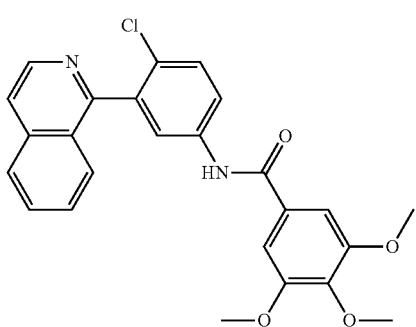
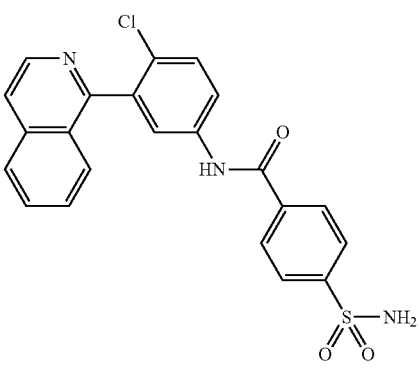
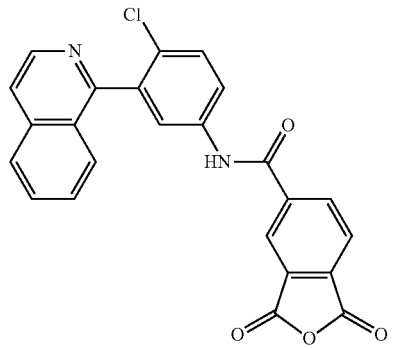
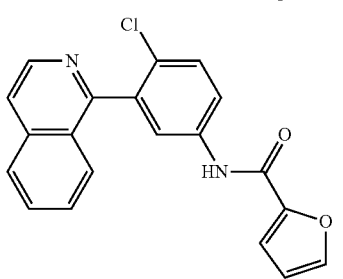

-continued
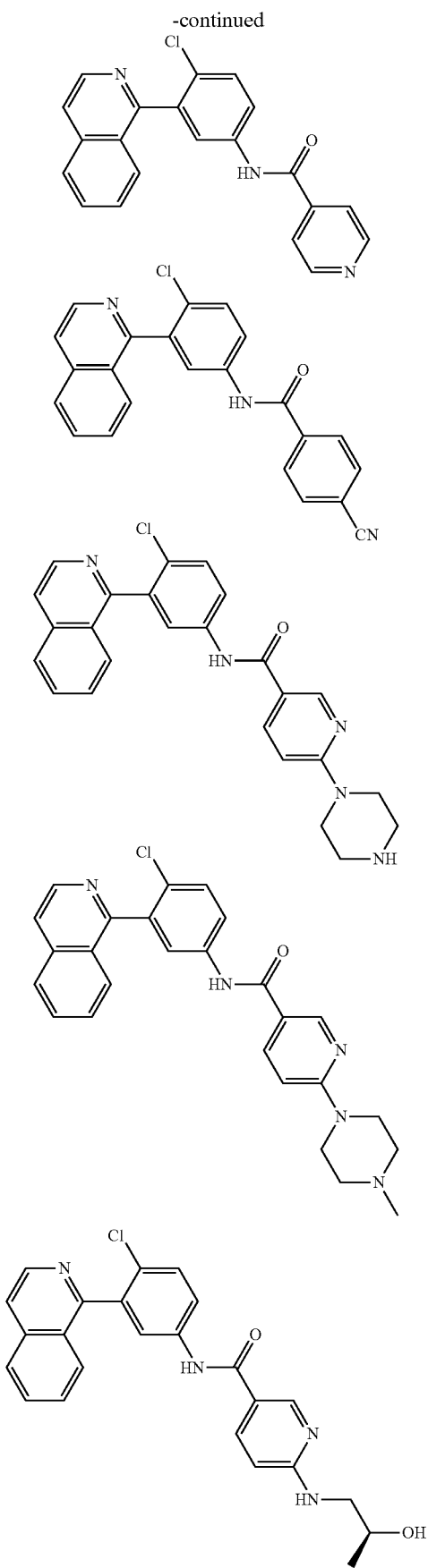
-continued
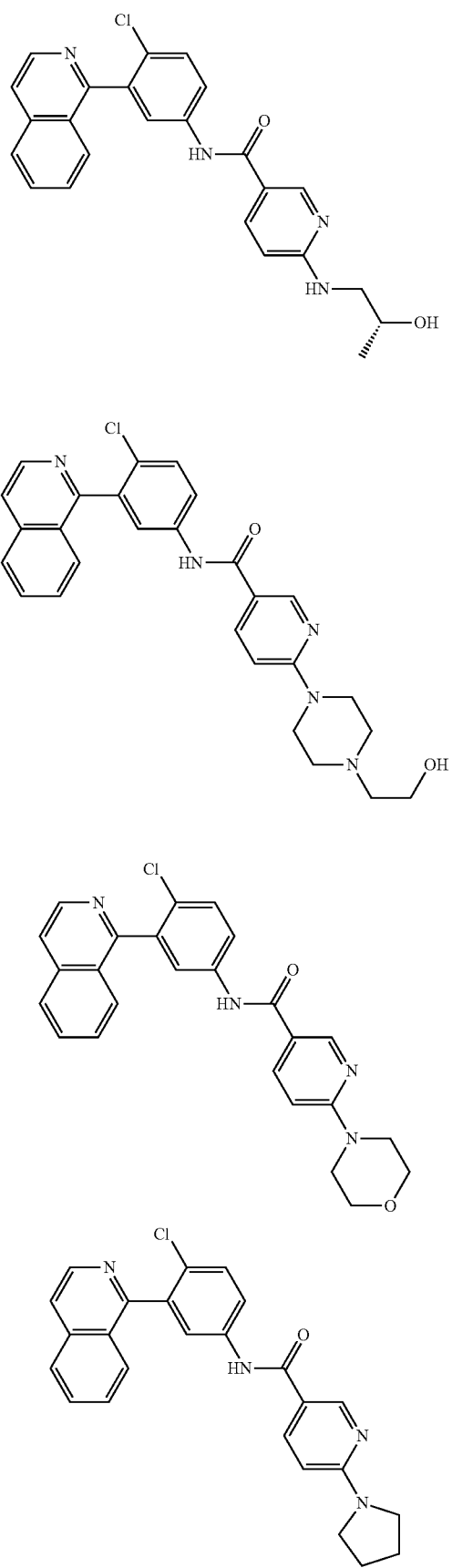

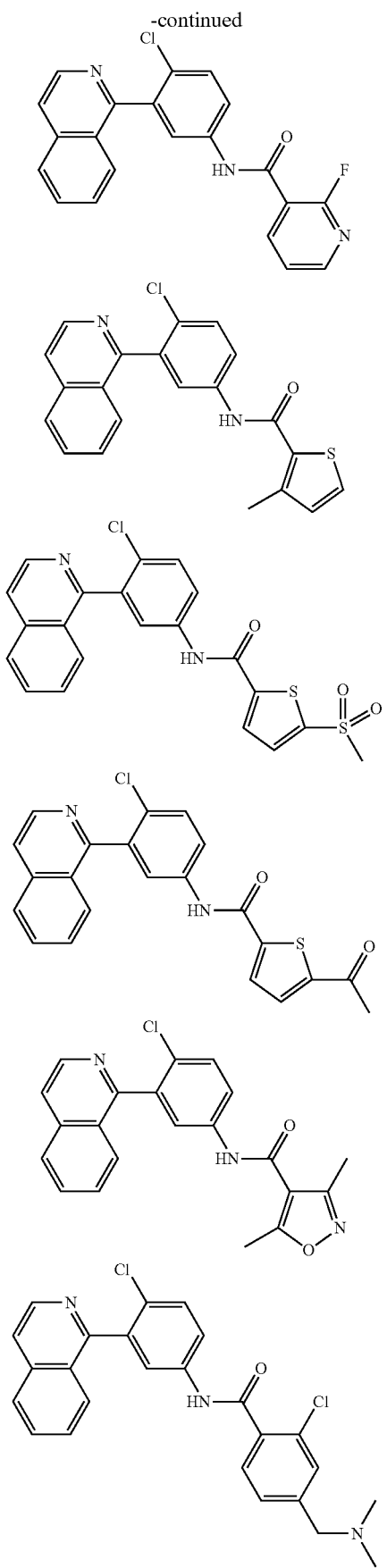
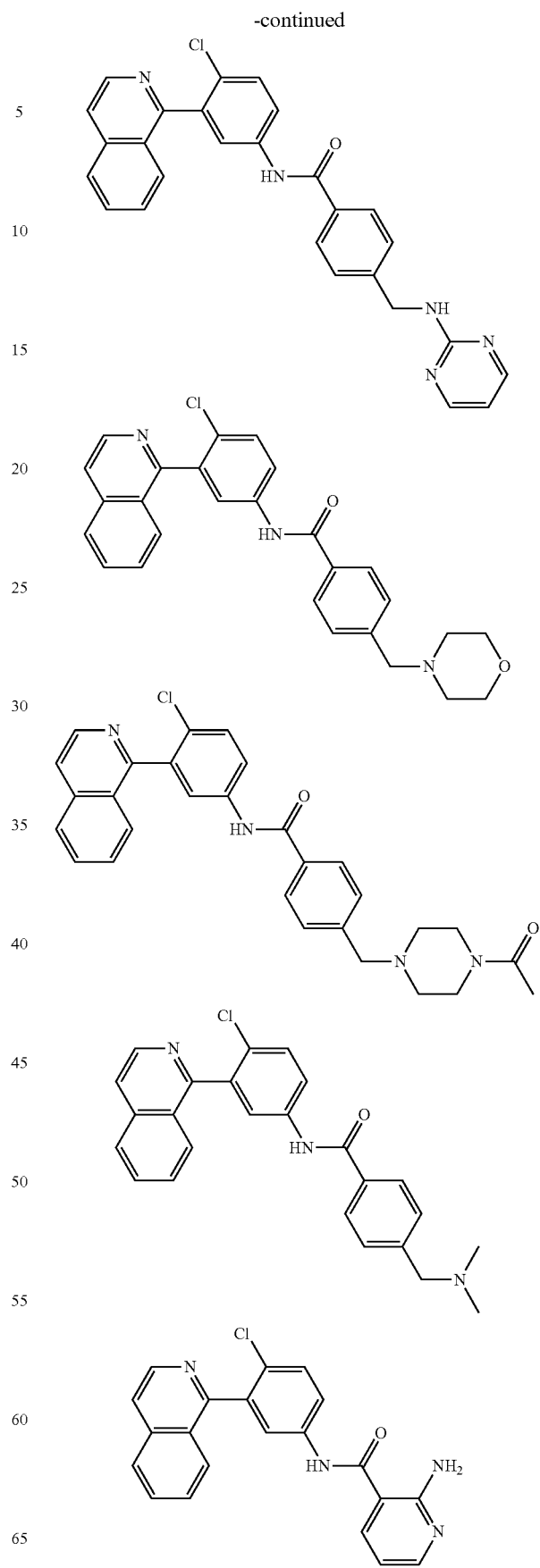

47
-continued
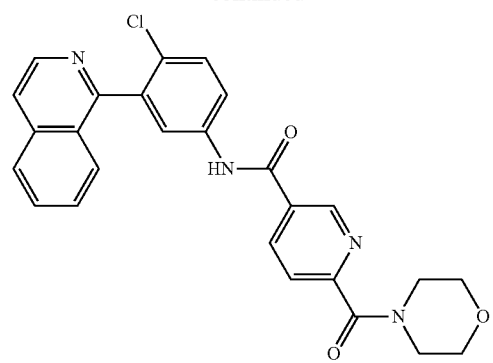
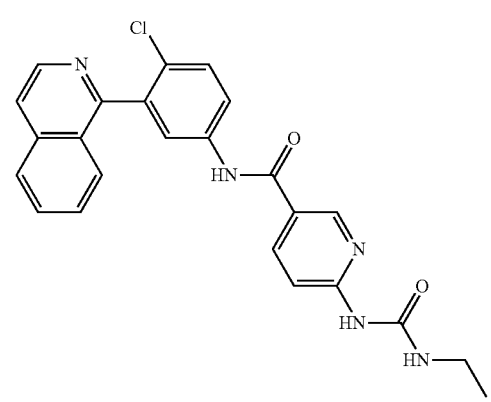
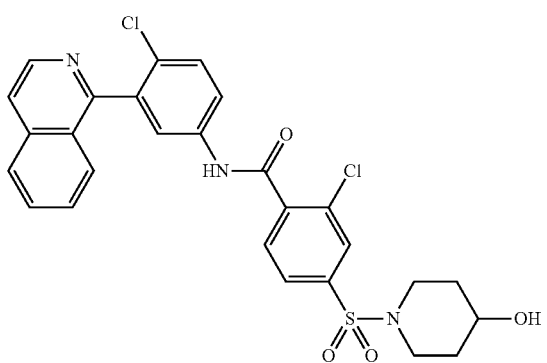
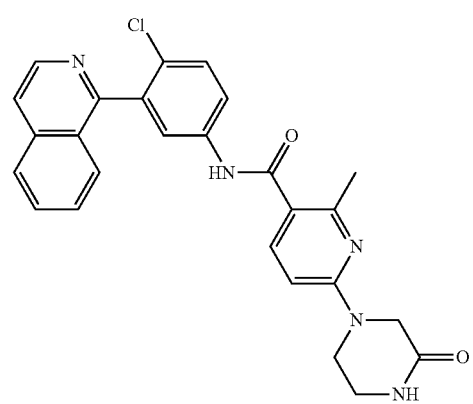
48
-continued
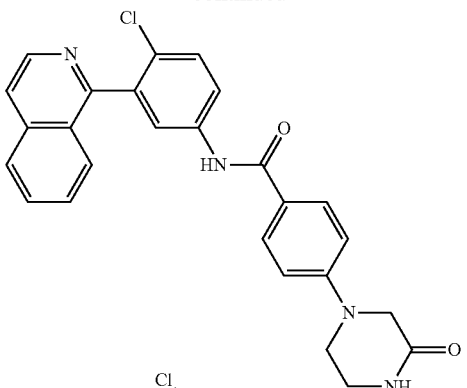
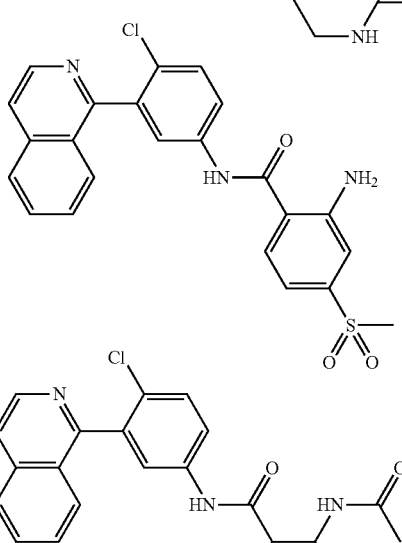
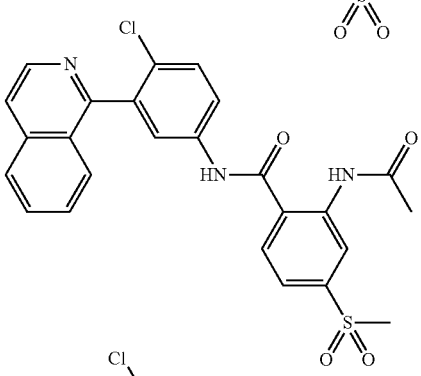
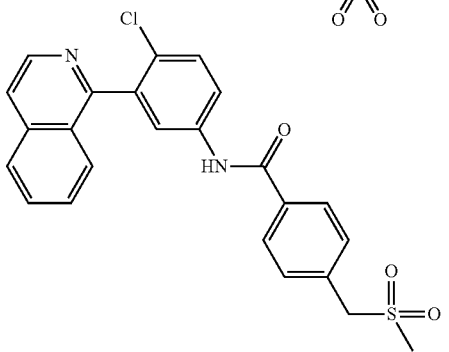
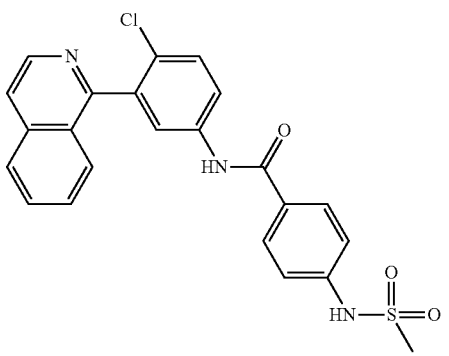

49
-continued
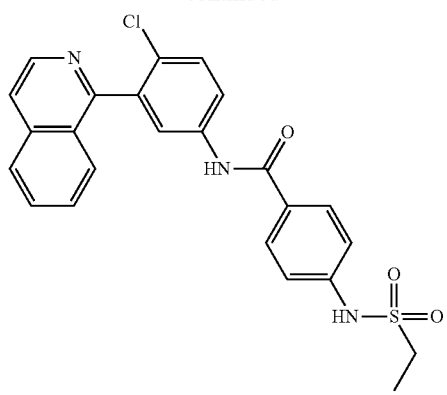
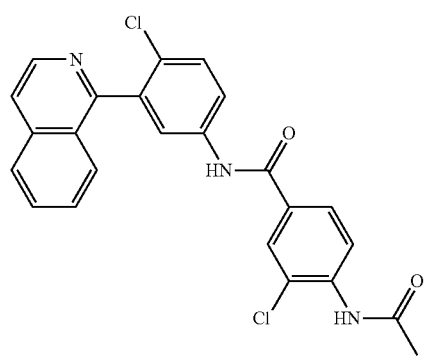
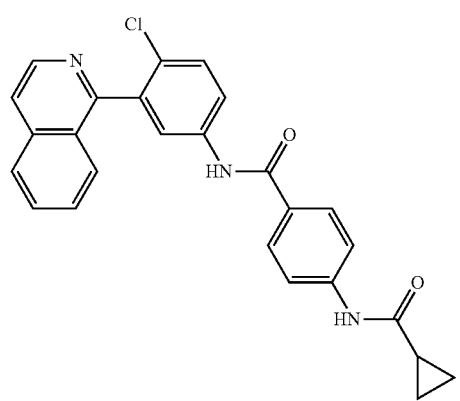
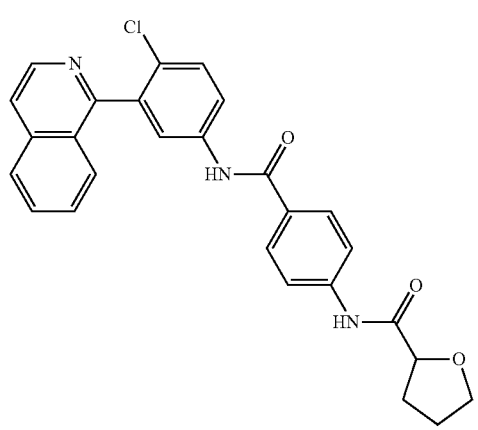
50
-continued
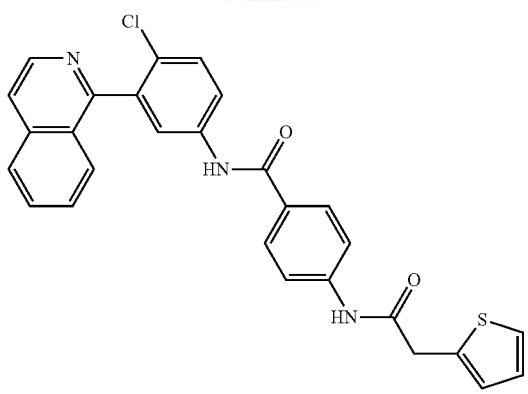
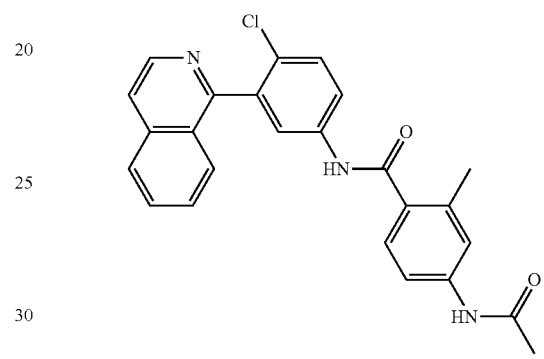
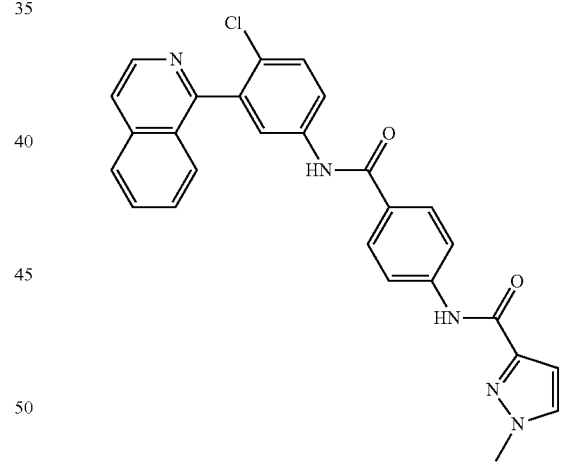
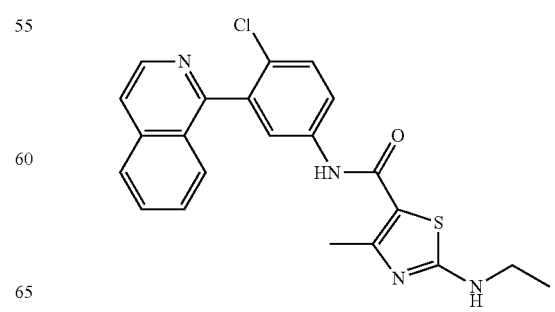

51
-continued
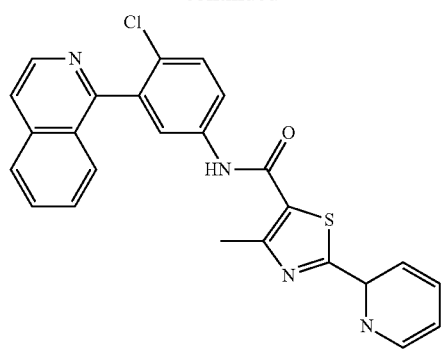
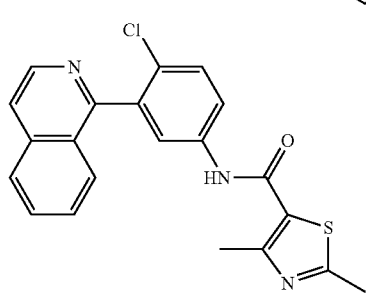
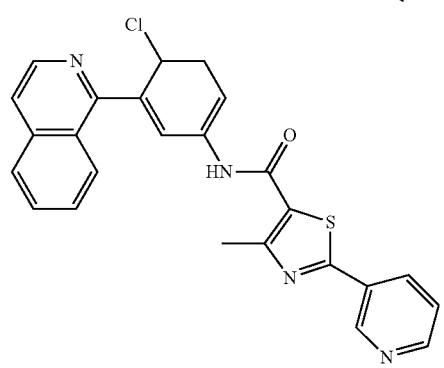
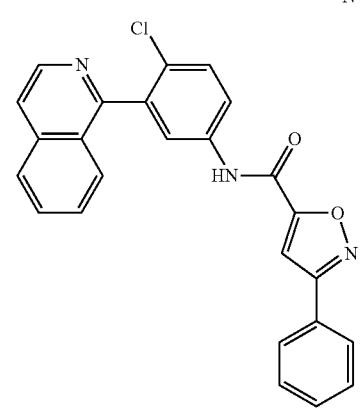
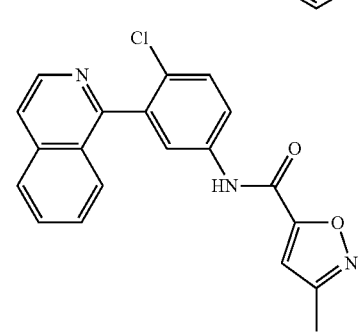
52
-continued
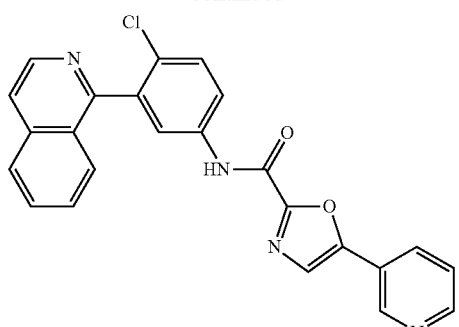
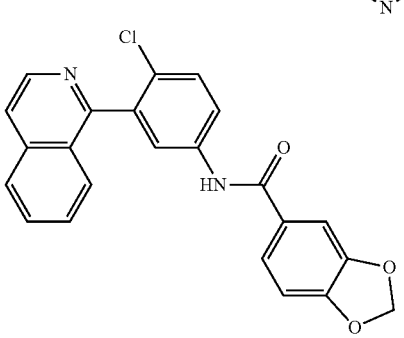
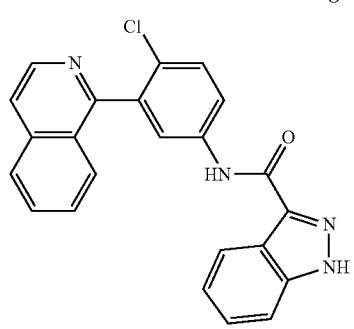
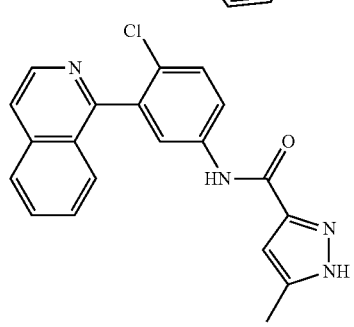
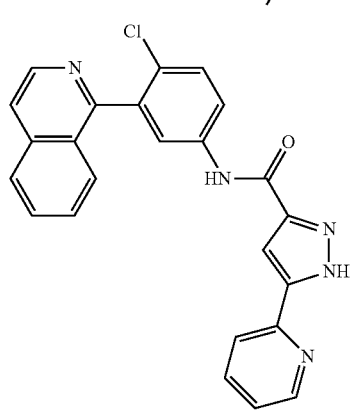

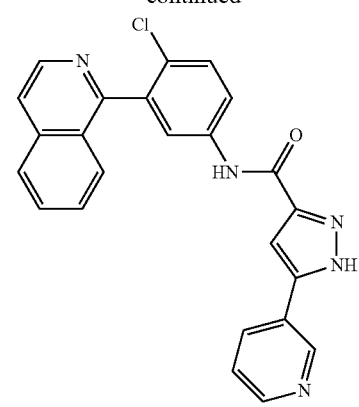
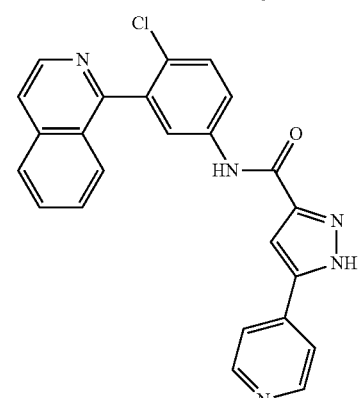
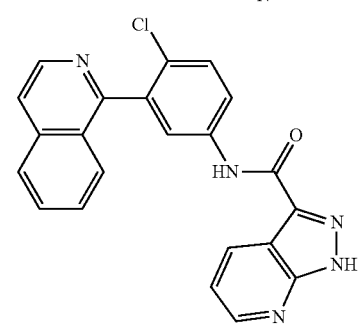
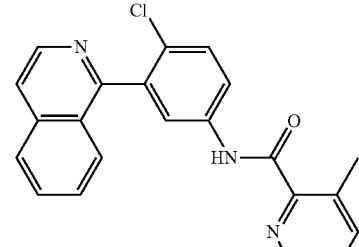
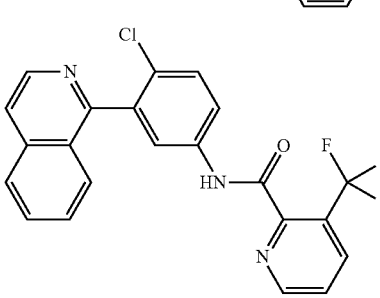
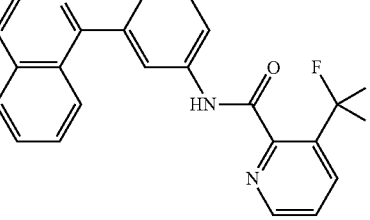
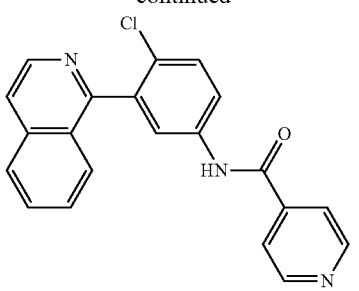
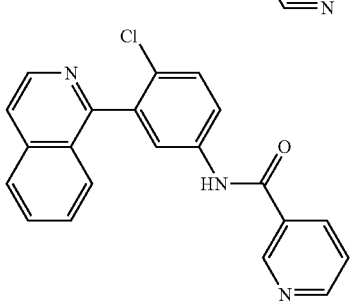
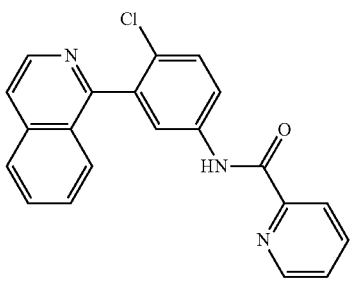
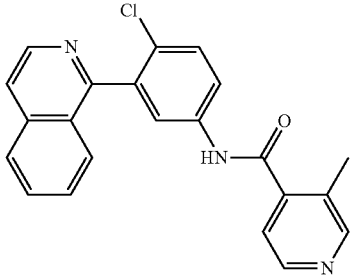
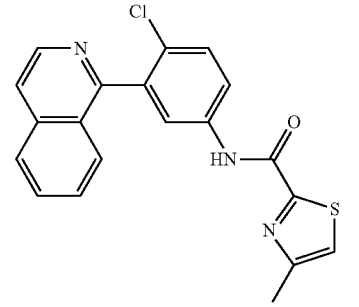
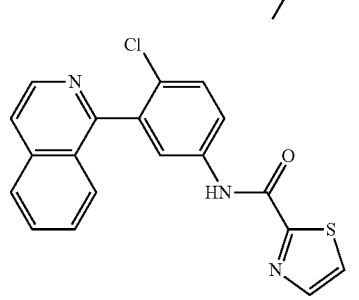

-continued
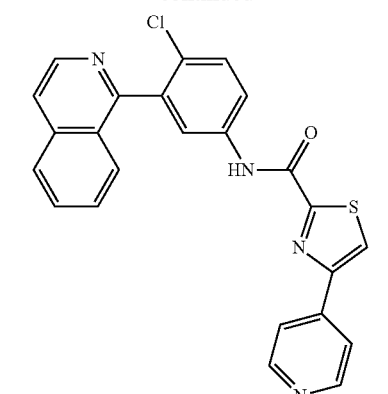
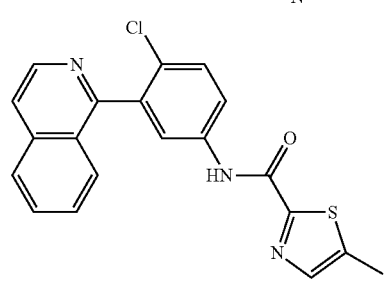
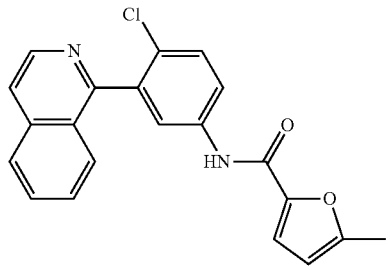
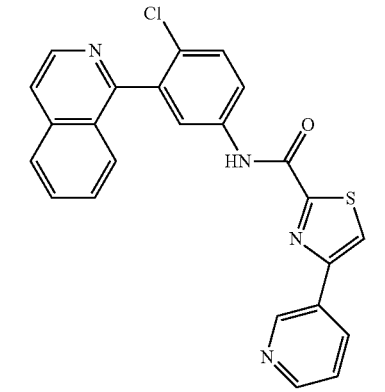
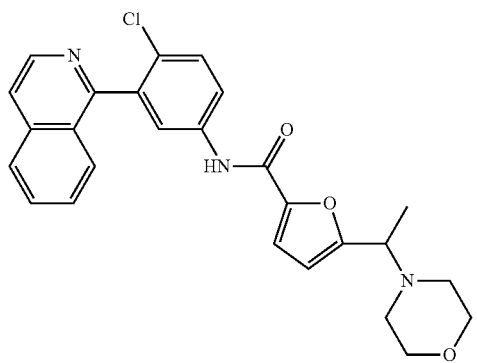
-continued
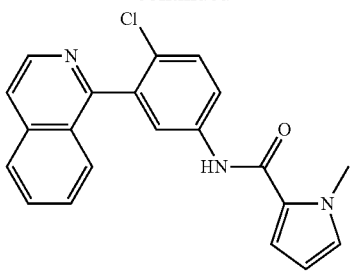
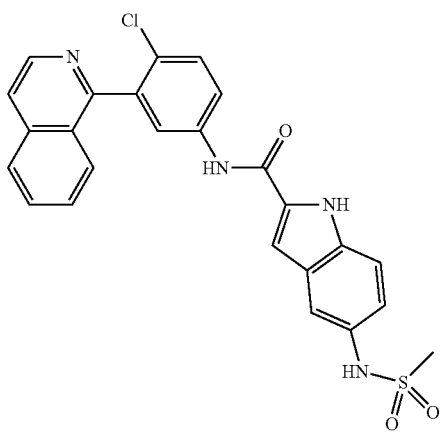
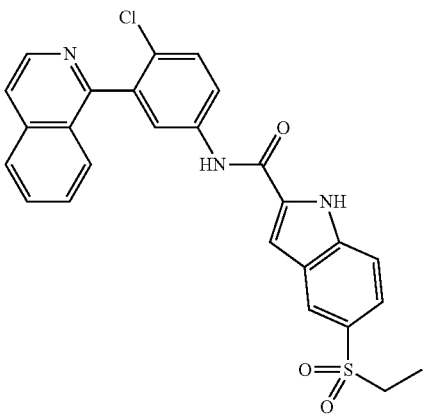
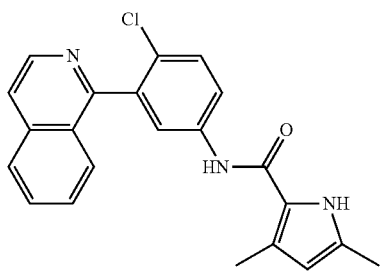
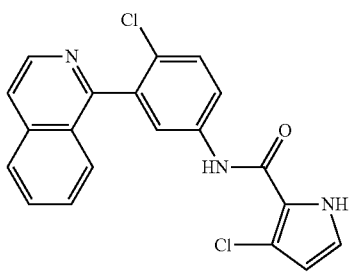

-continued
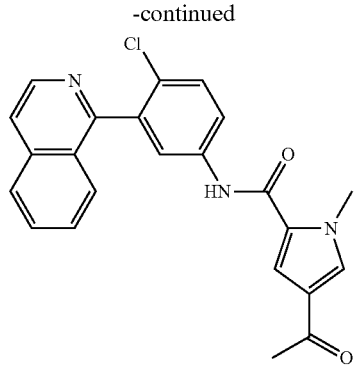
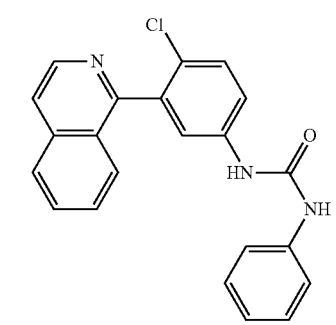
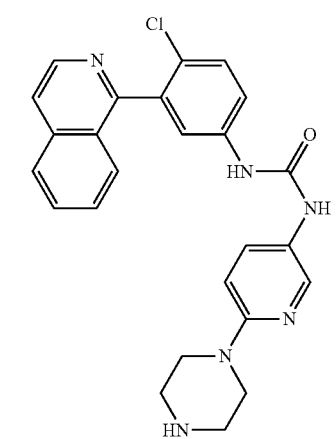
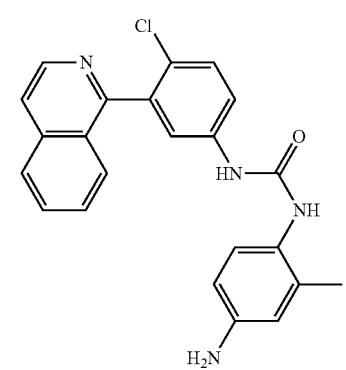
-continued
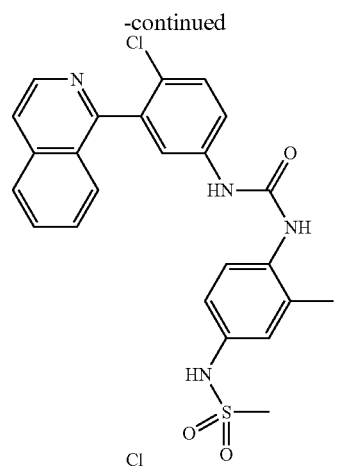
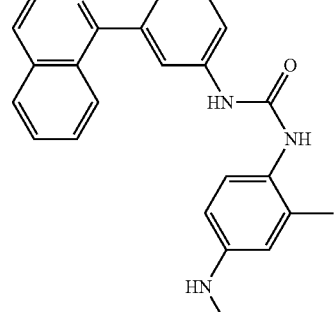
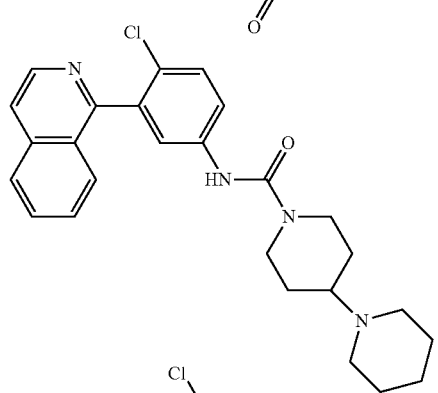
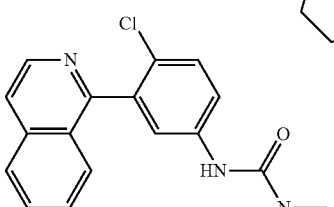
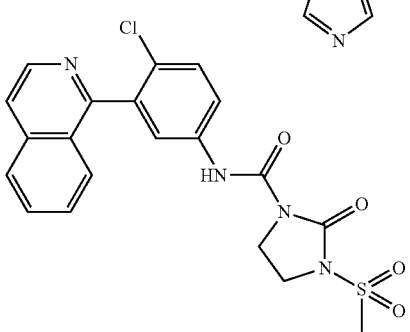

-continued
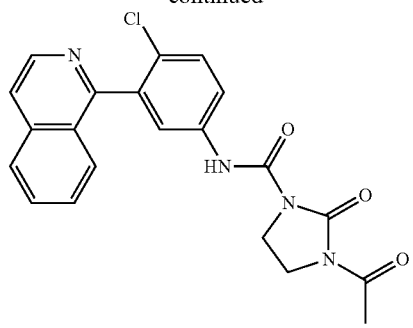
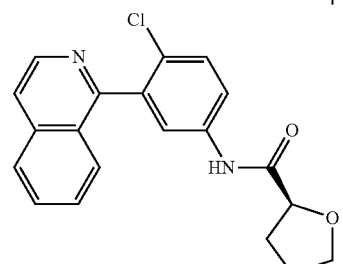
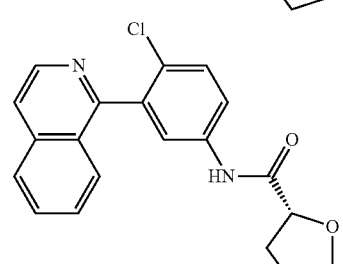
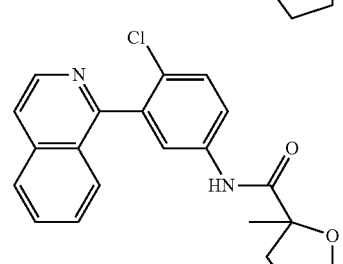
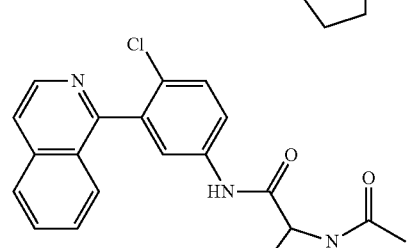
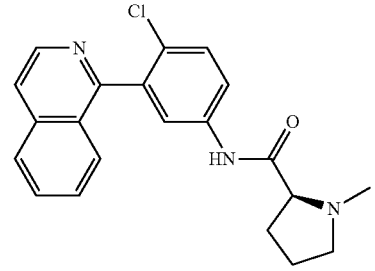
-continued
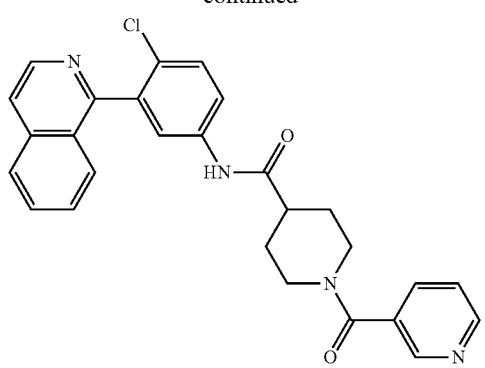
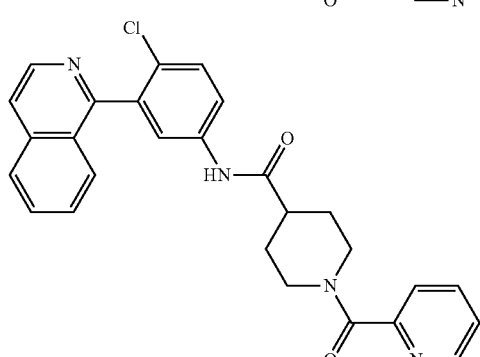
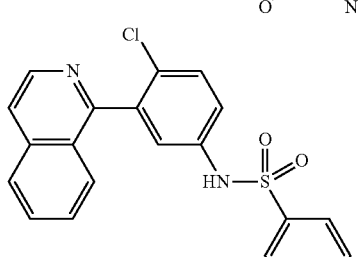
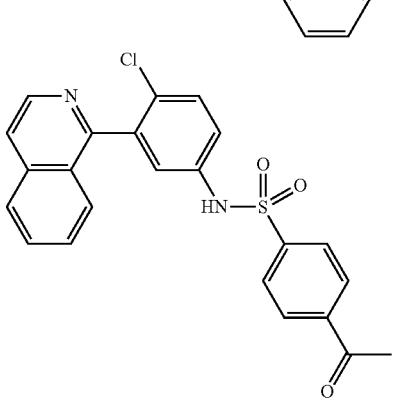
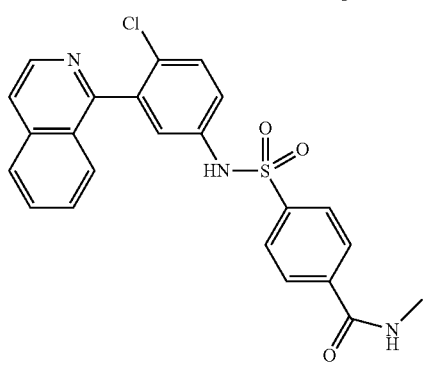

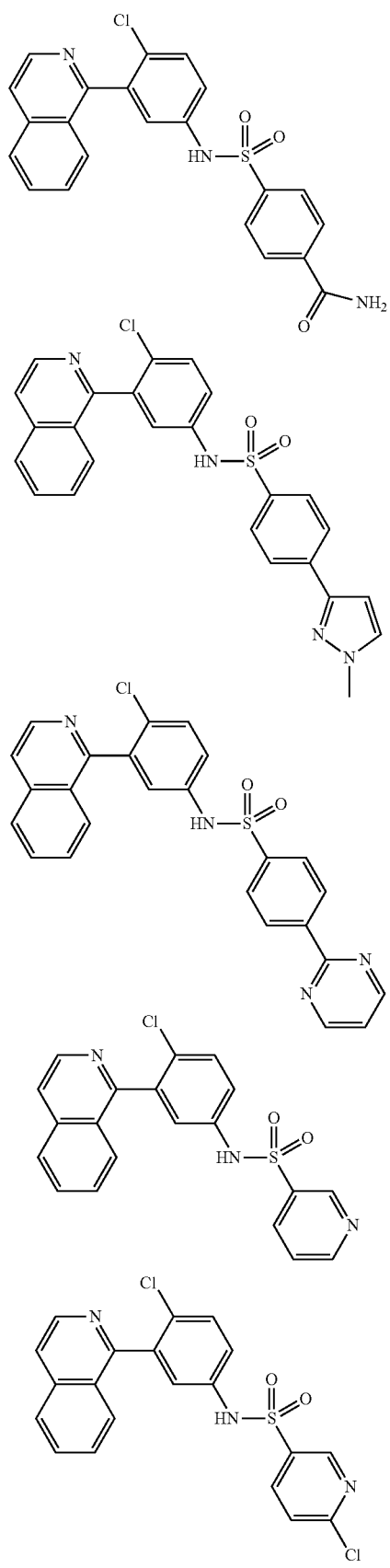
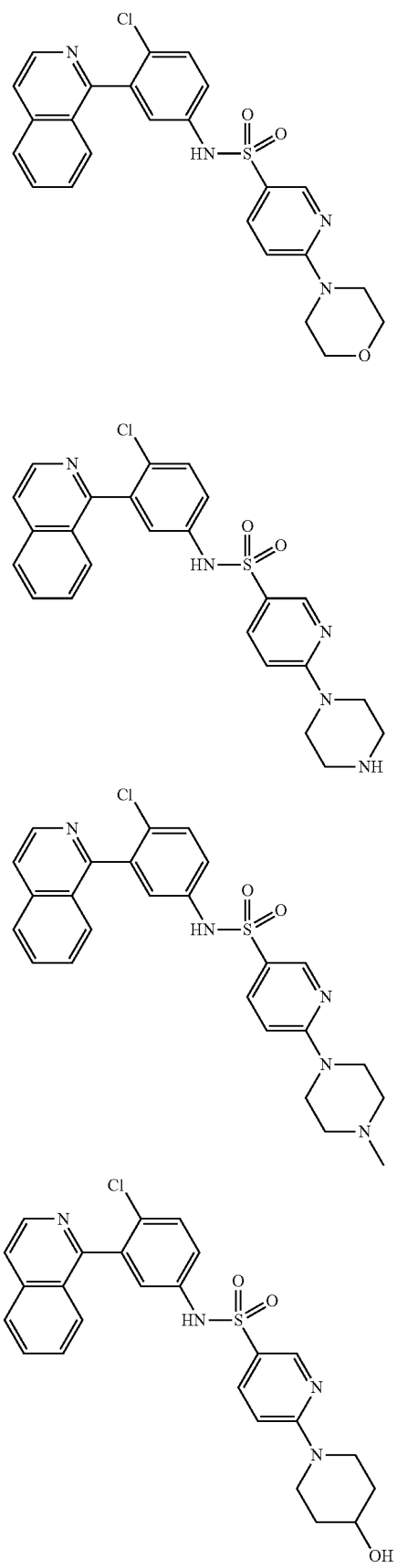

63
-continued
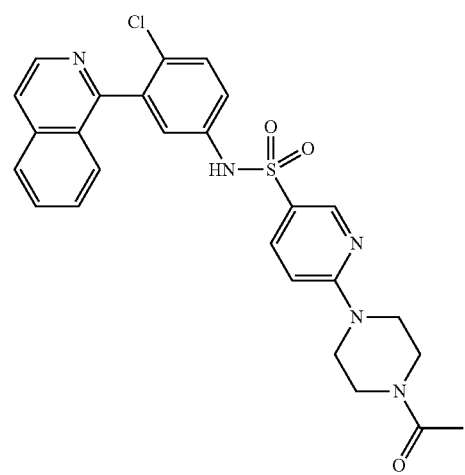
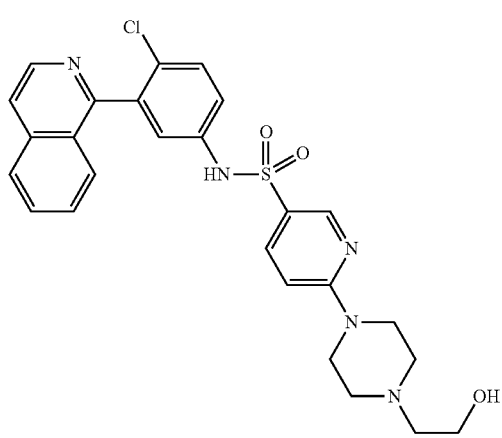
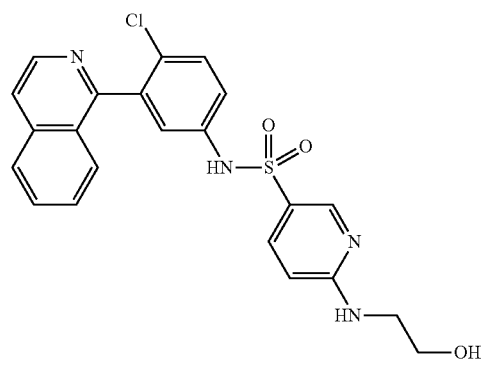
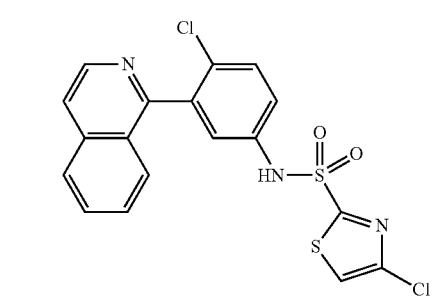
64
-continued
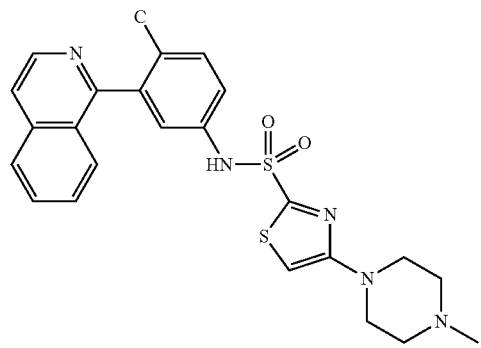
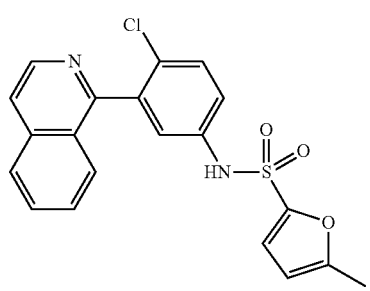
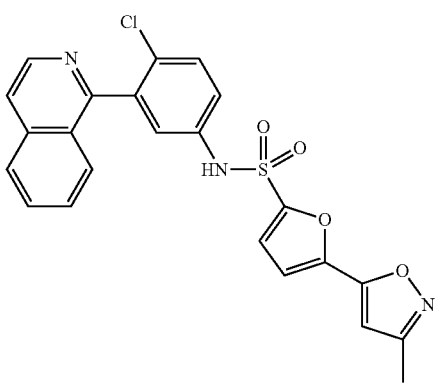
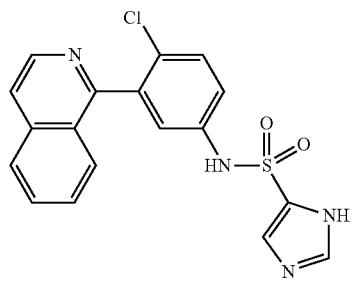
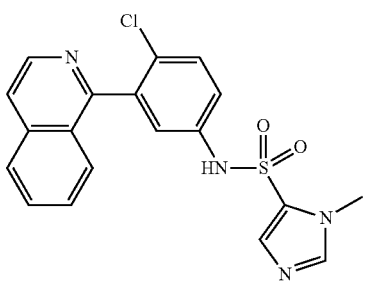

65
-continued
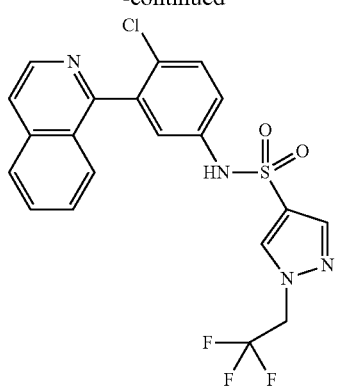
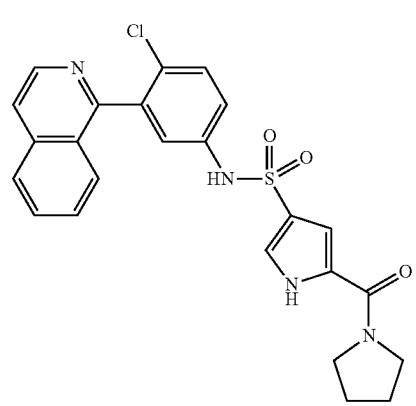
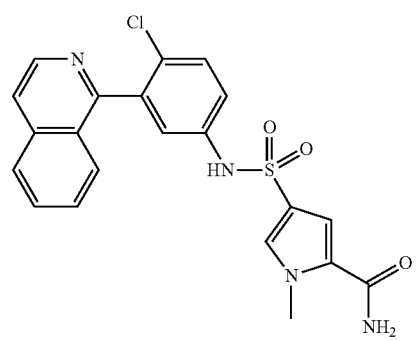
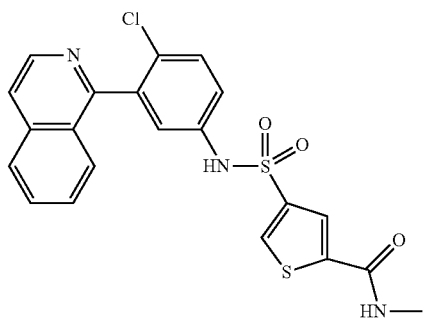
66
-continued
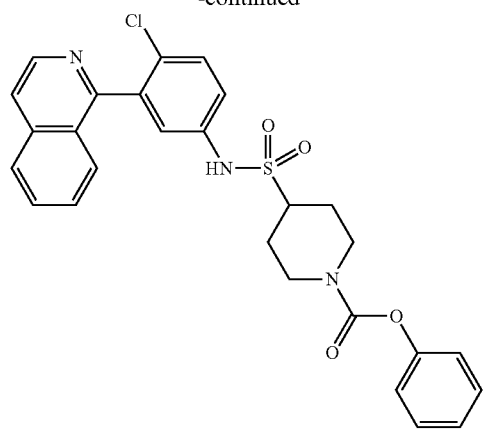
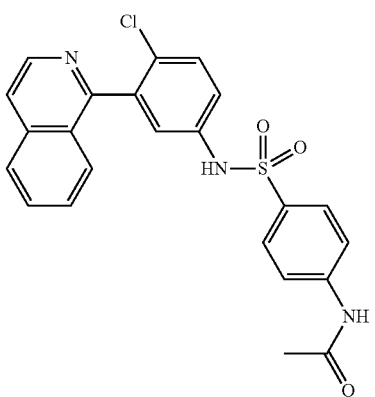
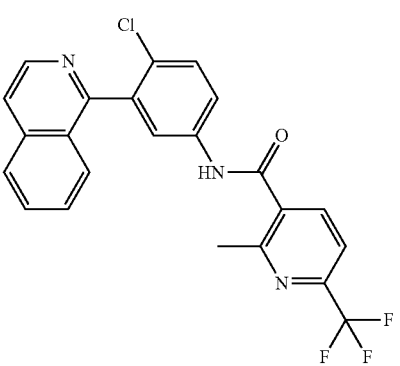
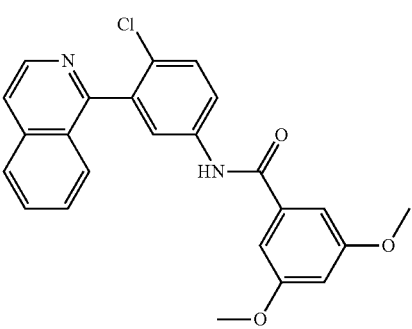

67
-continued
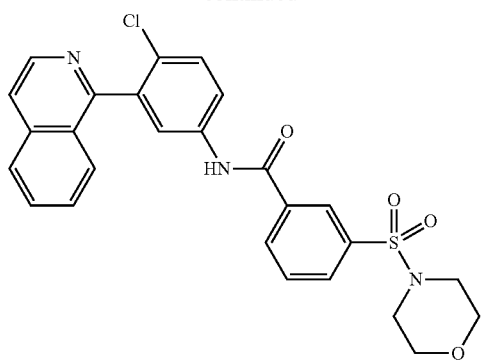
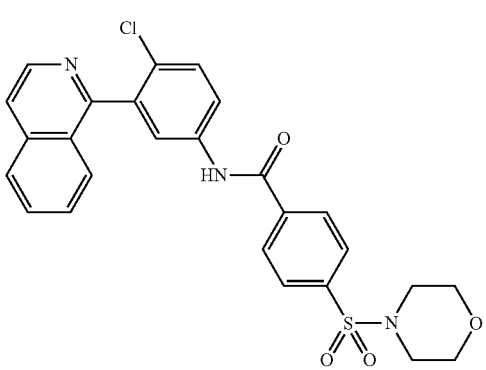
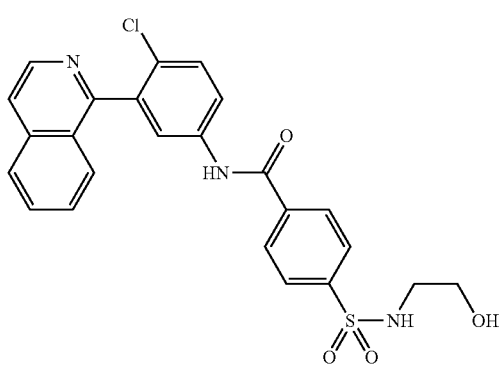
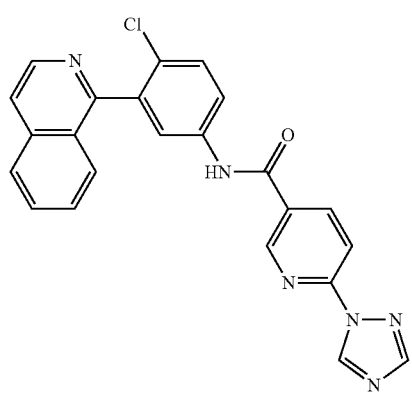
68
-continued
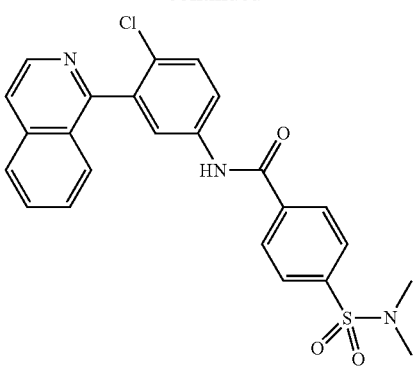
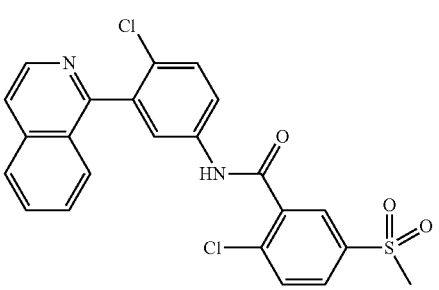
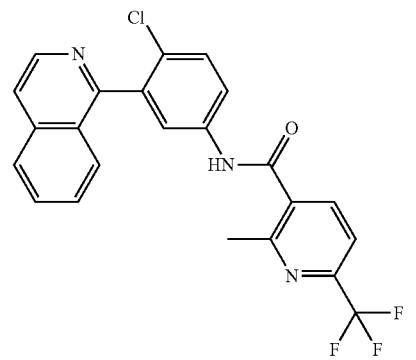
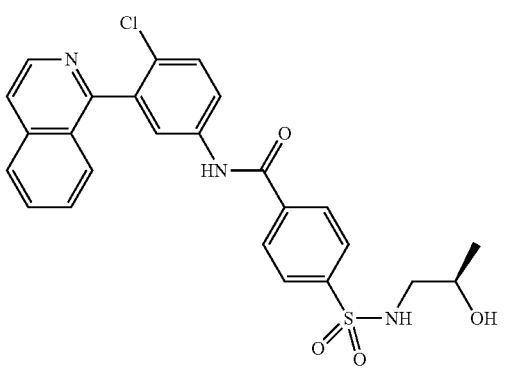

69
-continued
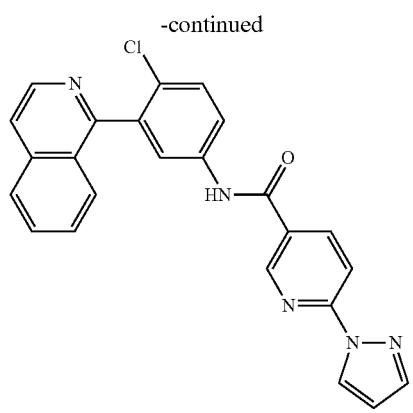
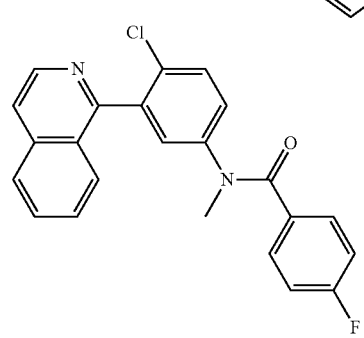
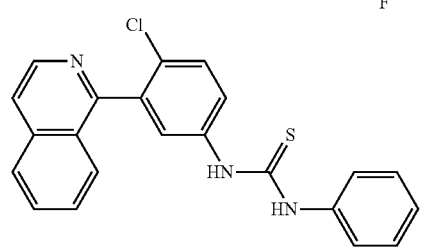
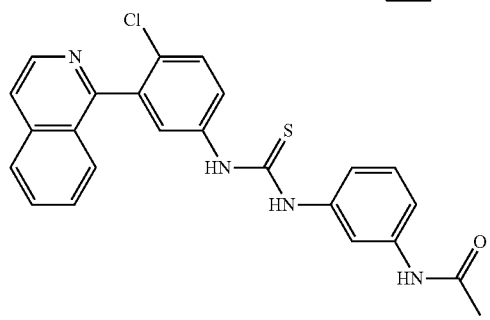
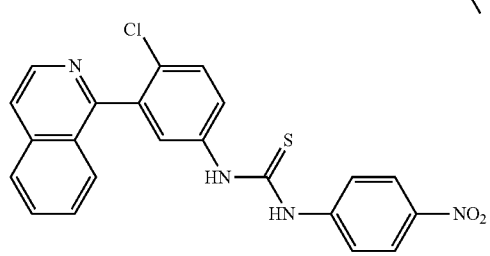
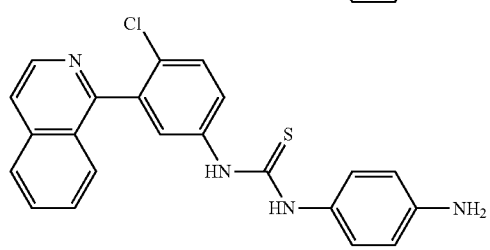
70
-continued
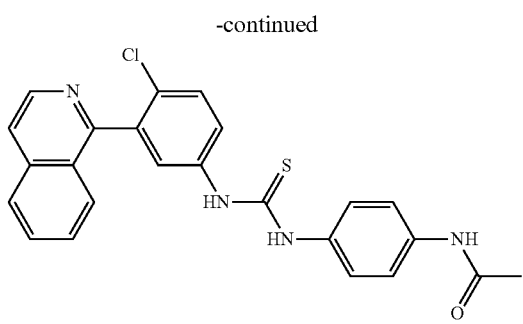
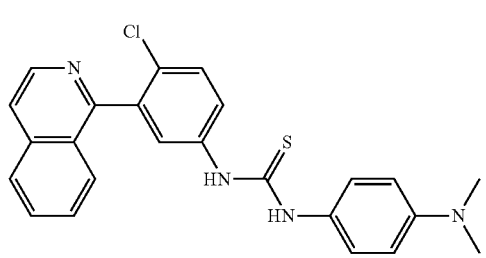
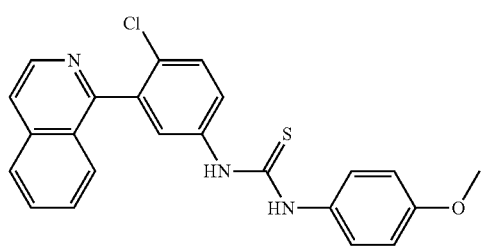
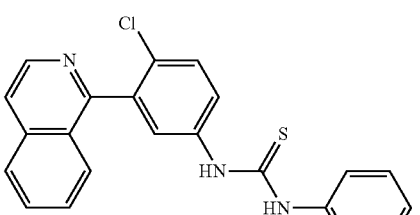
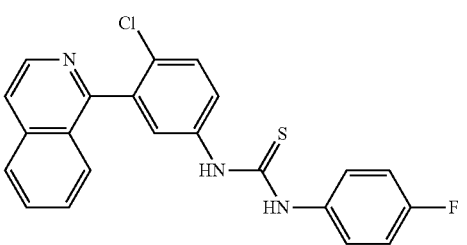
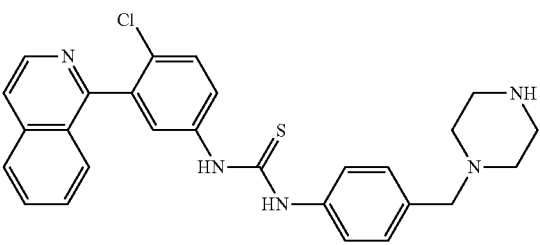

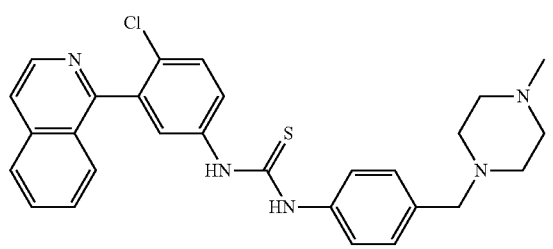
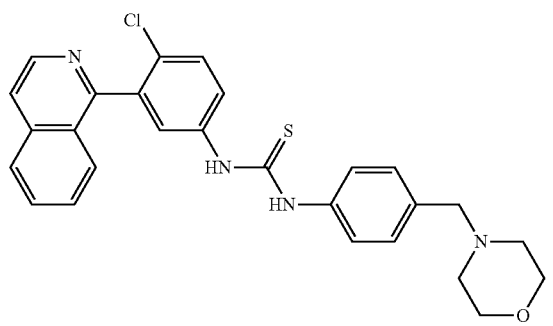
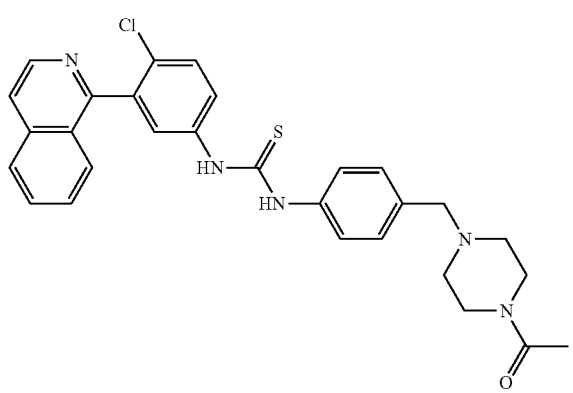
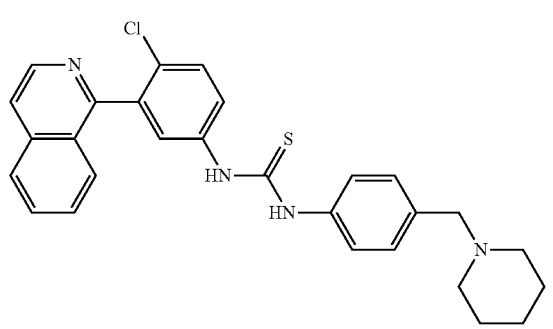
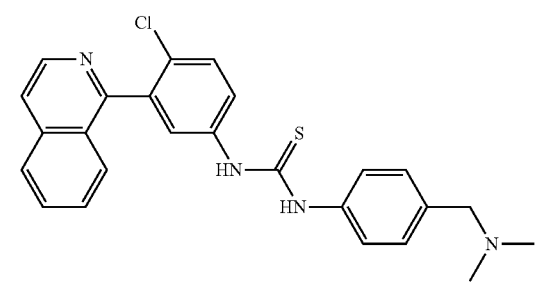
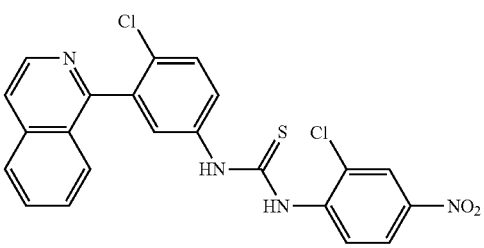
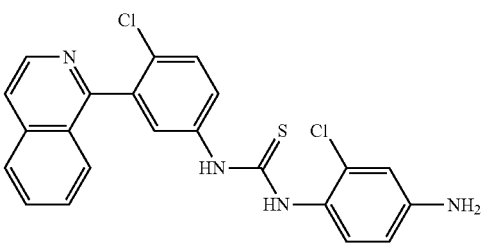
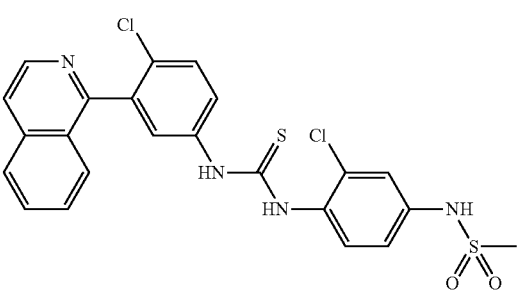
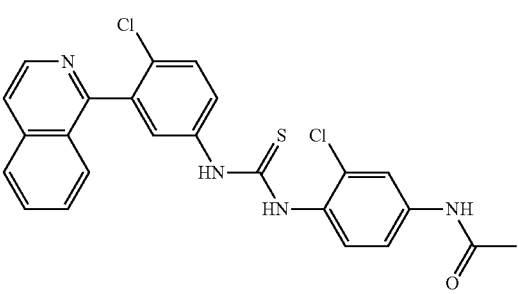
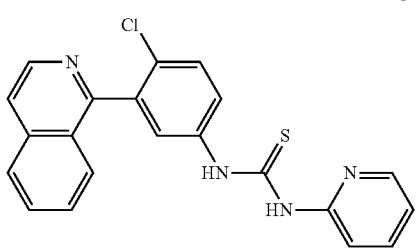
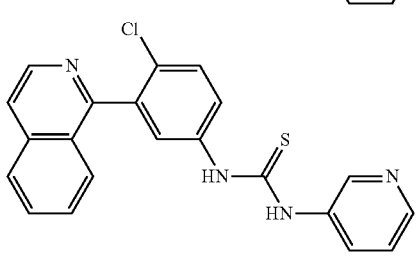
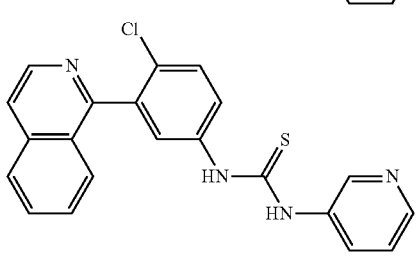

-continued
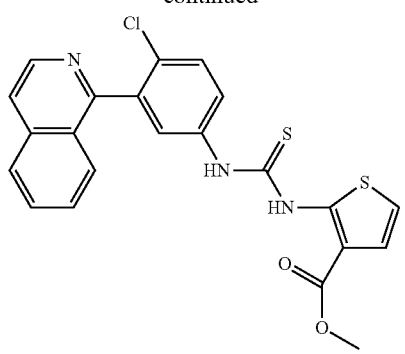
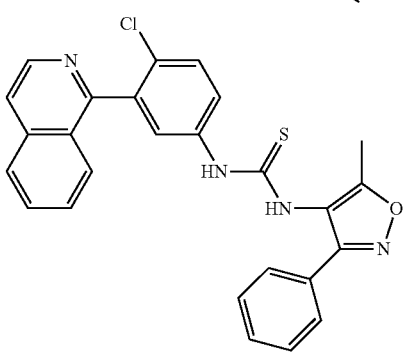
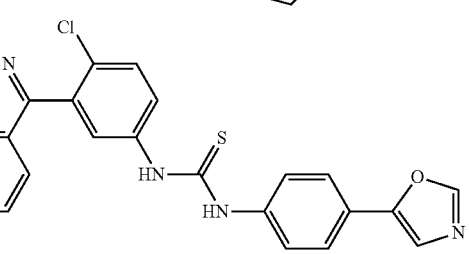
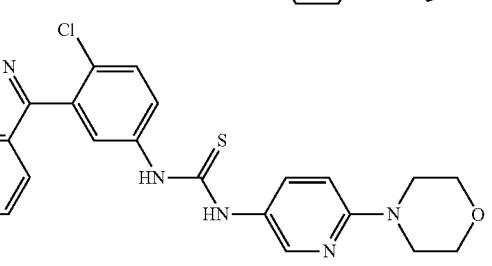
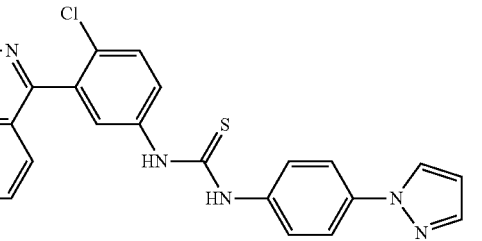
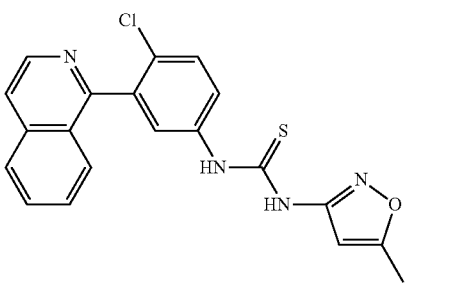
-continued
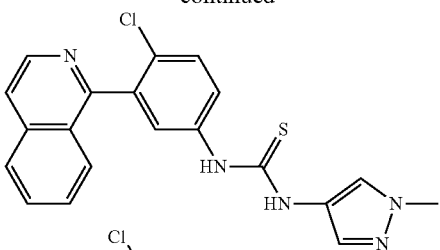
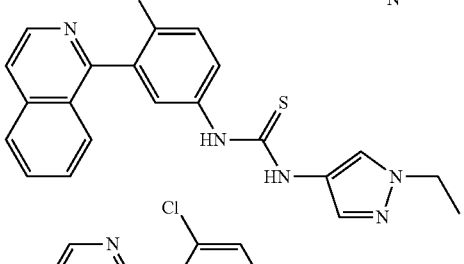
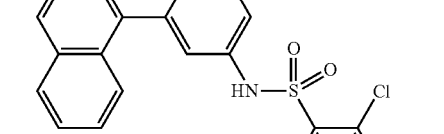
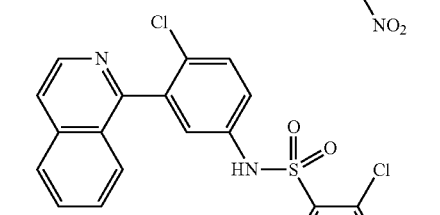
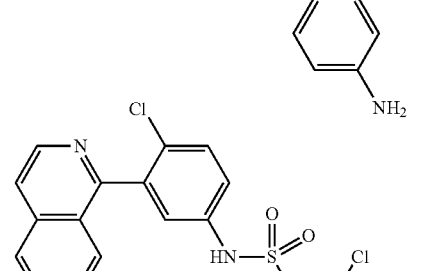
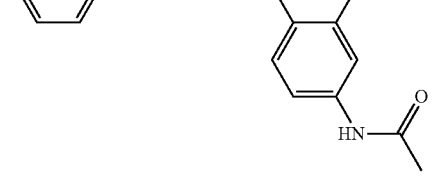
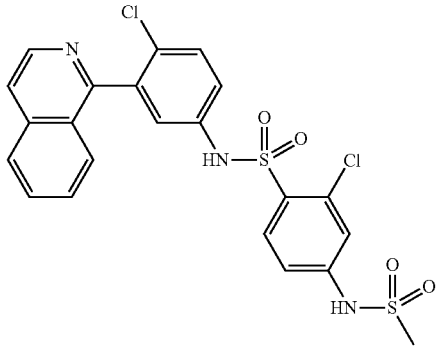

75
-continued
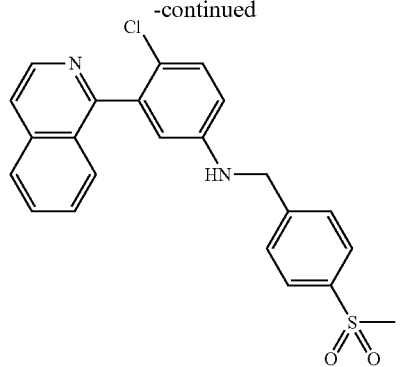
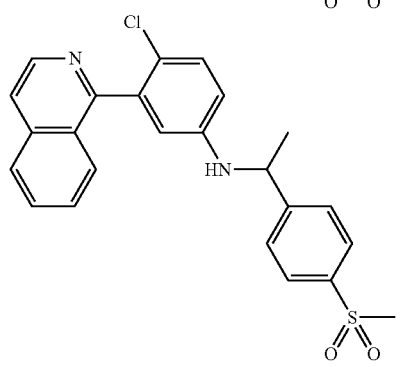
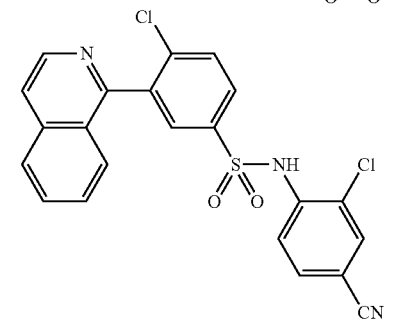
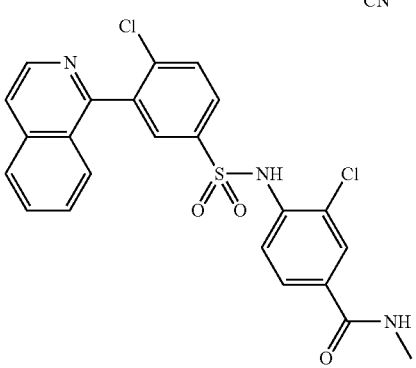
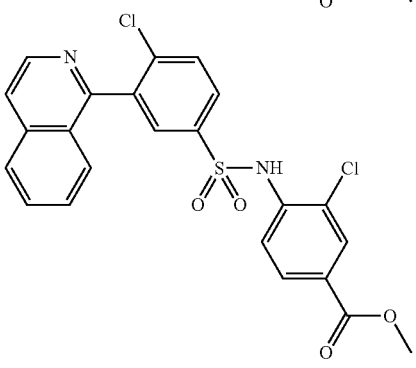
76
-continued
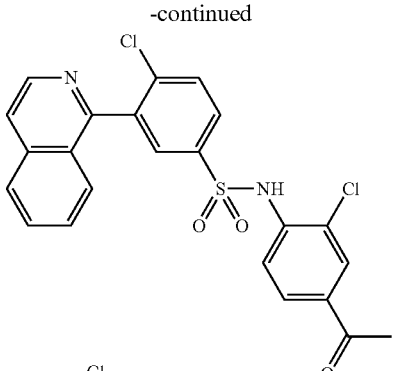
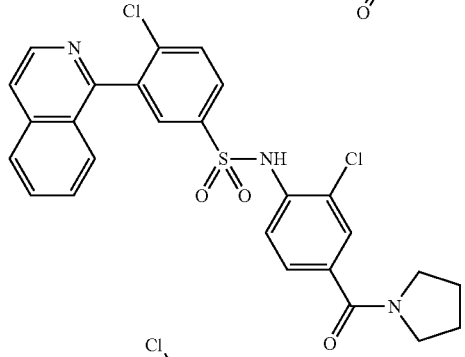
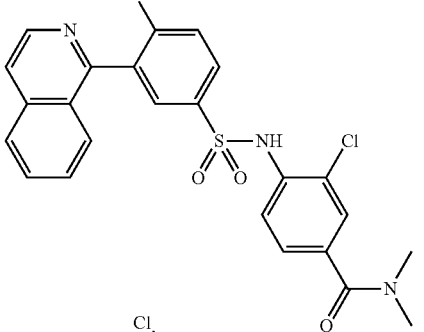
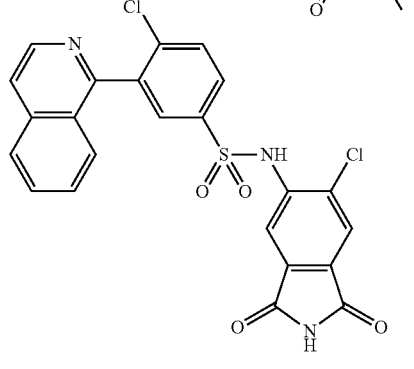
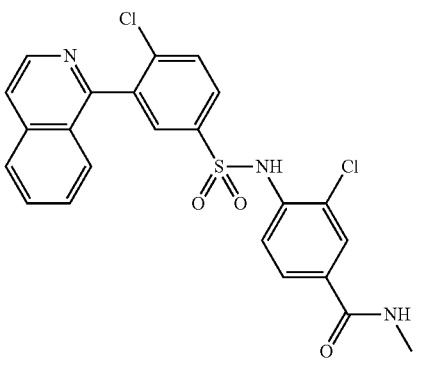

| 77 | 78 |
|---|---|
| -continued | -continued |
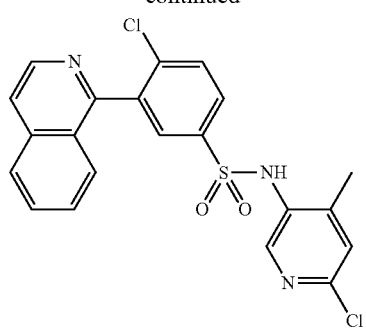
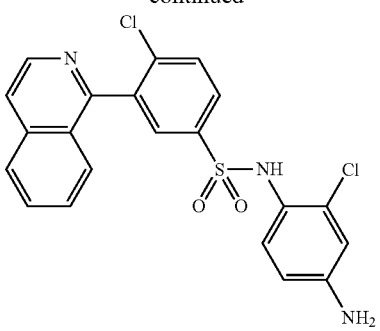
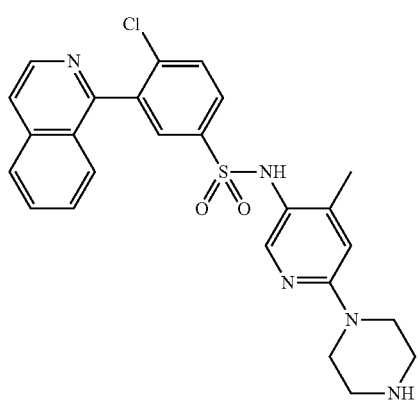
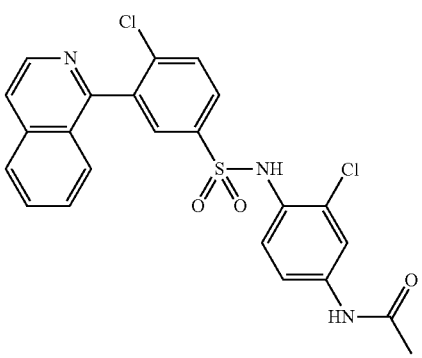
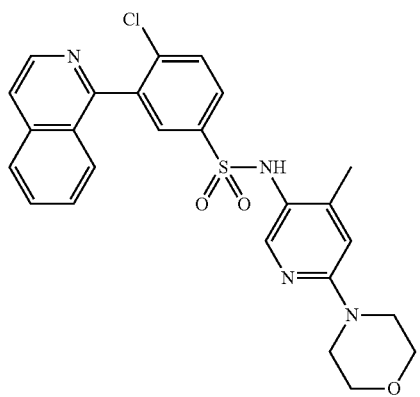
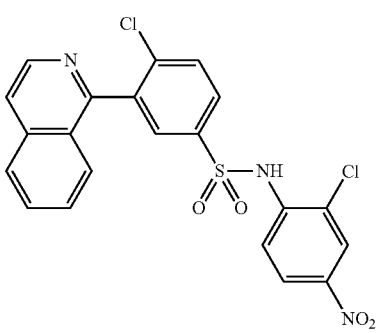
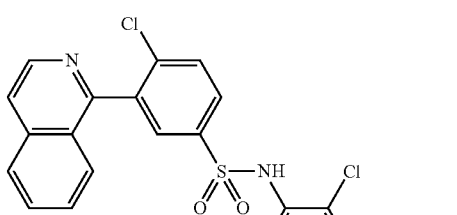
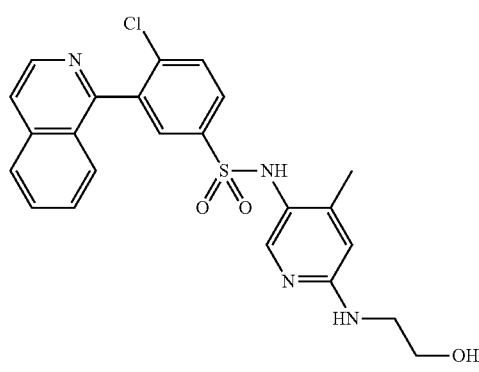
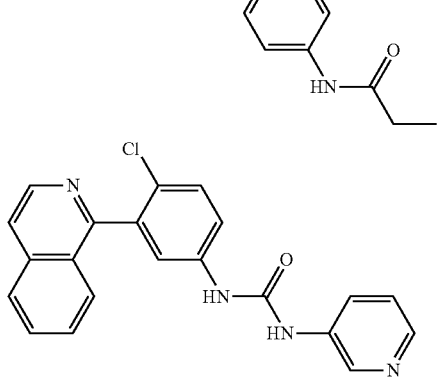

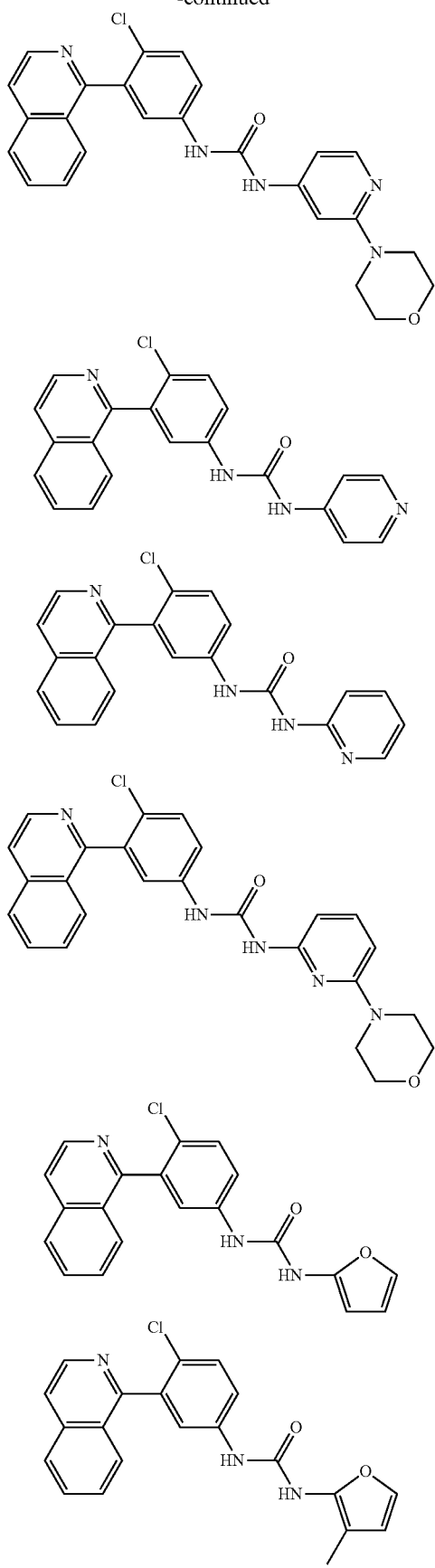
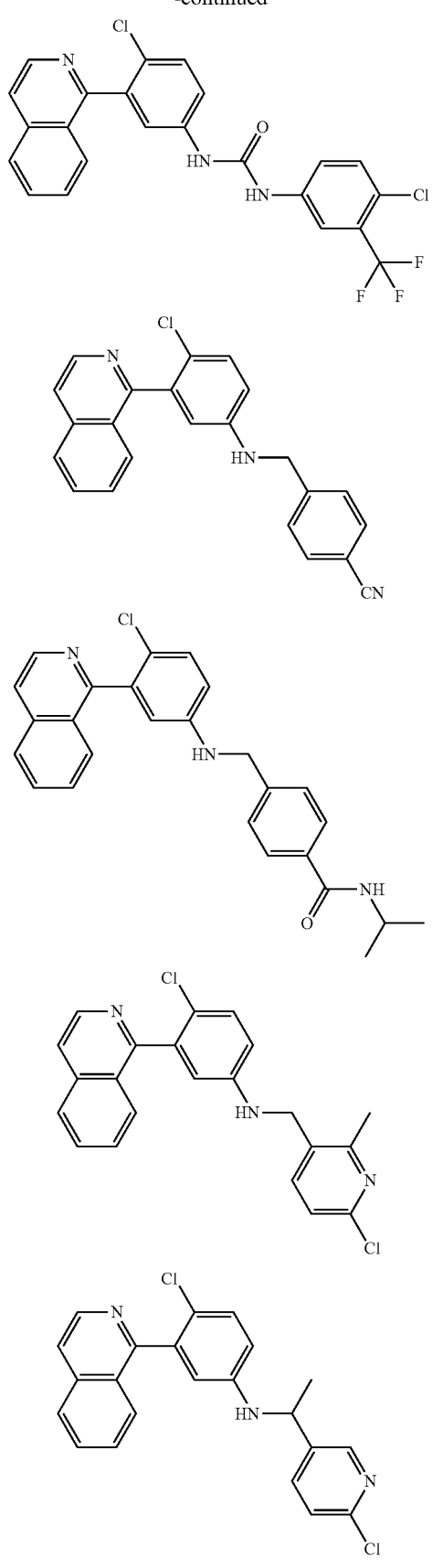

-continued
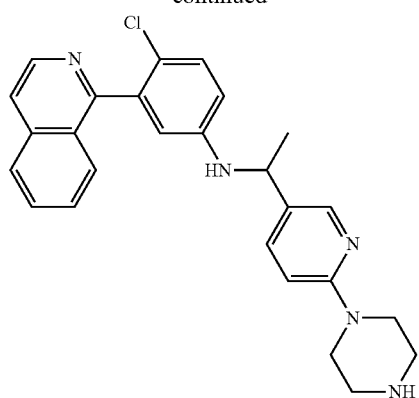
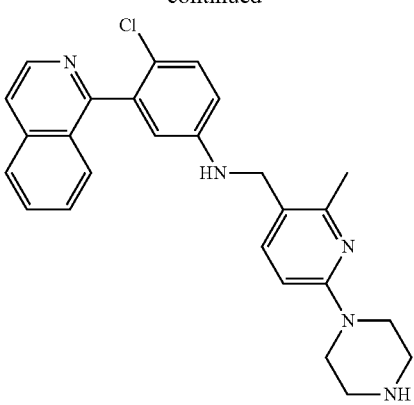
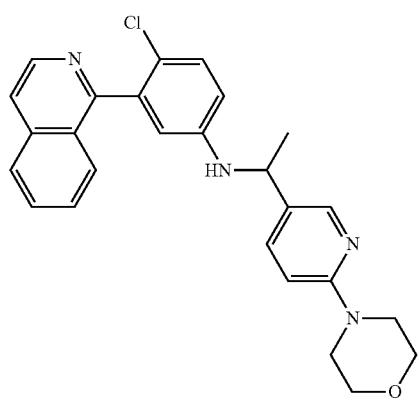
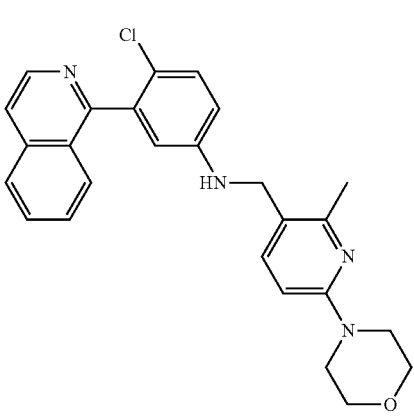
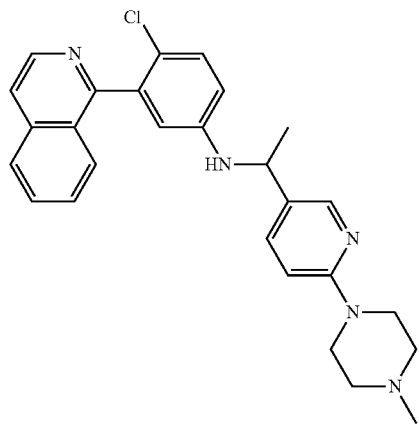
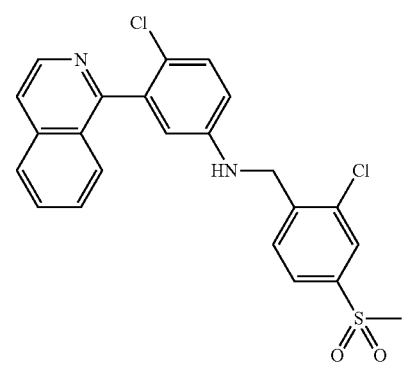
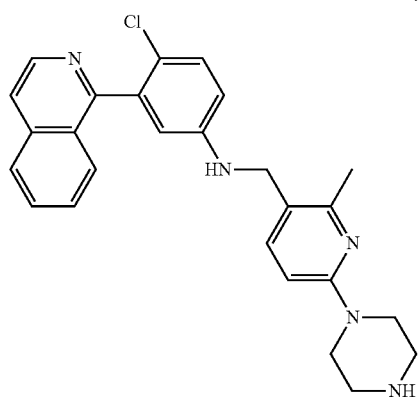
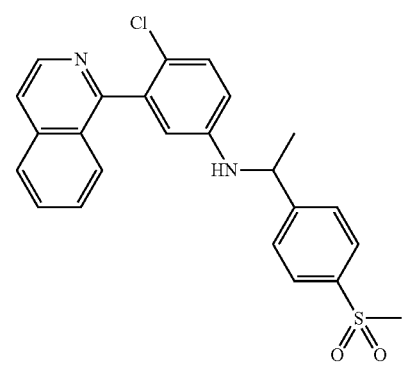

-continued
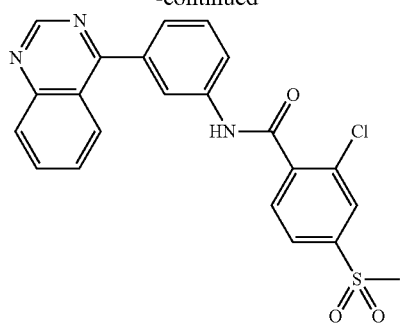
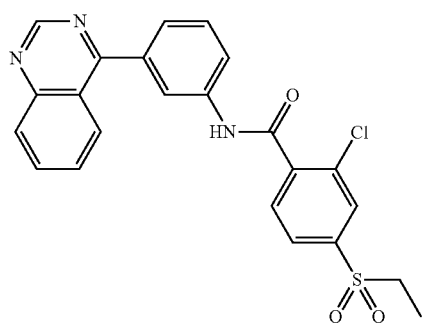
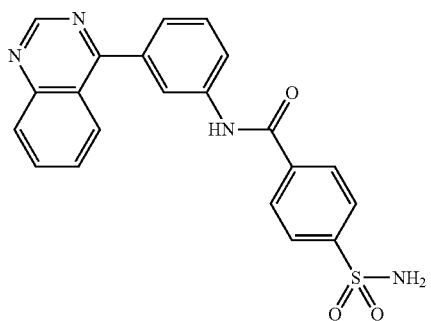
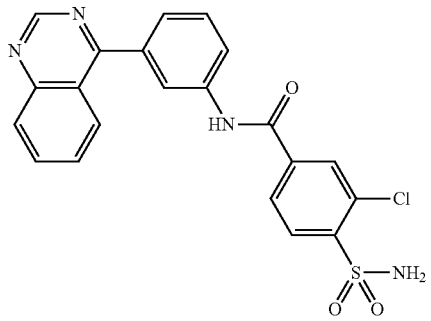
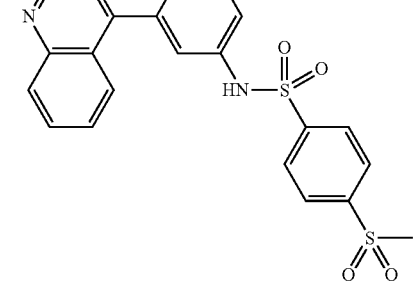
-continued
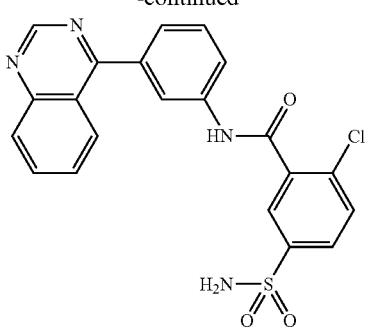
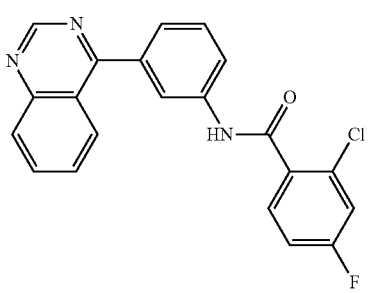
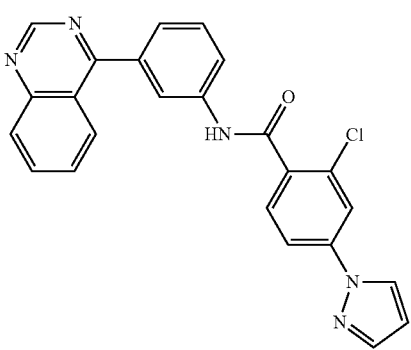
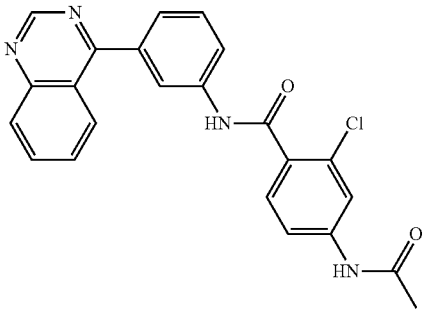
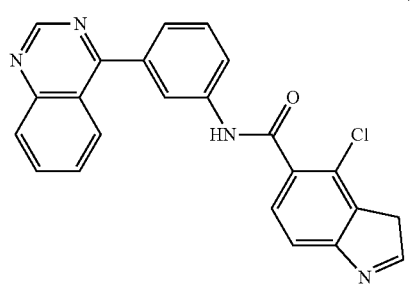

85
-continued
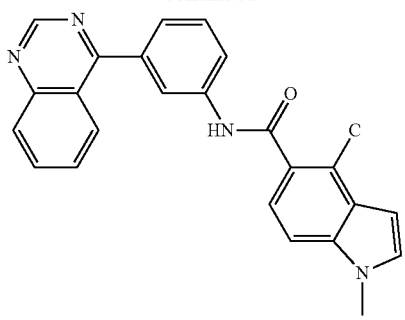
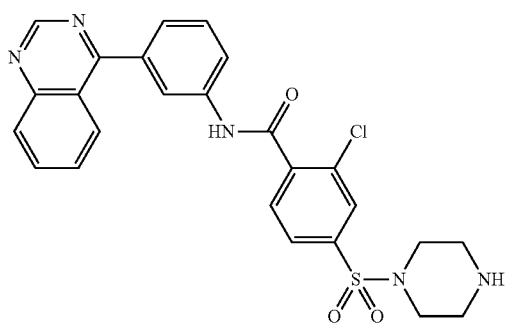
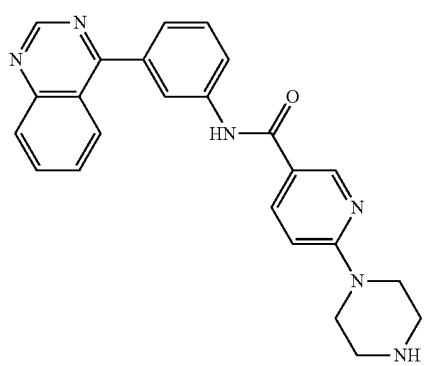
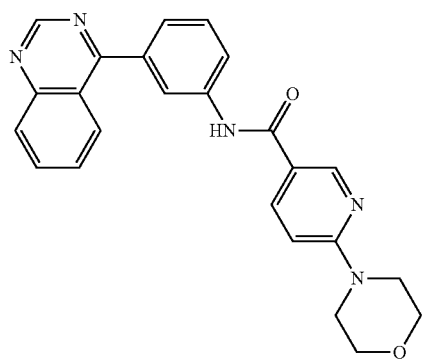
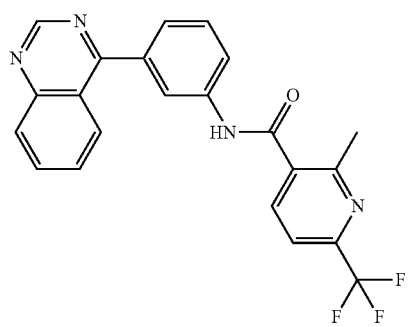
86
-continued
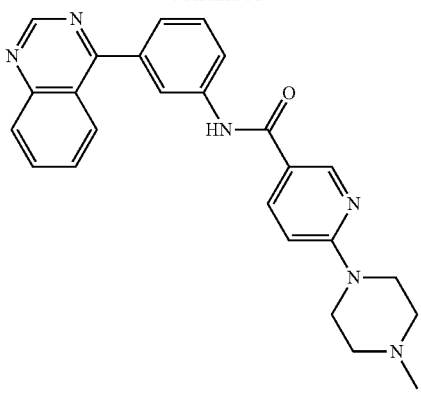
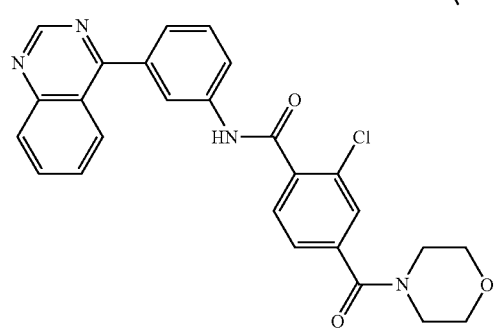
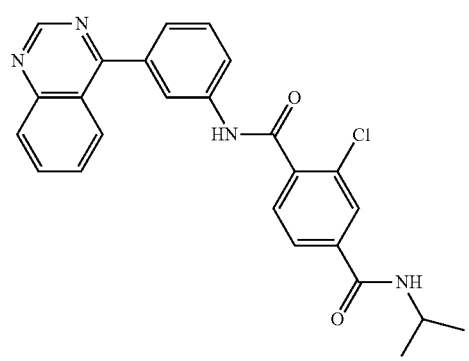
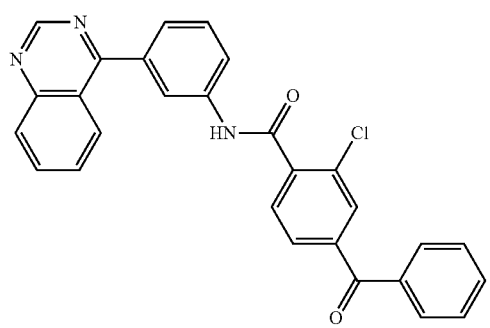
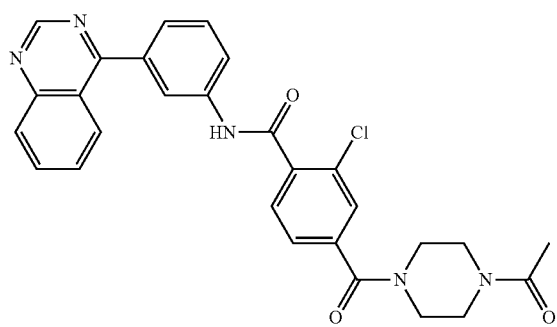

-continued
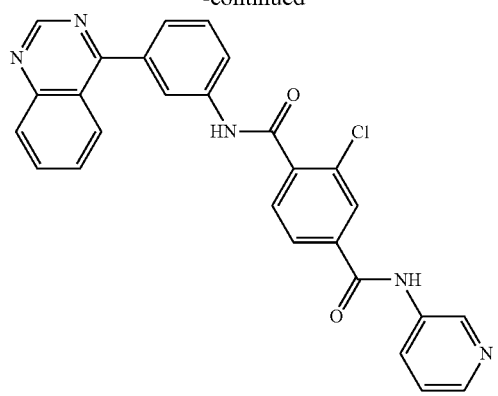
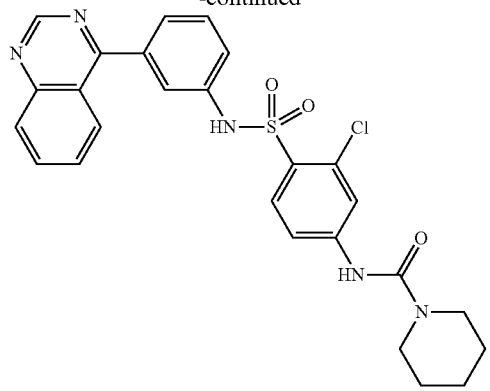
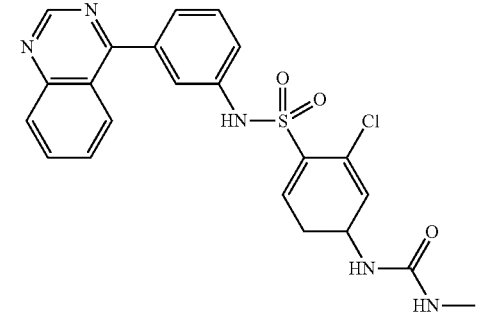
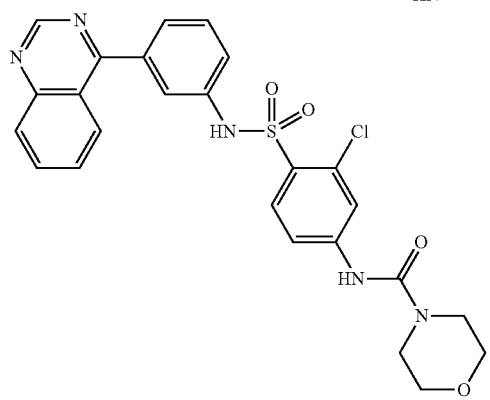
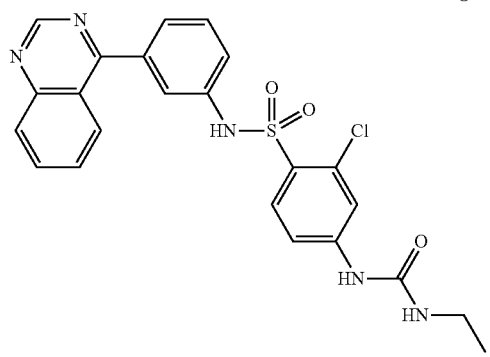
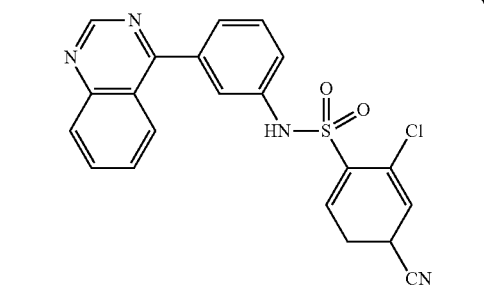

89
-continued
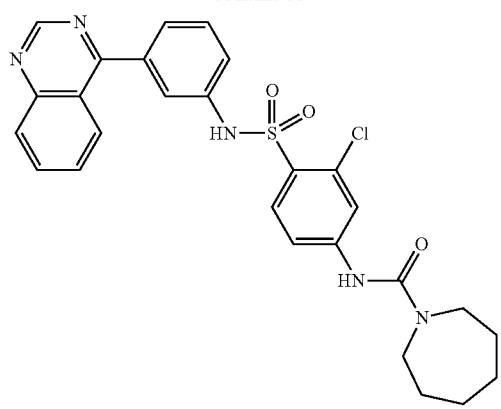
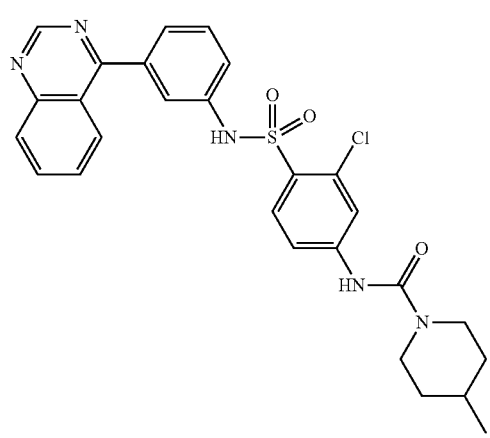
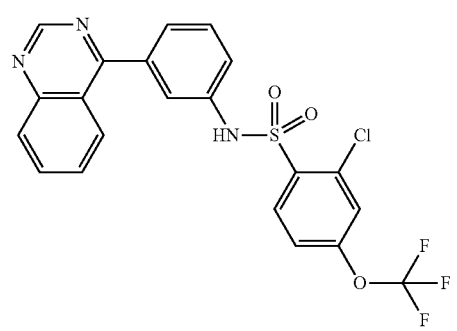
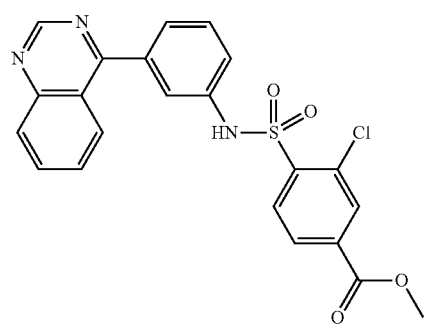
90
-continued
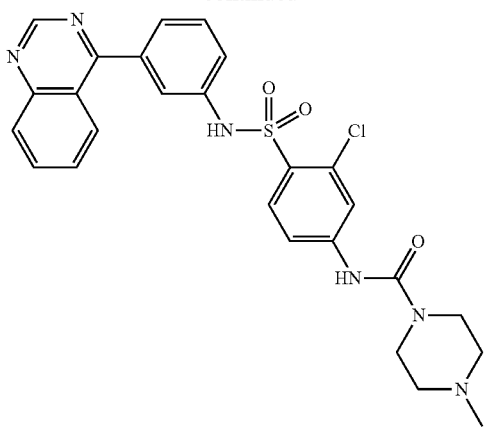
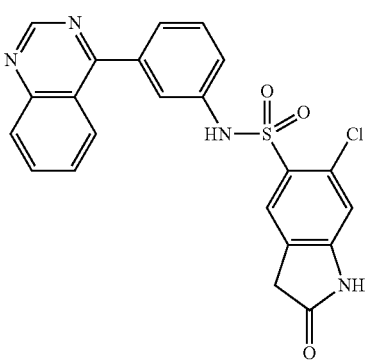
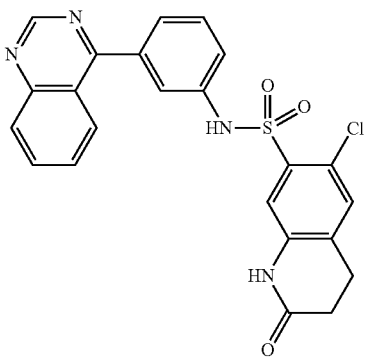
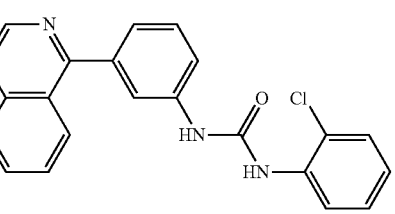

-continued
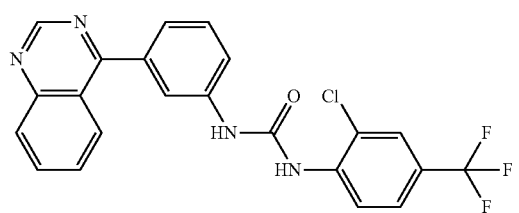
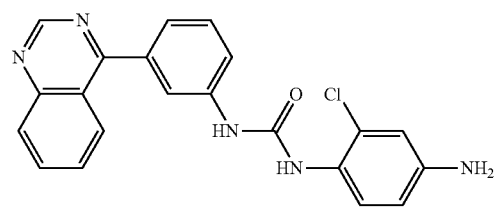
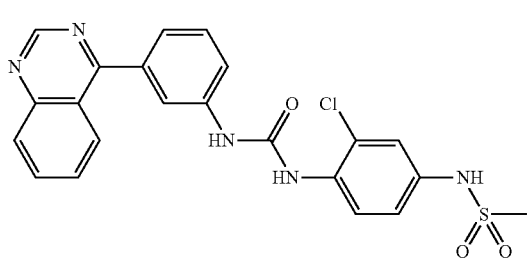
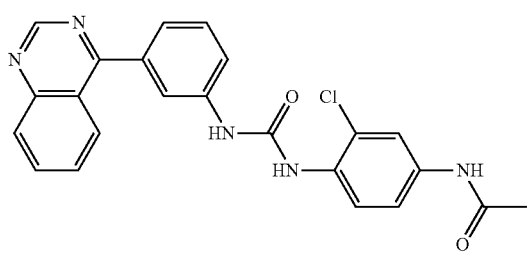
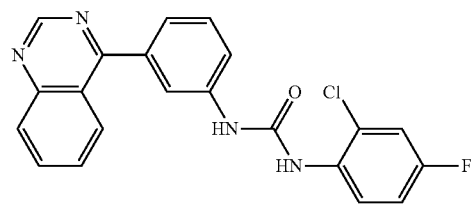
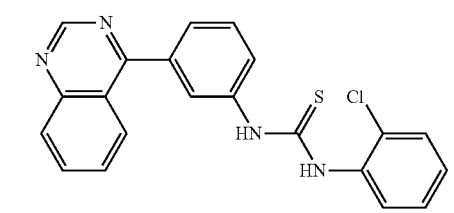
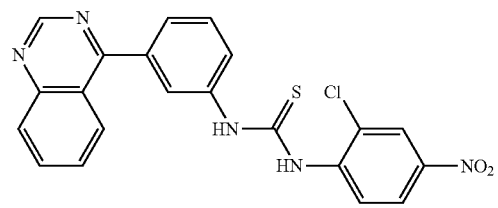
-continued
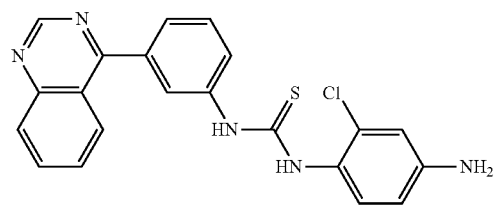
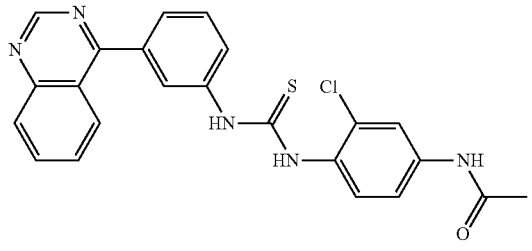
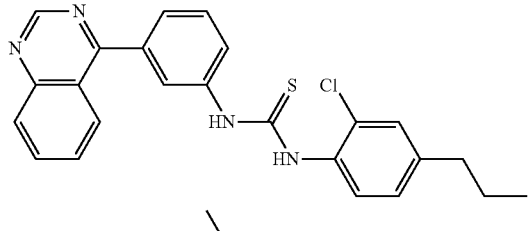
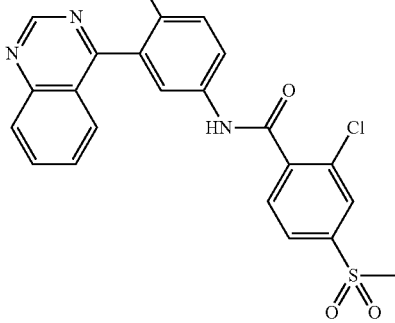
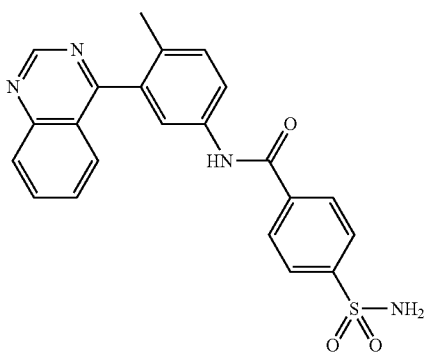
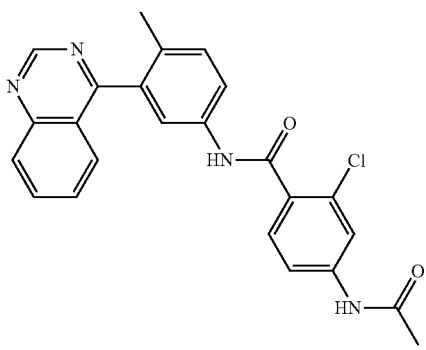

93
-continued
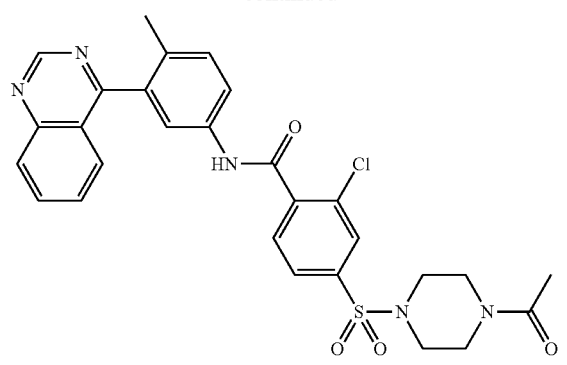
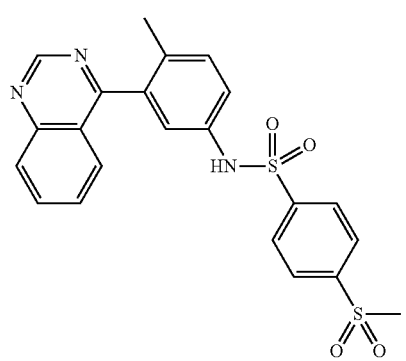
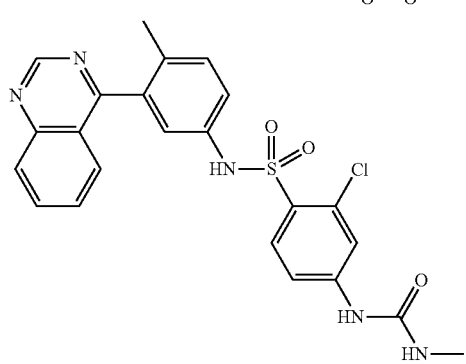
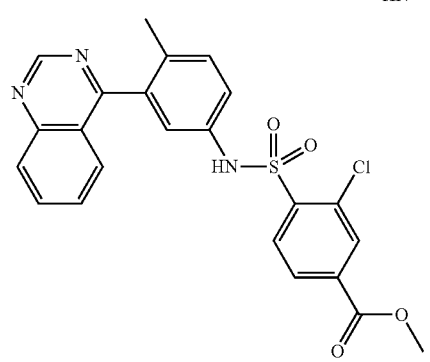
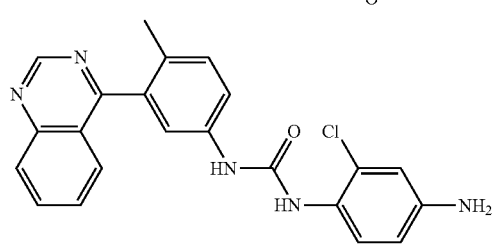
94
-continued
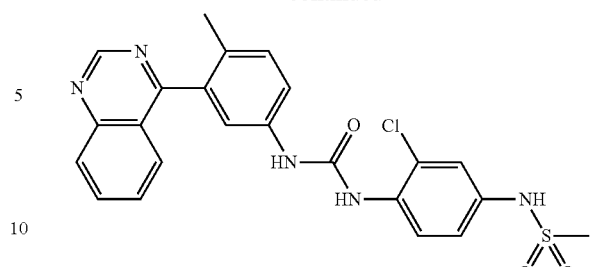
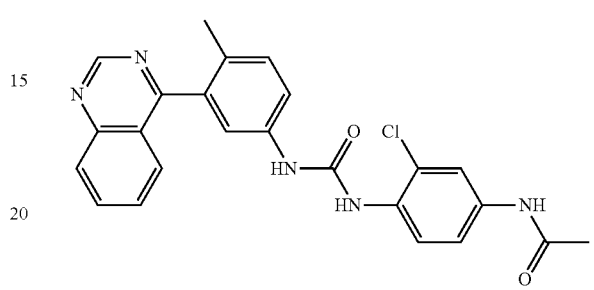
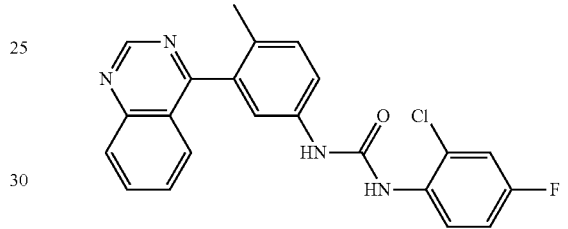
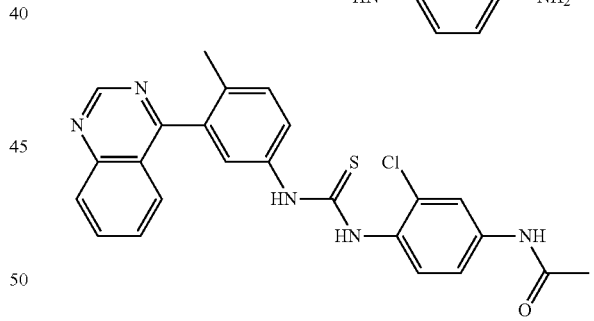
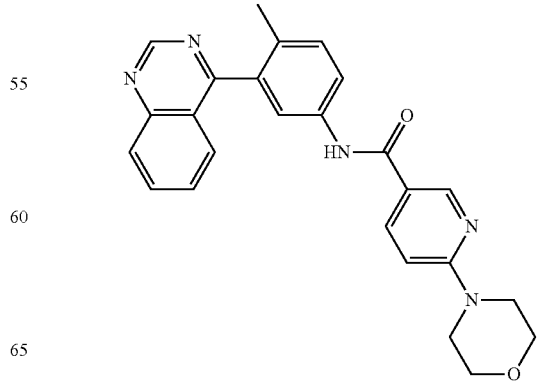

95
-continued
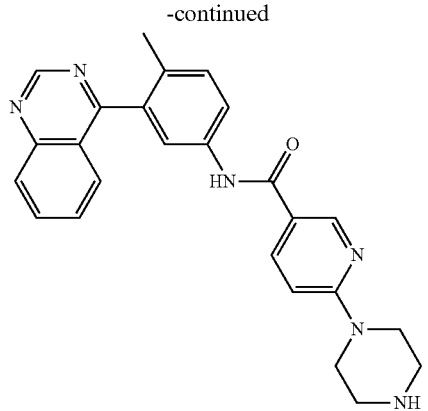
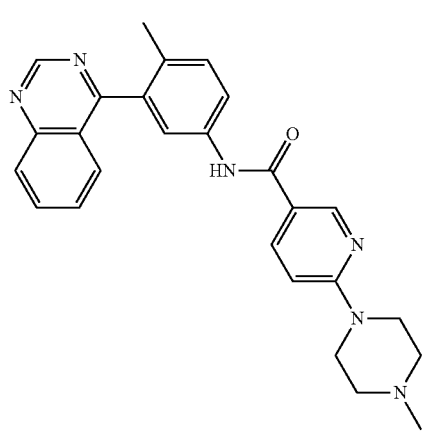
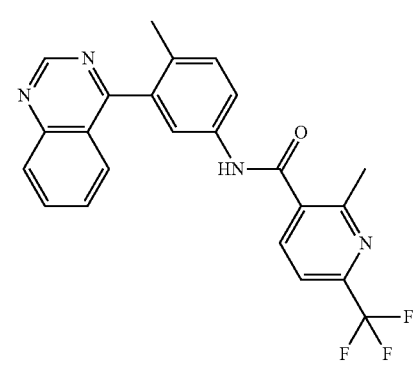
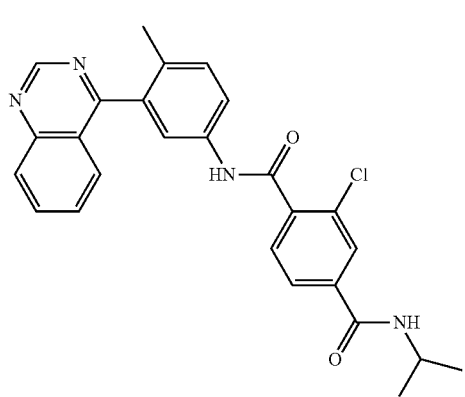
96
-continued
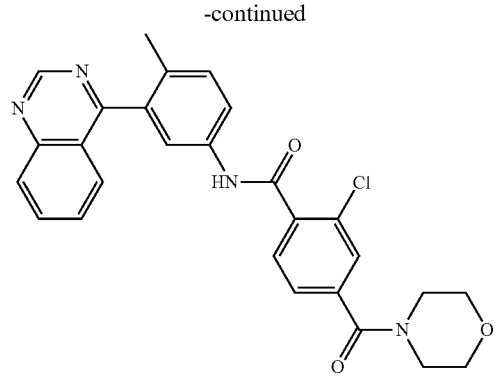
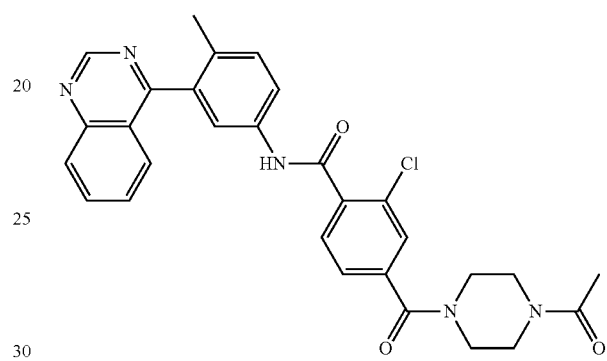
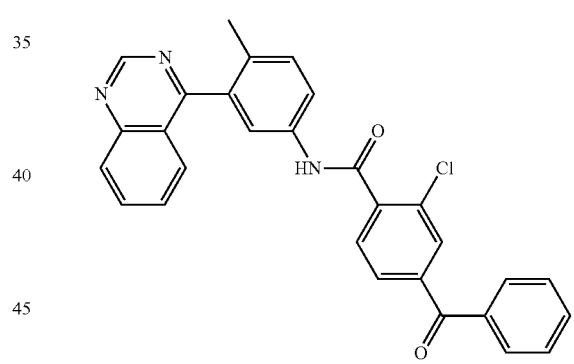
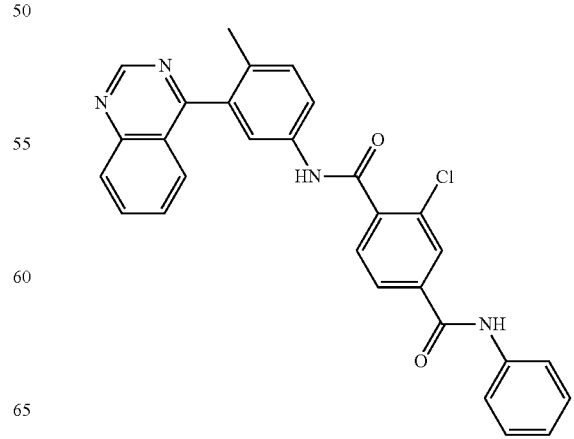

-continued

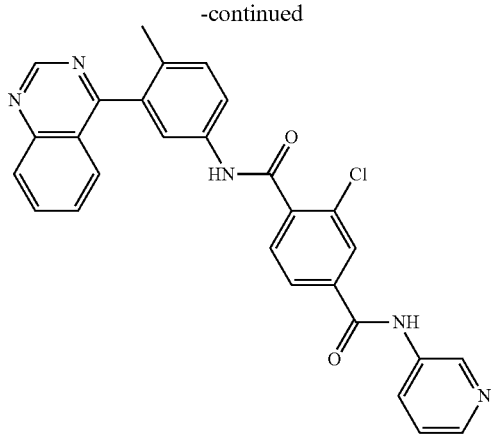

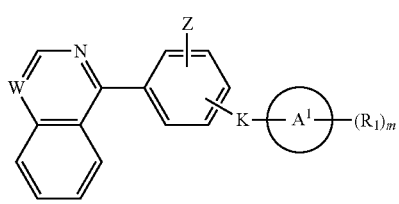

The present invention also relates to compounds as shown in Formula (A):

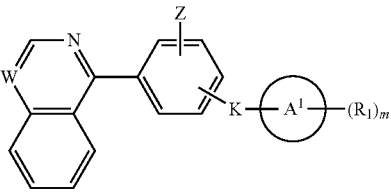
(A)

or pharmaceutically acceptable salts thereof, wherein:

K is selected from $NR_3C(O)$, $C(O)NR_3$, $NR_3SO_2$, $SO_2NR_3$, and $NR_4C(O)NR_5$;

$A^1$ is selected from aryl, heterocyclyl, and heteroaryl;

$R_1$ is selected from H, halo, nitro, $-OR_4$, $C_1$-$C_6$ alkyl, $C_1$-$C_6$ alkylsulfonyl, and $C_1$-$C_6$ haloalkyl;

m=0-4;

$R_3$, $R_4$, and $R_5$ are each independently selected from H and $C_1$-$C_6$ alkyl;

W is selected from CH and N;

Z is selected from H, halo, and $C_1$-$C_6$ alkyl, $C_1$-$C_6$ alkylthio, $-NR_4R_5$, $-OR_4$, and cyano.

In an embodiment, the present invention relates to compounds as shown in Formula (A):

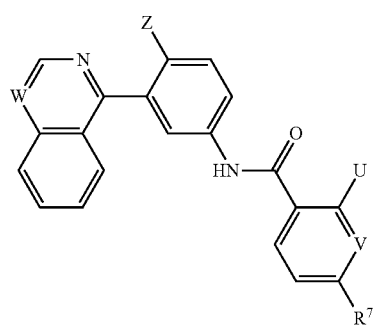
(A)

or pharmaceutically acceptable salts thereof, wherein:

K is selected from $NR_3C(O)$, $C(O)NR_3$, $NR_3SO_2$, $SO_2NR_3$, and $NR_4C(O)NR_5$;

$A^1$ is selected from phenyl and pyridyl;

$R_1$ is selected from H, halo, nitro, $C_1$-$C_6$ alkylsulfonyl, and $C_1$-$C_6$ alkyl;

M=0-4;

$R_3$, $R_4$, and $R_5$ are each independently selected from H and $C_1$-$C_6$ alkyl;

W is selected from CH and N;

Z is selected from H, halo, and $C_1$-$C_6$ alkyl.

The present invention also relates to compounds as shown in Formula (B):

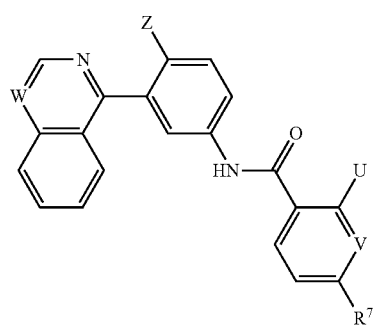
(B)

or a pharmaceutically acceptable salt thereof, wherein:

$R_3$, $R_4$, and $R_5$ are each independently selected from H and $C_1$-$C_6$ alkyl;

$R_7$ is selected from heterocyclyl, haloalkyl, $NR_3C(O)R_4$, $NR_3C(O)NR_4R_5$, $NR_3C(O)[C(R_3)(R_4)]_nO[C(O)]_pR_4$, $(CH_2)_nSO_2R_3$, $NR_3SO_2R_4$, $NR_3C(O)$-Q-$R_4$, and $N(OR_3)C(O)R_4$;

n is 1-2;

p is 0 or 1;

Q is heterocyclyl;

U is selected from H, halo, $C_1$-$C_6$ alkyl, $C_1$-$C_6$ alkylthio, $-NR_4R_5$, $-OR_4$, and cyano;

V is selected from CH and N;

W is selected from CH and N;

Z is selected from H, halo, and $C_1$-$C_6$ alkyl.

The present invention also relates to compounds as shown in Formula (C):

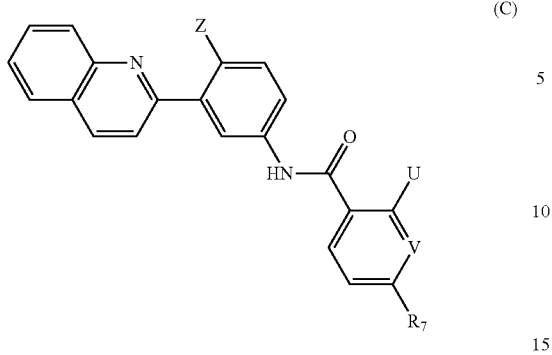

(C)

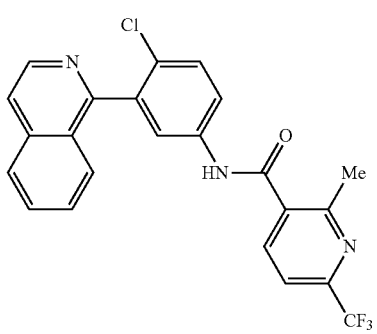

(iii)

or a pharmaceutically acceptable salt thereof, wherein:

$R_3$, $R_4$, and $R_5$ are each independently selected from H and $C_1$-$C_6$ alkyl;

$R_7$ is selected from heterocyclyl, haloalkyl, $NR_3C(O)R_4$, $NR_3C(O)NR_4R_5$, $NR_3C(O)[C(R_3)(R_4)]_nO[C(O)]_pR_4$, $(CH_2)_nSO_2R_3$, $NR_3SO_2R_4$, $NR_3C(O)$-Q-$R_4$, and $N(OR_3)C(O)R_4$;

n is 1-2;

p is 0 or 1;

Q is heterocyclyl;

U is selected from H, halo, $C_1$-$C_6$ alkyl, $C_1$-$C_6$ alkylthio, —$NR_4R_5$, —$OR_4$, and cyano;

V is selected from CH and N;

Z is selected from H, halo, and $C_1$-$C_6$ alkyl.

In specific embodiments, the invention relates to compounds of formulae (i)-(xv) as shown below, and pharmaceutically acceptable salts thereof:

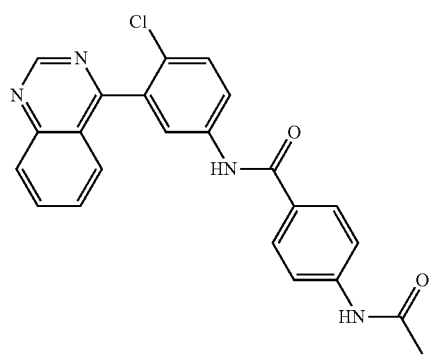

(iv)

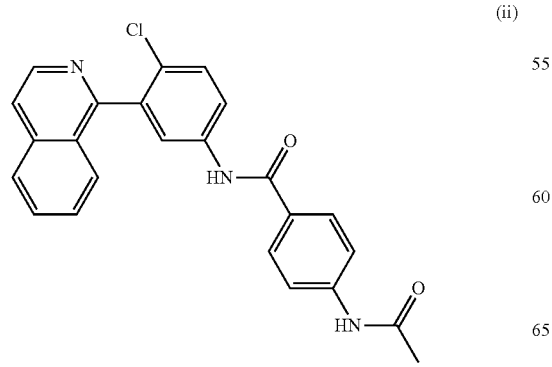

(i)

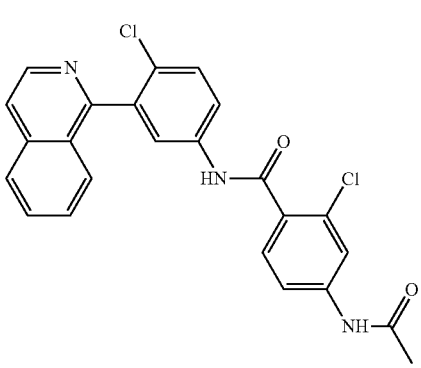

(v)

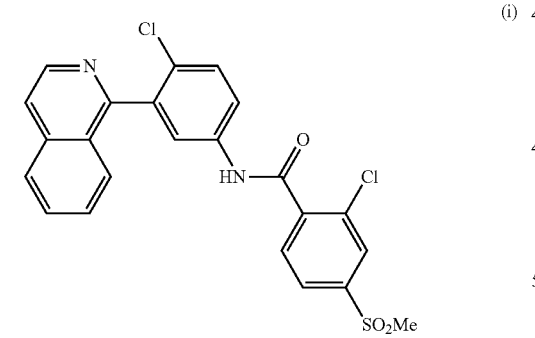

(ii)

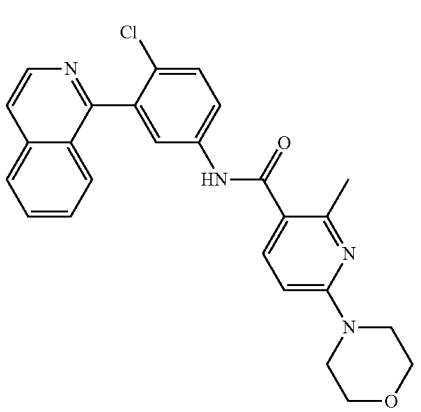

(vi)

101
-continued
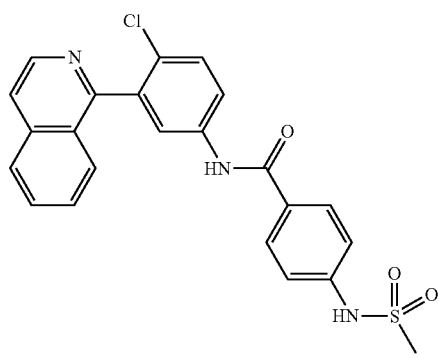
(vii)
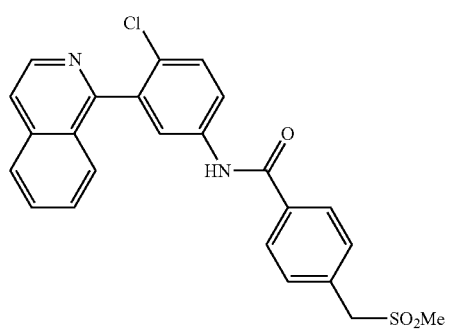
(viii)
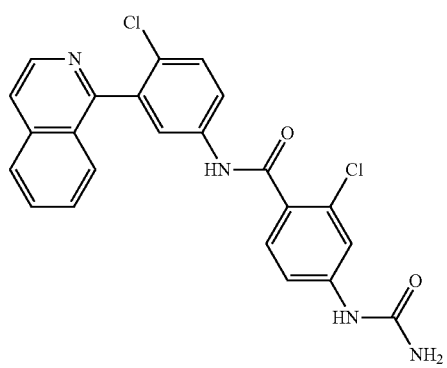
(ix)
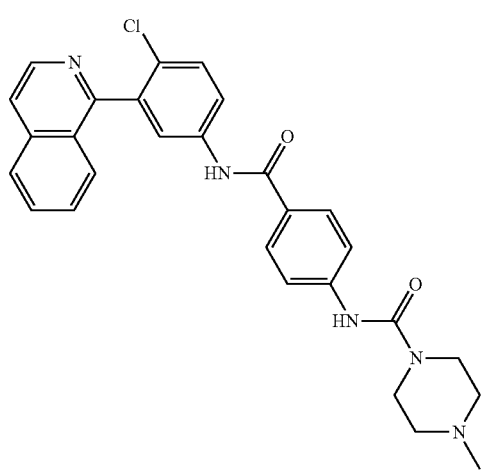
(x)
102
-continued
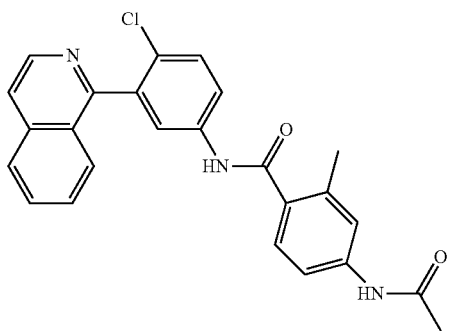
(xi)
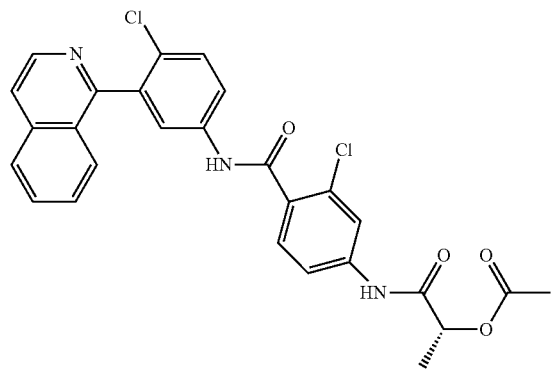
(xii)
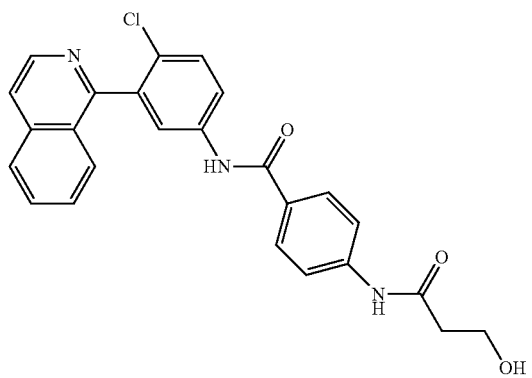
(xiii)
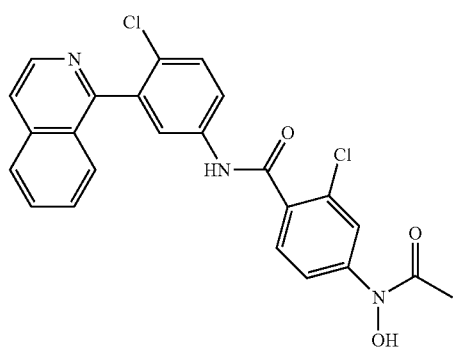
(xiv)

103
-continued (xv)

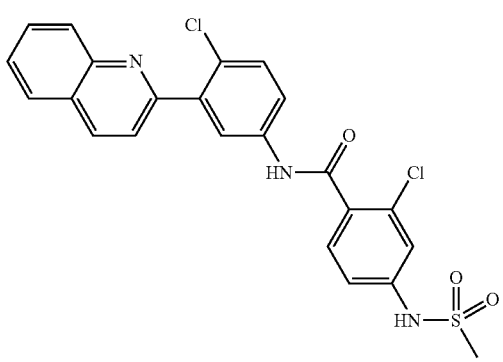

In another embodiment, a method of preparing the inventive compounds is provided. The compounds of the present invention can be generally prepared by coupling the central rings and A ring via established amide bond formation procedure. Compound (I) and all the other compounds of the invention may contain various stereoisomers, geometric isomers, tautomeric isomers, and the like. All of possible isomers and their mixtures are included in the present invention, and the mixing ratio is not particularly limited. Quinoline compounds of formula (C) may be prepared analogously to the isoquinoline and quinazoline compounds described below.

Synthesis of the isoquinoline of general formula (4) (wherein $R_1$ preferably is Cl) is preferably carried out as follows (Scheme 1): first, commercially available (±)-2-amino-1-phenylethanol (1) reacted with commercially available 2-chloro-5-nitrobenzoyl chloride (2), in an aprotic solvent, preferably dichloromethane in the presence of TEA, to form 2-chloro-N-(2-hydroxy-2-phenylethyl)-5-nitrobenzamide (3). The latter compound was then, upon exposure to a dehydrating agent, preferably phosphorus pentaoxide, or phosphorus oxychloride, under reflux conditions and in an inert solvent, preferably toluene and xylene, to form isoquinoline (4) (Manning H. C., Goebel, T., et al., *Org. Lett.*, 2002, 4, 1075-1078; Funabashi, K., Ratni, H., et. Al., *J. Am. Chem. Soc.*, 2001, 123, 10784-10785).

Scheme 1

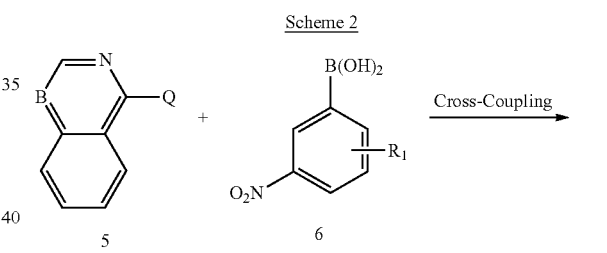

104
-continued

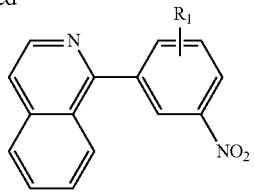

4

The alternative way to form the isoquinoline or quinazolines 7 is Suzuki cross-coupling reaction (Scheme 2). Various aryl boronic acid with compound 5 (wherein B is CH or N; Q is Cl, Br or I) afforded the compounds with formula 7 (Chapoulaud, V. G. et al., *Tetrahedron*, 2000, 56, 5499-5507; Mongin, F., Rebstock, A., et al., *J. Org. Chem.*, 2004, 69, 6766-6771) in the presence of palladium catalyst, such as palladium(II) acetate triphenylphosphine, dichlorobis(triphenylphosphine)palladium(0), or tetrakis(triphenylphosphine)palladium(0). The reaction also works with pseudohalides such as triflates (OTf), instead of halides, and also with boron-esters instead of boronic acids. Compound 5 (B is N and Q is Cl) was prepared by the reaction of 4-hydroxyquinazoline with $SOCl_2$/DMF under reflux (Hennequin L. F. et al., *J. Med. Chem.*, 1999, 42, 5369-5389).

Scheme 2

Compound 7 is then reduced, in the presence of reducing reagent, to form intermediate 8 (Scheme 3). The reduction of a nitro group can be carried out in a number of ways well known to those skilled in the art of organic synthesis including, but not limited to, catalytic hydrogenation, reduction with $SnCl_2$ and reduction with titanium bichloride. Here the preferably reducing reagent is $SnCl_2$. In a particular embodiment, the reduction reaction is performed at about 60° C. For an overview of reduction methods see: Hudlicky, M. Reductions in Organic Chemistry, ACS Monograph 188, 1996.

Scheme 3

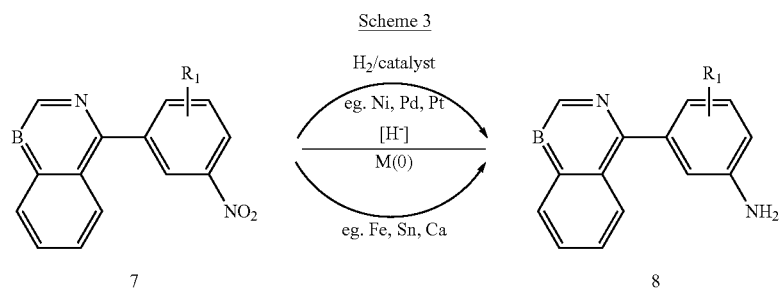

When the aldehyde (9) (wherein R' represents the substituted or unsubstituted ($C_1$-$C_3$) alkyl) was reacted with the intermediate 8, the product was subsequently reduced using reducing agents such as, for example, hydrogen, simple or complex metal hydrides, transition metals or salts thereof, but preferably using sodium cyanoborohydride, to form the N-alkyl-amino compound with formula (10) (Scheme 4).

Scheme 4

Compound 8 or 10 can be converted to 11 (wherein $R_3$ is hydrogen or an optionally substituted $C_{1-4}$ alkyl group). The compound 11 is then, in accordance with the process in the patent WO 01/25220 A1, acylated with carboxylic acid, carboxylic anhydride or acid chloride of the general formula 12 (wherein Q is chloride or O-EDC), or reacted with an acid chloride, sulfamoyl halide (13), isocyanate (14) or thiocyanate (15) to form the N-acyl-amino compound of formula Ia, IIa, IIIa or IVa (Scheme 5). The reaction is advantageously carried out in an aprotic solvent in the presence of a base at ambient temperature.

The aprotic solvent of condensation reaction may be used, but not limited to, dichloromethane, acetone, dioxane, acetonitrile, chloroform, dichloroethane, diethyl ether, THF, DMF, and the like, or may be used alone or as a mixture thereof, conveniently at a temperature within the range −60° C. to reflux.

A variety of base reagents may be used, including but not limited to, pyridine, triethylamine, diisopropylethylamine, methylamine, imidazole, benzimidazole, histidine, sodium hydride, and the like, preferably is the pyridine, or may be used alone without solvents.

When Compound 11 reacted with aldehyde or ketone with formula 16 (wherein $R_4$ represents hydrogen or an optionally substituted $C_{1-4}$ alkyl group, $R_2$ and m are defined herein) via condensation reaction, the product was subsequently reduced using reducing reagents to form the compound Va (Scheme 5).

The solvent of condensation reaction may be used, but not limited to, dichloromethane, acetone, dioxane, acetonitrile, chloroform, dichloroethane, diethyl ether, THF, DMF, and the like, or may be used alone or as a mixture thereof, conveniently at a temperature within the range −60° C. to room temperature.

A variety of reducing agent and reaction condition can be used to reduce imine. Sodium cyanoborohydride may be used as the reducing reagent. Other reducing reagents that can be used include, but are not limited to, sodium borohydride, sodium dithionite, lithium aluminum hydride, Red-Al, and the like. The solvent may be used, but not limited to, alcoholic solvents such as methanol and ethanol under neutral conditions at temperatures range from 0° C. to that of the refluxing solvent, DMF, acetonitrile, benzene, toluene, and the like.

Scheme 5

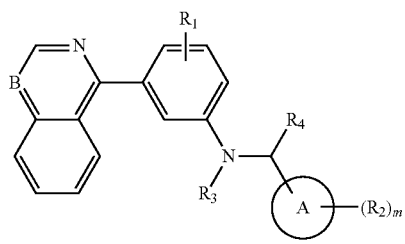

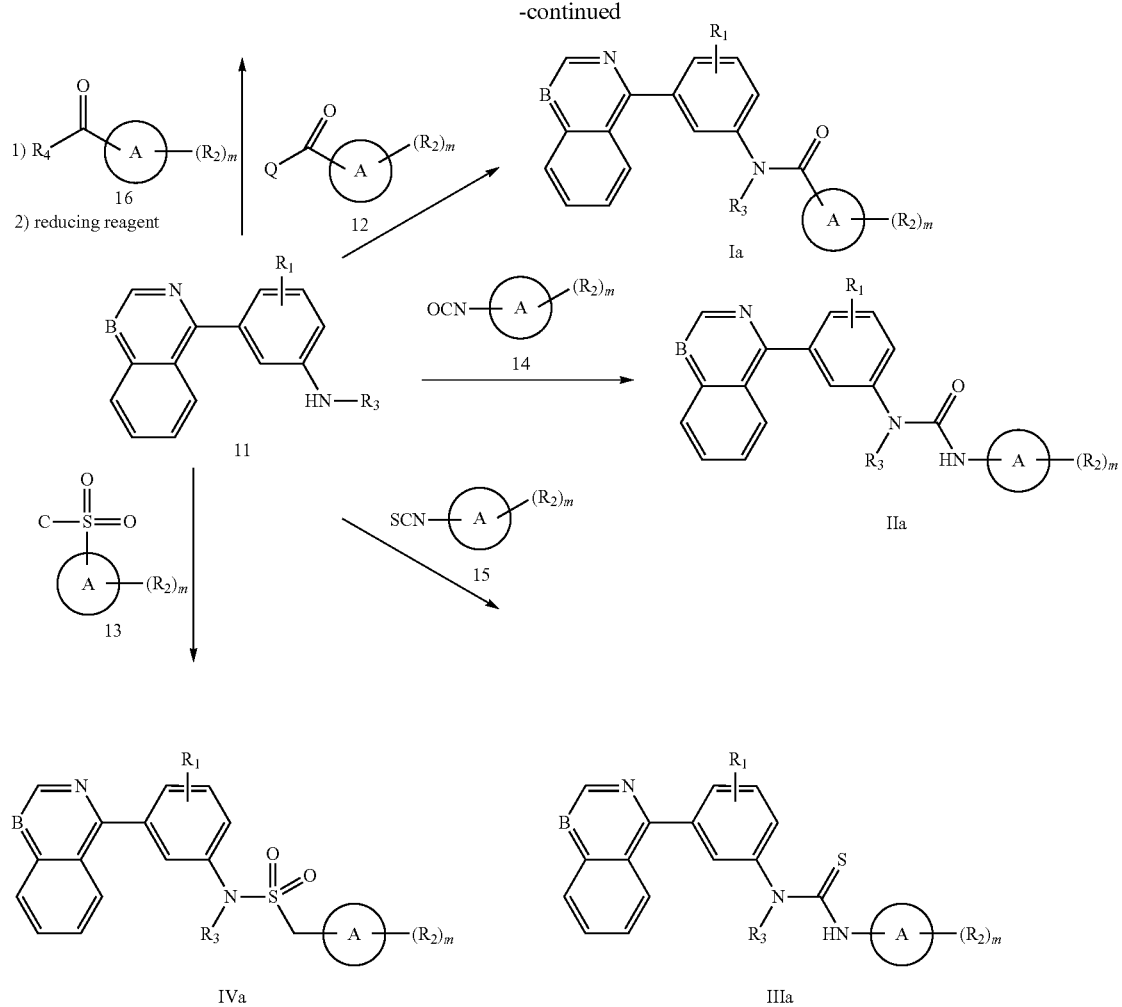

In the scheme 6, the compound 8 reacted with a nitrite in acidic medium, and the resulting aryl diazonium salt solution was mixed with a solution of sulfur dioxide in acetic acid in the presence of copper (I) salts, such as $Cu_2Cl_2$ to form the desired aryl sulfonyl chloride (Hanson, J., Dogne J., et al., *J. Med. Chem.*, 2007, 50, 3928-3936). The compound 17 then reacted with amine with the formula 18 (wherein $R_3$ is defined herein) to form the compound Ib.

The aprotic solvent of condensation reaction may be used, but not limited to, to dichloromethane, acetone, dioxane, acetonitrile, chloroform, dichloroethane, diethyl ether, THF, DMF, and the like, may be used alone or as a mixture thereof, conveniently at a temperature within the range −60° C. to reflux.

A variety of base agent may be used, but not limited to, pyridine, triethylamine, di-isopropylethylamine, methylamine, imidazole, benzimidazole, histidine, sodium hydride, and the like, preferably is the pyridine, may be used alone without solvents.

Scheme 6

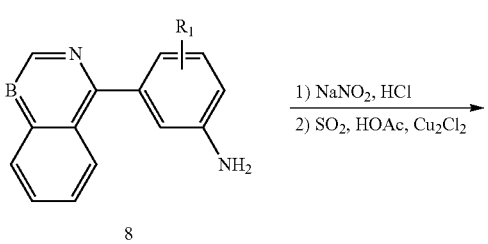

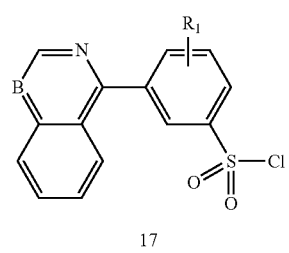

-continued

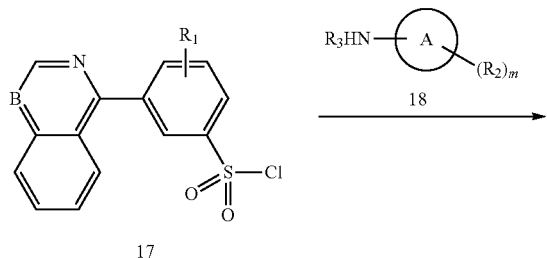

17

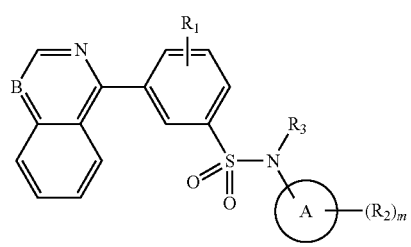

Ib

In the scheme 7, compound 19 was reduced to amine 20 with the same method for the preparation of compound 8. In a particular embodiment, the reduction reaction is performed with $SnCl_2$ at about room temperature. Intermediate 20 reacted with an activated acid 21 (wherein R' represents the substituted or unsubstituted ($C_1$-$C_{10}$) alkyl, alkenyl, ($C_3$-$C_7$) aryl or heteroaryl) to yield the final compound Ic. In a particular embodiment, the activated acid (21) is acid halide (for example Q is chloride) or activated ester (for example Q is O-EDC). In a particular embodiment the reaction is performed at about 0° C. to room temperature.

Scheme 7

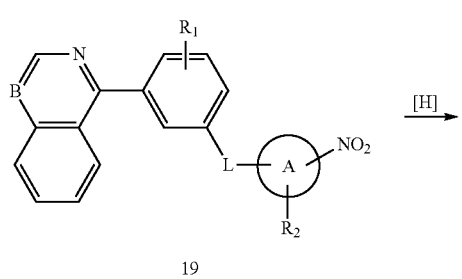

19

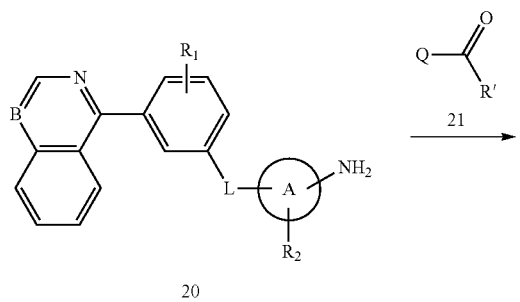

20

-continued

Ic

Intermediate 20 reacted with the appropriate sulfonyl chloride R'—($SO_2$)Cl (21) (wherein R' represents the substituted or unsubstituted ($C_1$-$C_{10}$) alkyl, alkenyl, ($C_3$-$C_7$) aryl or heteroaryl) in the presence of a non-neucleophilic base such as TEA or diisopropylethylamine to form the desired sulfonamide Id (Scheme 8).

Scheme 8

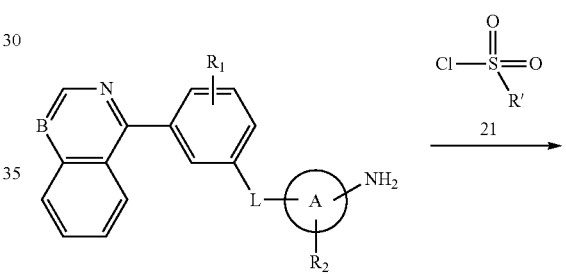

Id

As illustrated in Scheme 9, formula Ie can be prepared by condensation reaction with a substituted aldehyde or ketone $R_7COR_8$ (wherein $R_7$ or $R_8$ independently or together represents hydrogen, the substituted or unsubstituted ($C_1$-$C_{10}$) alkyl, alkenyl, aryl or heteroaryl), followed by a reduction reaction. The solvent for the condensation reaction, the reducing reagent and the reaction conditions can be the same as for the preparation of compound Va.

Scheme 9

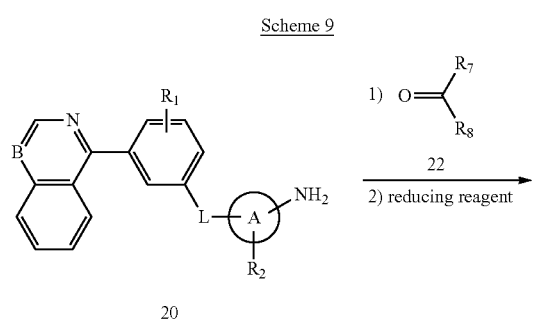

20

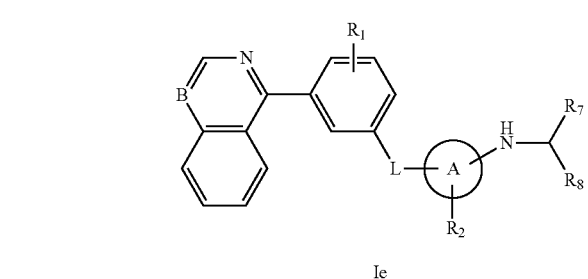

Ie

Compound 23, an isoquinalone or quinazoline with a heteroaryl group substituted with potential leaving groups (for example Cl, Br, I, SO2Me etc.) may undergo substitution reactions on treatment with neucleophiles, such as amine 24, $R_9NHR_{10}$ (wherein $R_9$ or $R_{10}$ independently or together represent substituted or unsubstituted ($C_1$-$C_{10}$) alkyl, alkenyl; or ($C_3$-$C_7$) aryl or heteroaryl) or a secondary amine of formula 25 (wherein Z, $R_5$ and $R_6$ are as defined herein) to obtain compounds If and Ig (Scheme 10), in the presence of an inert solvent.

There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, especially aromatic and aliphatic hydrocarbons, such as methylene chloride, chloroform, carbon tetrachloride, dichloroethane, chlorobenzene and the dichlorobenzenes; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitro compounds, which may be nitroalkanes or nitroaranes, such as nitroethane and nitrobenzene; nitriles, such as acetonitrile and isobutyronitrile; amides, which may be fatty acid amides, such as formamide, dimethylformamide, dimethylacetamide and hexamethylphosphoric triamide; and sulphoxides, such as dimethyl sulphoxide and sulpholane.

The reaction can take place over a wide range of temperatures, and the precise reaction temperature is not critical to the invention. In general, we found it convenient to carry out the reaction at a temperature of from −50° C. to 100° C.

Scheme 10

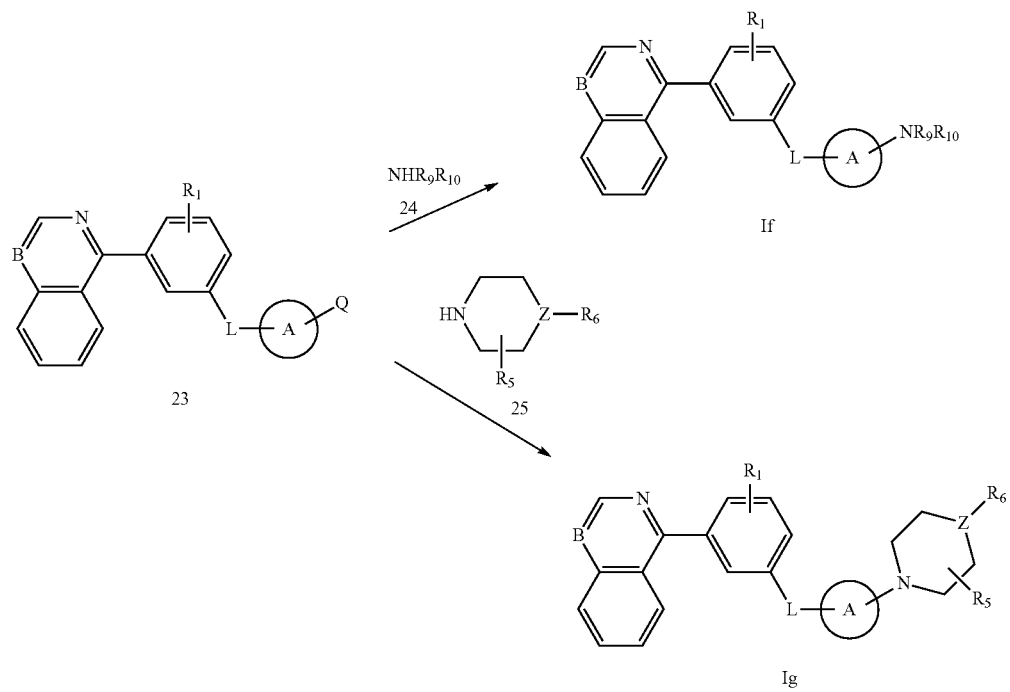

Scheme 11 illustrates one of the methods to swap the —OH group in the —COON group of a carboxylic acid 26 for a chlorine atom to make acyl chlorides of formula 12. A variety of chlorine agents and reaction conditions can be used. Sulphur dichloride oxide (thionyl chloride) may be used as chlorine agent without solvent to under reflux conditions (Clayden, J., Organic Chemistry. Oxford University Press. 2001, 276-296). Other agents that can be used include, but are not limited to, phosphorus (V) chloride, phosphorus (III) chloride (Boyd, R; Morrison, R., Organic chemistry, 1992, 666-762), oxalyl chloride and cyanuric chloride (Venkataraman, K. and Wagle, D. R, Tet. Lett. 1979, 20 (32): 3037-3040), and the like. Some HCl is undurable acids can form the acyl chloride via the Applye reaction (Taschner, M. J., e-EROS: Encyclopedia of Reagents for Organic Synthesis, 2001).

Scheme 12 illustrates how methyl ester 27 can be heated under reflux with a diluted alkali-like sodium hydroxide solution, potassium hydroxide solution or lithium hydroxide solution, preferably with lithium hydroxide solution, to form the acid of formula 28. Protic solvents including, but not limited to water, dimethyl sulfoxide, dimethylformamide, dioxane and hexamethylphosphorotriamide, and tetrahydrofuran may be used. Preferably the protic solvent is a mixture of tetrahydrofuran and water. The product 28 may further be reacted with a chlorine agent, with same reaction conditions used to prepare 12, to form acid chloride (wherein Q is chloride), and the product can also react with EDCl to form the active ester (Q is O-EDC). Compound 29 may further be reacted with amine 24 or 25 to form the amide compounds Ih and Ij (Scheme 12).

Scheme 11

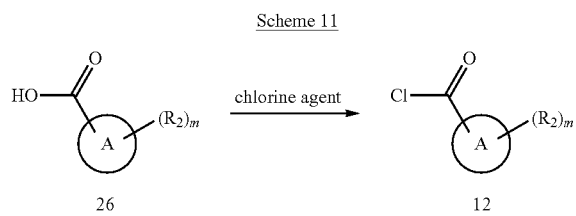

Scheme 12

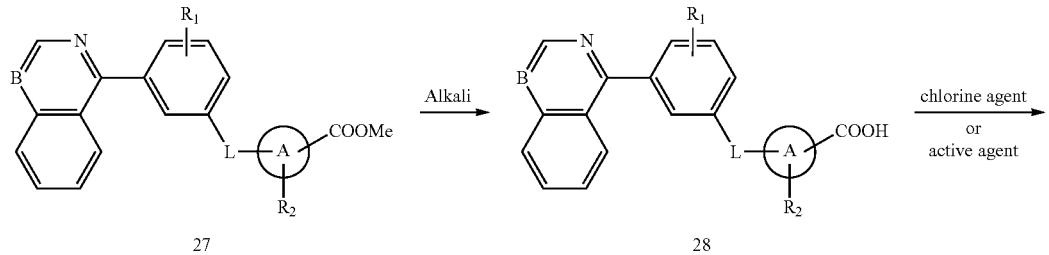

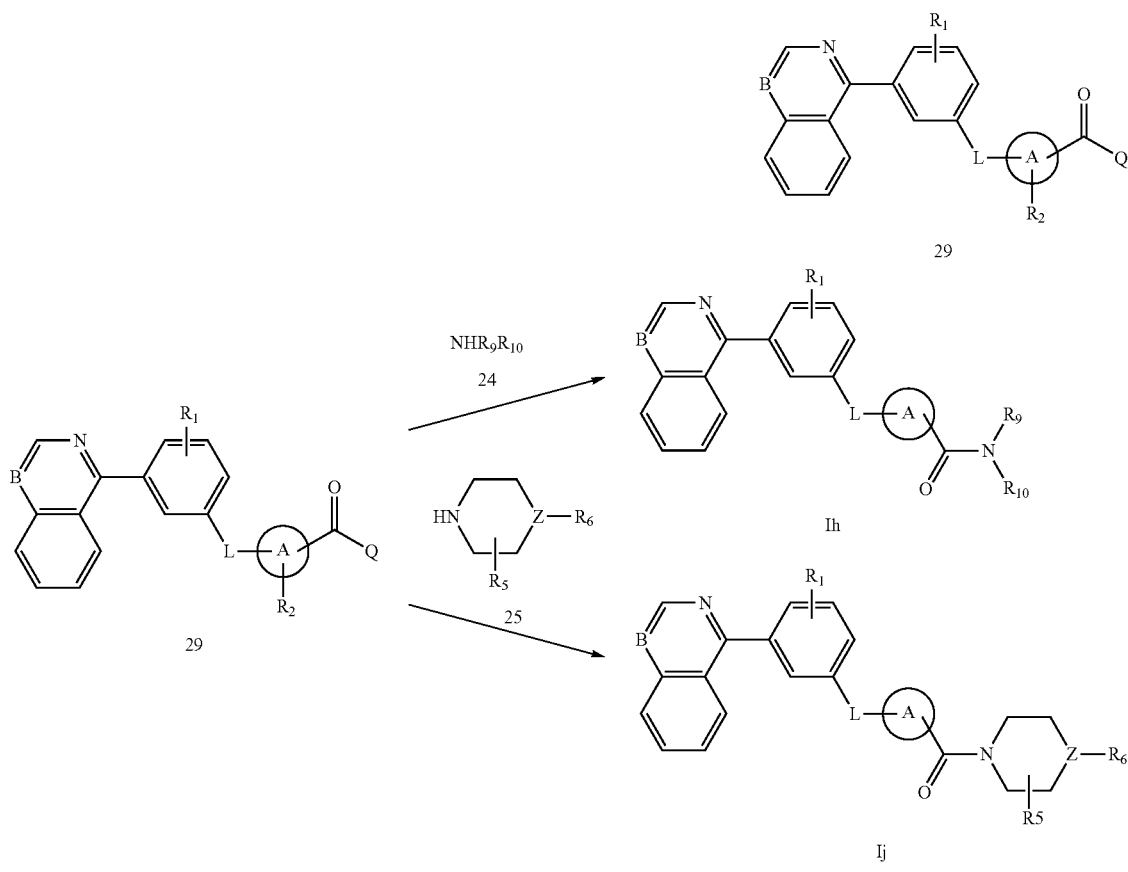

The preparation of the compounds with formula Ik, Im, Io in this invention can be carried out by the methods known in the art (for example Stephenson, F. M., Org. Synth. 1963, 4, 984; Snell, J. M., Weissberger, A., et al., Org. Synth, 1955, 3, 788; Greenwood, F. L., et al., Org. Synth., 1963, 4, 108). Methylene aryl compound 30 was combined with benzoyl peroxide and N-bromosuccinimide in the solution of 5% AcOH in benzene and heated to obtain benzyl bromide derivative 31. Compound 31 can be reacted with neucleophiles, such as amines 24 and 25 (wherein $R_5$, $R_6$, $R_9$ and $R_{10}$ are as defined herein), and thiol derivatives $R_{11}SH$ 32 (wherein $R_{11}$ represents substituted or unsubstituted ($C_1$-$C_{10}$) alkyl, alkenyl, ($C_3$-$C_7$) aryl or heteroaryl) to obtain Ik, Im and Io in the presence of a non-neucleophilic base such as potassium carbonate, cesium carbonate, TEA or diisopropylethylamine (Scheme 13).

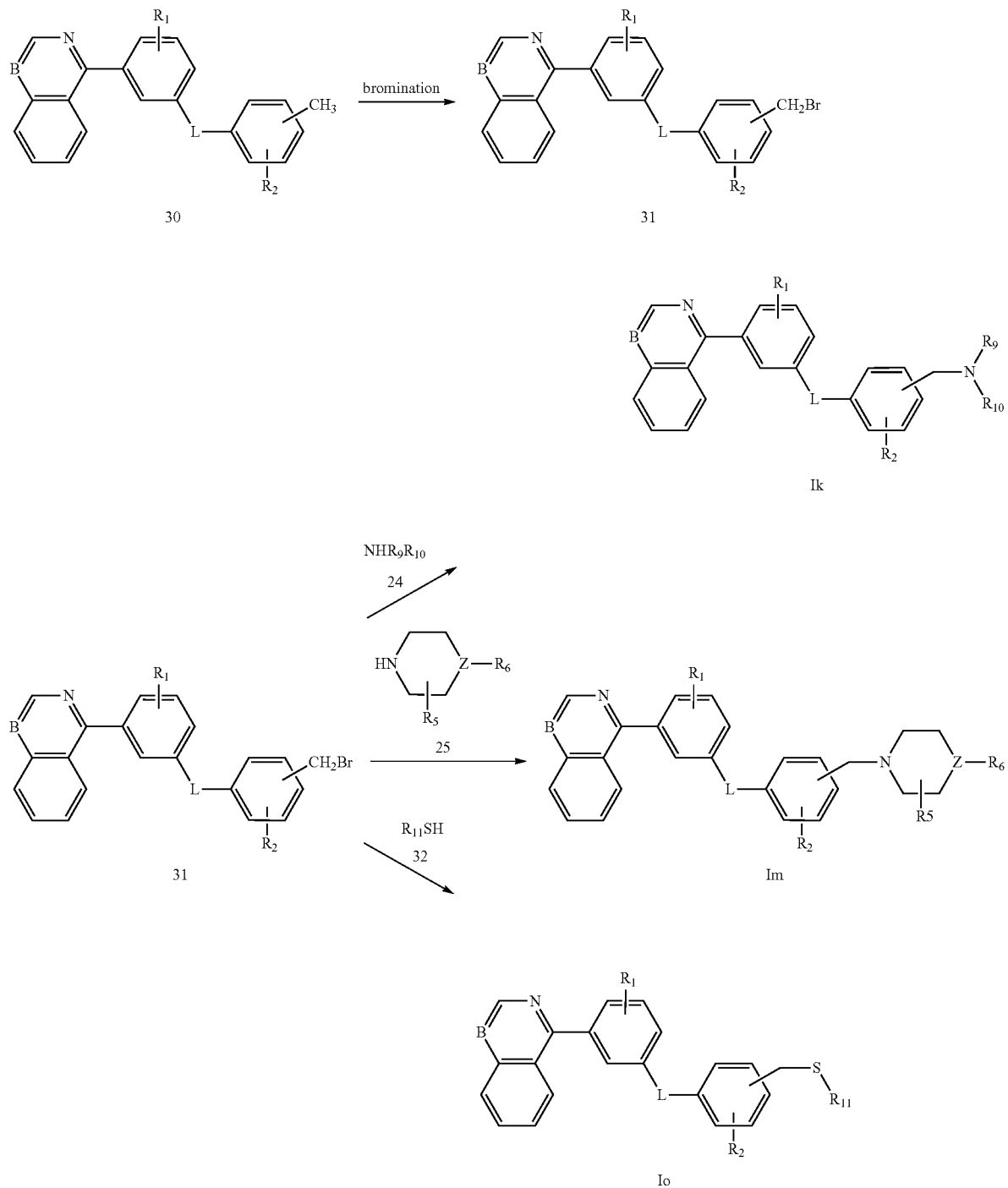

Scheme 13

The preparation of the compounds with formula Ip in this invention can be carried out by a method in which thiol derivatives (Io) are oxidized to sulfones (Ip) in the presence of protic solvents such as water, methanol, and ethanol (Scheme 14).

The oxidizing agent used may be, but is not limited to, OXONE®, meta-chloroperbenzoic acid, peroxytrifluoroacetic acid, or hydrogen peroxide. Suitable solvents can be, but are not limited to chloroform, dichloromethane, benzene, and toluene in admixture with an alcoholic solvent, such as methanol, ethanol, isopropanol, or 1-butanol, in particular, ethanol. The oxidation reaction runs at temperatures within the convenient range of −60° C. to room temperature.

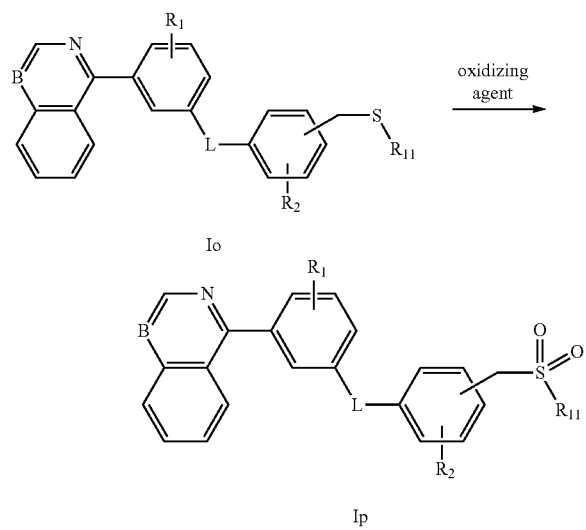

The present invention provides compositions of matter that are formulations of one or more active drugs and a pharmaceutically-acceptable carrier. In this regard, the invention provides a composition for administration to a mammalian subject, which may include a compound of formula I, or its pharmaceutically acceptable salts.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4} \text{alkyl})_4$ salts. This invention also envisions the quaternization of any basic nitrogen-containing groups of the compounds disclosed herein. Water or oil-soluble or dispersible products may be obtained by such quaternization. The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutically acceptable compositions of this invention may be orally administered in any orally acceptable dosage form including, but not limited to, capsules, tablets, troches, elixirs, suspensions, syrups, wafers, chewing gums, aqueous suspensions or solutions.

The oral compositions may contain additional ingredients such as: a binder such as microcrystalline cellulose, gum tragacanth or gelatin; an excipient such as starch or lactose, a disintegrating agent such as alginic acid, corn starch and the like; a lubricant such as magnesium stearate; a glidant such as colloidal silicon dioxide; and a sweetening agent such as sucrose or saccharin or flavoring agent such as peppermint, methyl salicylate, or orange flavoring. When the dosage unit form is a capsule, it may additionally contain a liquid carrier such as a fatty oil. Other dosage unit forms may contain other various materials which modify the physical form of the dosage unit, such as, for example, a coating. Thus, tablets or pills may be coated with sugar, shellac, or other enteric coating agents. A syrup may contain, in addition to the active ingredients, sucrose as a sweetening agent and certain preservatives, dyes and colorings and flavors.

Materials used in preparing these various compositions should be pharmaceutically or veterinarally pure and non-toxic in the amounts used.

For the purposes of parenteral therapeutic administration, the active ingredient may be incorporated into a solution or suspension. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The pharmaceutical forms suitable for injectable use include sterile solutions, dispersions, emulsions, and sterile powders. The final form should be stable under conditions of manufacture and storage. Furthermore, the final pharmaceutical form should be protected against contamination and should, therefore, be able to inhibit the growth of microorganisms such as bacteria or fungi. A single intravenous or intraperitoneal dose can be administered. Alternatively, a slow long-term infusion or multiple short-term daily infusions may be utilized, typically lasting from 1 to 8 days. Alternate day dosing or dosing once every several days may also be utilized.

Sterile, injectable solutions may be prepared by incorporating a compound in the required amount into one or more appropriate solvents to which other ingredients, listed above or known to those skilled in the art, may be added as required. Sterile injectable solutions may be prepared by incorporating the compound in the required amount in the appropriate solvent with various other ingredients as required. Sterilizing procedures, such as filtration, may then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer. In all cases, the final form, as noted, must be sterile and should also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

In accordance with the invention, there are provided compositions containing triazine derivatives and methods useful for the in vivo delivery of triazine derivatives in the form of nanoparticles, which are suitable for any of the aforesaid routes of administration.

U.S. Pat. Nos. 5,916,596, 6,506,405 and 6,537,579 teach the preparation of nanoparticles from the biocompatible polymers, such as albumin. Thus, in accordance with the present invention, there are provided methods for the formation of nanoparticles of the present invention by a solvent evaporation technique from an oil-in-water emulsion prepared under conditions of high shear forces (e.g., sonication, high pressure homogenization, or the like).

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

In accordance with the invention, the compounds of the invention inhibit the hedgehog signaling and may be used to treat cancers associated with aberrant hedgehog signaling, cellular proliferation or hyperproliferation, such as cancers which include but are not limited to tumors of the nasal cavity, paranasal sinuses, nasopharynx, oral cavity, oropharynx, larynx, hypopharynx, salivary glands, and paragangliomas. The compounds of the invention may also be used to treat cancers of the liver and biliary tree (particularly hepatocellular carcinoma), intestinal cancers, particularly colorectal cancer, ovarian cancer, small cell and non-small cell lung cancer, breast cancer, sarcomas (including fibrosarcoma, malignant fibrous histiocytoma, embryonal rhabdomysocarcoma, leiomysosarcoma, neuro-fibrosarcoma, osteosarcoma, synovial sarcoma, liposarcoma, and alveolar soft part sarcoma), neoplasms of the central nervous systems (particularly brain cancer), and lymphomas (including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma).

The compounds and methods of the present invention, either when administered alone or in combination with other agents (e.g., chemotherapeutic agents or protein therapeutic agents described below) are also useful in treating a variety of disorders, including but not limited to, for example: stroke, cardiovascular disease, myocardial infarction, congestive heart failure, cardiomyopathy, myocarditis, ischemic heart disease, coronary artery disease, cardiogenic shock, vascular shock, pulmonary hypertension, pulmonary edema (including cardiogenic pulmonary edema), pleural effusions, rheumatoid arthritis, diabetic retinopathy, retinitis pigmentosa, and retinopathies, including diabetic retinopathy and retinopathy of prematurity, inflammatory diseases, restenosis, asthma, acute or adult respiratory distress syndrome (ARDS), lupus, vascular leakage, protection from ischemic or reperfusion injury such as ischemic or reperfusion injury incurred during organ transplantation, transplantation tolerance induction; ischemic or reperfusion injury following angioplasty;

arthritis (such as rheumatoid arthritis, psoriatic arthritis or osteoarthritis); multiple sclerosis; inflammatory bowel disease, including ulcerative colitis and Crohn's disease; lupus (systemic lupus crythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' disease; Addison's disease (autoimmune disease of the adrenal glands); autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including those where kineses such as Src-family kineses are activated or overexpressed, such as colon carcinoma and thymoma, or cancers where kinase activity facilitates tumor growth or survival; glomerulonephritis, serum sickness; uticaria; allergic diseases such as respiratory allergies (asthma, hayfever, allergic rhinitis) or skin allergies; mycosis fungoides; acute inflammatory responses (such as acute or adult respiratory distress syndrome and ischemialreperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; morphea; peripheral limb ischemia and ischemic limb disease; bone disease such as osteoporosis, osteomalacia, hyperparathyroidism, Paget's disease, and renal osteodystrophy; vascular leak syndromes, including vascular leak syndromes induced by chemotherapies or immunomodulators such as IL-2; spinal cord and brain injury or trauma; glaucoma; retinal diseases, including macular degeneration; vitreoretinal disease; pancreatitis; vasculatides, including vasculitis, Kawasaki disease, thromboangiitis obliterans, Wegener's granulomatosis, and Behcet's disease; scleroderma; preeclampsia; thalassemia; Kaposi's sarcoma; von Hippel Lindau disease; and the like.

The invention also provides methods of treating a mammal afflicted with the above diseases and conditions. The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

In one aspect, the invention compounds are administered in combination with chemotherapeutic agent, an anti-inflammatory agent, antihistamines, chemotherapeutic agent, immunomodulator, therapeutic antibody or a protein kinase inhibitor, e.g., a tyrosine kinase inhibitor, to a subject in need of such treatment.

The method includes administering one or more of the inventive compounds to the afflicted mammal. The method may further include the administration of a second active agent, such as a cytotoxic agent, including alkylating agents, tumor necrosis factors, intercalators, microtubulin inhibitors, and topoisomerase inhibitors. The second active agent may be co-administered in the same composition or in a second composition. Examples of suitable second active agents include, but are not limited to, a cytotoxic drug such as Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil 131; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-Ib; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

In accordance with the invention, the compounds and compositions may be used at sub-cytotoxic levels in combination with other agents in order to achieve highly selective activity in the treatment of non-neoplastic disorders, such as heart disease, stroke and neurodegenerative diseases (Whitesell et al., Curr Cancer Drug Targets (2003), 3(5), 349-58).

The exemplary therapeutic agents that may be administered in combination with invention compounds include EGFR inhibitors, such as gefitinib, erlotinib, and cetuximab. Her2 inhibitors include canertinib, EKB-569, and GW-572016. Also included are Src inhibitors, dasatinib, as well as Casodex (bicalutamide), Tamoxifen, MEK-1 kinase inhibitors, MARK kinase inhibitors, PI3 inhibitors, and PDGF inhibitors, such as imatinib, Hsp90 inhibitors, such as 17-AAG and 17-DMAG. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kineses, and inhibitors of integrin.

The pharmaceutical composition and method of the present invention may further combine other protein therapeutic agents such as cytokines, immunomodulatory agents and antibodies. As used herein the term "cytokine" encompasses chemokines, interleukins, lymphokines, monokines, colony stimulating factors, and receptor associated proteins, and functional fragments thereof. As used herein, the term "functional fragment" refers to a polypeptide or peptide which possesses biological function or activity that is identified through a defined functional assay. The cytokines include endothelial monocyte activating polypeptide II (EMAP-II), granulocyte-macrophage-CSF (GM-CSF), granulocyte-CSF (G-CSF), macrophage-CSF (M-CSF), IL-1, IL-2, IL-3, IL-4, IL-5, IL-6, IL-12, and IL-13, interferons, and the like and which is associated with a particular biologic, morphologic, or phenotypic alteration in a cell or cell mechanism.

Other therapeutic agents for the combinatory therapy include cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and for gpn39 (i.e., CD154), fusion proteins constructed from CD40 and gp39 (CD40lg and CD8gp39), inhibitors, such as nuclear translocation inhibitors, of NF-kappa B function, such as deoxyspergualin (DSG), cholesterol biosynthesis inhibitors such as HM:G CoA reductase inhibitors (lovastatin and simvastatin), non-steroidal antiinflammatory drugs (NSAIDs) such as ibuprofen and cyclooxygenase inhibitors such as rofecoxib, steroids such as prednisone or dexamethasone, gold compounds, antiproliferative agents such as methotrexate, FK506 (tacrolimus, Prograf), mycophenolate mofetil, cytotoxic drugs such as azathioprine and cyclophosphamide, TNF-a inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one having ordinary skill in the art.

EXAMPLES

The following examples are provided to further illustrate the present invention but, of course, should not be construed as in any way limiting its scope.

All experiments were performed under anhydrous conditions (i.e. dry solvents) in an atmosphere of argon, except where stated, using oven-dried apparatus and employing standard techniques in handling air-sensitive materials. Aqueous solutions of sodium bicarbonate ($NaHCO_3$) and sodium chloride (brine) were saturated.

Analytical thin layer chromatography (TLC) was carried out on Merck Kiesel gel 60 F254 plates with visualization by ultraviolet and/or anisaldehyde, potassium permanganate or phosphomolybdic acid dips.

NMR spectra: $^1$H Nuclear magnetic resonance spectra were recorded at 400 MHz. Data are presented as follows: chemical shift, multiplicity (s=singlet, d=doublet, t=triplet, q=quartet, qn=quintet, dd=doublet of doublets, m=multiplet, bs=broad singlet), coupling constant (J/Hz) and integration. Coupling constants were taken and calculated directly from the spectra and are uncorrected.

LC/mass spectra: Electrospray (ES+) ionization was used. The protonated parent ion (M+H) or parent sodium ion (M+Na) or fragment of highest mass is quoted. Analytical gradient consisted of 10% ACN in water ramping up to 100% ACN over 5 minutes unless otherwise stated.

Example 1

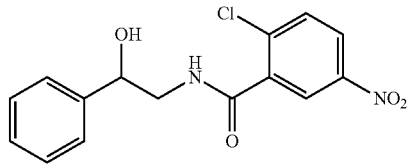 [SMILES: O=C(NCC(O)c1ccccc1)c1cc([N+](=O)[O-])ccc1Cl]

A solution of 2-chloro-5-nitrobenzoyl chloride (11.70 g, 53.2 mmol) in DCM (66.0 mL) was added dropwise to a solution of 2-amino-1-phenylethanol (7.30 g, 53.2 mmol) in DCM (200 mL) containing triethylamine (7.40 mL, 53.2 mmol) at 0° C. The reaction mixture was stirred at 0° C. for 1 hr. The reaction was quenched with saturated $NaHCO_3$ solution and the organic layer was separated. The organic layer was washed with brine, dried over anhydrous $Na_2SO_4$ and then concentrated under reduced pressure. The crude residue was recrystallized from hexane/EtOAc to yield the desired compound (10.76 g, % yield) as a white solid. $^1$H NMR (400 MHz, $CDCl_3$): δ 8.46 (d, J=2.8 Hz, 1H), 8.21 (dd, J=2.8, 8.8 Hz, 1H), 7.59 (d, J=8.8 Hz, 1H), 7.44-7.31 (m, 5H), 6.65 (br s, 1H), 5.01 (m, 1H), 3.97 (m, 1H), 3.56 (m 1H), 2.68 (d, J=2.8 Hz, 1H). MS (ESI): Calcd. for $C_{15}H_{13}ClN_2O_4Na$ 343. found 343 (M+Na)$^+$.

Example 2

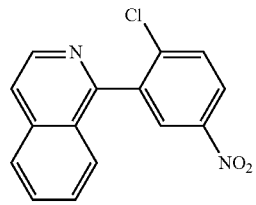 [SMILES: O=[N+]([O-])c1ccc(Cl)c(-c2nccc3ccccc23)c1]

A mixture of 2-chloro-N-(2-hydroxy-2-phenylethyl)-5-nitrobenzamide (3.40 g, 10.60 mmol) with $POCl_3$ (11.86 mL, 127.2 mmol) and $P_2O_5$ (17.0 g, 119.8 mmol) in toluene/xylene (265.0 mL, 1:1) was refluxed for 2 d. The reaction mixture was cooled down and then poured into ice-water followed by neutralization with 10% NaOH solution. The mixture was extracted with EtOAc and the combined extracts were washed with brine, dried over anhydrous $Na_2SO_4$ and then concentrated under reduced pressure. The residue was purified by flash column chromatography on silica gel (hexane/EtOAc 95:5 to 90:10) followed by recrystallization from hexane/EtOAc to yield the desired compound (850 mg, 28%) as yellow crystals. $^1$H NMR (400 MHz, CDCl$_3$): δ 8.66 (d, J=5.6 Hz, 1H), 8.38 (d, J=2.8 Hz, 1H), 8.32 (dd, J=2.8, 8.8 Hz, 1H), 7.95 (m, 1H), 7.80 (d, J=5.6 Hz, 1H), 7.77-7.73 (m, 2H), 7.57 (m, 2H). MS (ESI): Calcd. for C$_{15}$H$_{10}$ClN$_2$O$_2$: 285. found 285 (M+H)$^+$.

Example 3

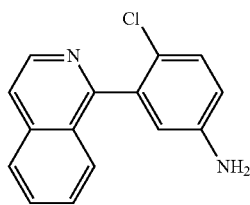 [SMILES: Nc1ccc(Cl)c(-c2nccc3ccccc23)c1]

A mixture of 21-(2-chloro-5-nitrophenyl)isoquinoline (785 mg, 2.76 mmol) and tin (II) chloride dehydrate (2.93 g, 12.97 mmol) in ethanol (36.8 mL) was heated at 70° C. for 1.5 hr. The reaction mixture was cooled down and then poured into ice-water followed by neutralization with saturated NaHCO$_3$ solution. The mixture was filtered through a pad of celite and washed with EtOAc. The filtrate was extracted with EtOAc and the combined extracts were washed with brine, dried over anhydrous Na$_2$SO$_4$ and then concentrated under reduced pressure to yield the desired compound (650 mg, 92%) as yellow solid. $^1$H NMR (400 MHz, CDCl$_3$): δ 8.61 (d, J=5.6 Hz, 1H), 7.88 (d, J=8.0 Hz, 1H), 7.75-7.67 (m, 3H), 7.53 (m, 1H), 7.29 (dd, J=0.8, 8.0 Hz, 1H), 6.76 (m, 2H), 3.76 (br s, 2H). MS (ESI): Calcd. for C$_{15}$H$_{12}$ClN$_2$: 255. found 255 (M+H)$^+$.

Example 4

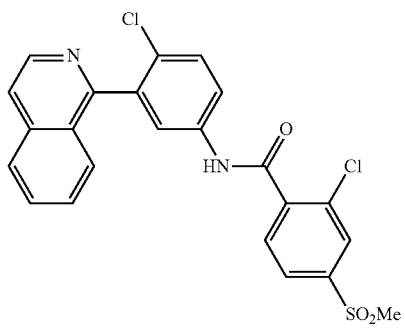 [SMILES: CS(=O)(=O)c1ccc(C(=O)Nc2ccc(Cl)c(-c3nccc4ccccc34)c2)c(Cl)c1]

A solution of 2-chloro-4-(methylsulfonyl)benzoyl chloride (298 mg, 1.18 mmol) in DCM (3.1 mL) was added dropwise to a solution of 4-chloro-3-(isoquinolin-1-yl)aniline (100 mg, 0.393 mmol) in DCM (10.0 mL) containing pyridine (127 µL, 1.57 mmol) at 0° C. The reaction mixture was allowed to warm to room temperature and stirred overnight. EtOAc was added and the mixture was washed with saturated NaHCO$_3$ solution and brine, respectively. The organic phase was dried over anhydrous Na$_2$SO$_4$ and then concentrated under reduced pressure. The residue was purified by flash column chromatography on silica gel (hexane/EtOAc 1:1 to 2:3) to yield the desired compound (86 mg, 46% yield) as a to white solid. $^1$H NMR (400 MHz, DMSO-d$_6$): δ 10.98 (s, 1H), 8.61 (d, J=5.6 Hz, 1H), 8.12 (dd, J=0.4, 1.6 Hz, 1H), 8.09 (d, J=8.0 Hz, 1H), 8.00 (dd, J=1.6, 8.0 Hz, 1H), 7.92 (m, 3H), 7.83 (m, 2H), 7.66 (m, 2H), 7.58 (m, 1H), 3.33 (s, 3H). MS (ESI): Calcd. for C$_{23}$H$_{17}$Cl$_2$N$_2$O$_3$S: 471. found 471 (M+H)$^+$.

Example 5

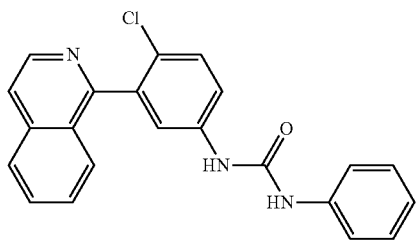 [SMILES: O=C(Nc1ccccc1)Nc1ccc(Cl)c(-c2nccc3ccccc23)c1]

Phenyl isocyanate (29 µL, 0.260 mmol) was added dropwise to a solution of 4-chloro-3-(isoquinolin-1-yl)aniline (60 mg, 0.236 mmol) in DCM (7.87 mL) at room temperature. The reaction mixture was stirred overnight. The solvent was removed under reduced pressure and the residue was purified by flash column chromatography on silica gel (hexane/EtOAc 7:3 to 1:1) to yield the desired compound (36 mg, 41% yield) as a pale yellow solid. $^1$H NMR (400 MHz, DMSO-d$_6$): δ 8.94 (s, 1H), 8.75 (s, 1H), 8.60 (d, J=5.6 Hz, 1H), 8.08 (d, J=8.4 Hz, 1H), 7.93 (dd, J=0.6, 5.8 Hz, 1H), 7.81 (m, 1H), 7.67 (d, J=2.0 Hz, 1H), 7.64 (m 1H), 7.56 (m, 3H), 7.43 (m, 2H), 7.26 (m, 2H), 6.96 (m, 1H). MS (ESI): Calcd. for C$_{22}$H$_{17}$ClN$_3$O: 374. found 374 (M+H)$^+$.

Example 6

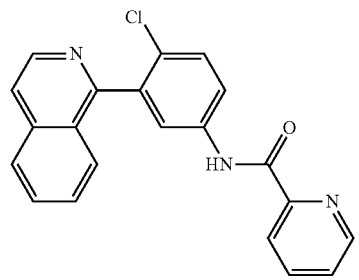 [SMILES: O=C(Nc1ccc(Cl)c(-c2nccc3ccccc23)c1)c1ccccn1]

Picolinoyl chloride HCl salt (63 mg, 0.354 mmol) was added to a solution of 4-chloro-3-(isoquinolin-1-yl)aniline (45 mg, 0.177 mmol) in DCM (5.90 mL) containing triethylamine (99 μL, 0.708 mmol) at 0° C. The reaction mixture was allowed to warm to room temperature and stirred for 3 h. EtOAc was added and the mixture was washed with saturated NaHCO$_3$ solution and brine, respectively. The organic phase was dried over anhydrous Na$_2$SO$_4$ and then concentrated under reduced pressure. The residue was purified by flash column chromatography on silica gel (hexane/EtOAc 7:3 to 1:1) to yield the desired compound (25 mg, 39% yield) as a white solid. $^1$H NMR (400 MHz, DMSO-d$_6$): δ 10.94 (s, 1H), 8.74 (m, 1H), 8.62 (d, J=5.6 Hz, 1H), 8.16-8.04 (m, 5H), 7.95 (dd, J=0.8, 5.6 Hz, 1H), 7.82 (m, 1H), 7.70-7.58 (m, 4H). MS (ESI): Calcd. for C$_{21}$H$_{15}$ClN$_3$O: 360. found 360 (M+H)$^+$.

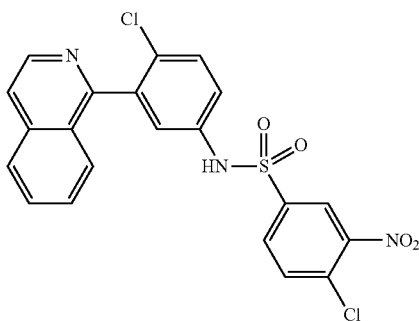 [SMILES: O=[N+]([O-])c1cc(S(=O)(=O)Nc2ccc(Cl)c(-c3nccc4ccccc34)c2)ccc1Cl]

Example 7

A solution of 4-chloro-3-nitrobenzene-1-sulfonyl chloride (50 mg, 0.196 mmol) in DCM (4.0 mL) was added dropwise to a solution of 4-chloro-3-(isoquinolin-1-yl)aniline (50 mg, 0.196 mmol) in DCM (9.8 mL) at 0° C. The reaction mixture was stirred at 0° C. for 1 h. The reaction was quenched with saturated NaHCO$_3$ solution and the mixture was extracted with EtOAc. The combined extracts were washed with brine, dried over anhydrous Na$_2$SO$_4$ and then concentrated under reduced pressure. The residue was treated with DCM to yield the desired compound (69 mg, 74% yield) as a light yellow solid. $^1$H NMR (400 MHz, DMSO-d$_6$): δ 11.08 (s, 1H), 8.64 (d, J=6.0 Hz, 1H), 8.44 (t, J=1.2 Hz, 1H), 8.17 (m, 2H), 8.02 (d, J=1.2 Hz, 2H), 7.95 (m, 1H), 7.69 (m, 1H), 7.65 (d, J=8.8 Hz, 1H), 7.41 (m, 2H), 7.27 (d, J=2.8 Hz, 1H). MS (ESI): Calcd. for C$_{21}$H$_{14}$Cl$_2$N$_3$O$_4$S: 474. found 474 (M+H)$^+$.

Example 8

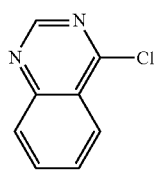 [SMILES: Clc1ncnc2ccccc12]

A mixture of 4-hydroxyquinazoline (1.20 g, 8.21 mmol) in SOCl$_2$ (27.4 mL) containing DMF (2 drops) was refluxed for 2 h. SOCl$_2$ was removed under reduced pressure and the residue was dissolved in DCM. The solution was washed with saturated NaHCO$_3$ solution and brine, respectively, dried over anhydrous Na$_2$SO$_4$ and then concentrated under reduced pressure to yield the desired compound (1.19 g, 88% yield) as a white solid. $^1$H NMR (400 MHz, CDCl$_3$): δ 9.06 (s, 1H), 8.29 (m, 1H), 8.09 (m, 1H), 7.98 (m, 1H), 7.75 (m, 1H). MS (ESI): Calcd. for C$_8$H$_6$ClN$_2$: 165. found 165 (M+H)$^+$.

Example 9

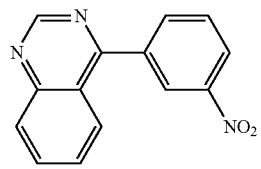 [SMILES: O=[N+]([O-])c1cccc(-c2ncnc3ccccc23)c1]

A mixture of 4-chloroquinazoline (658 mg, 4.0 mmol), 3-nitrophenylboronic acid (935 mg, 5.6 mmol), Pd(PPh$_3$)$_4$ (231 mg, 0.2 mmol) and 2M K$_2$CO$_3$ solution (4.0 mL, 8.0 mmol) in toluene (30.0 mL) and ethanol (2.0 mL) was refluxed for 6 h. The reaction mixture was cooled down and water was added. The resulting mixture was extracted with EtOAc and the combined extracts were washed with brine, dried over anhydrous Na$_2$SO$_4$ and then concentrated under reduced pressure. The residue was purified by flash column chromatography on silica gel (hexane/EtOAc 10:1 to 1:1) to yield the desired compound (771 mg, 77% yield) as a pale yellow solid. $^1$H NMR (400 MHz, CDCl$_3$): δ 9.43 (s, 1H), 8.69 (m, 1H), 8.45 (ddd, J=1.0, 2.4, 8.4 Hz, 1H), 8.17 (m, 2H), 8.05 (ddd, J=0.8, 1.2, 2.0 Hz, 1H), 7.99 (m, 1H), 7.80 (m, 1H), 7.69 (m, 1H). MS (ESI): Calcd. for C$_{14}$H$_{10}$N$_3$O$_2$: 252. found 252 (M+H)$^+$.

Example 10

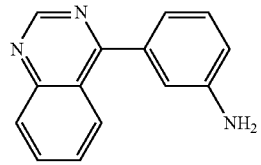

A mixture of 4-(3-nitrophenyl)quinazoline (700 mg, 2.79 mmol) and tin (II) chloride dehydrate (2.83 g, 12.56 mmol) in ethanol (37.2 mL) was heated at 70° C. for 1.5 hr. The reaction mixture was cooled down and then poured into ice-water followed by neutralization with saturated NaHCO$_3$ solution. The mixture was filtered through a pad of celite and washed with EtOAc. The filtrate was extracted with EtOAc and the combined extracts were washed with brine, dried over anhydrous Na$_2$SO$_4$ and then concentrated under reduced pressure to yield the desired compound (600 mg, 97%) as a yellow solid. $^1$H NMR (400 MHz, CDCl$_3$): δ 9.36 (s, 1H), 8.19 (m, 1H), 8.10 (d, J=8.4 Hz, 1H), 7.91 (m, 1H), 7.60 (m, 1H), 7.34 (t, J=8.0 Hz, 1H), 7.12 (m, 1H), 7.09 (t, J=2.0 Hz, 1H), 6.88 (ddd, J=1.2, 2.4, 8.0 Hz, 1H), 3.85 (s, 2H). MS (ESI): Calcd. for C$_{14}$H$_{12}$N$_3$: 222. found 222 (M+H)$^+$.

Example 11

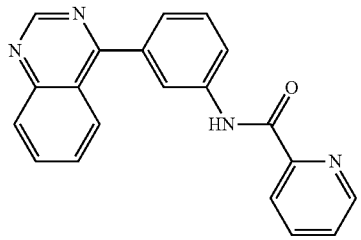 [SMILES: O=C(Nc1cccc(-c2ncnc3ccccc23)c1)c1ccccn1]

Picolinoyl chloride HCl salt (60 mg, 0.339 mmol) was added to a solution of 3-(quinazolin-4-yl)aniline (50 mg, 0.226 mmol) in DCM (7.53 mL) containing triethylamine (95 μL, 0.678 mmol) at 0° C. The reaction mixture was allowed to warm to room temperature and stirred for 30 min. EtOAc was added and the mixture was washed with saturated NaHCO$_3$ solution and brine, respectively The organic phase was dried over anhydrous Na$_2$SO$_4$ and then concentrated under reduced pressure. The residue was purified by flash column chromatography on silica gel (hexane/EtOAc 1:1) to yield the desired compound (39 mg, 53% yield) as a light pink solid. $^1$H NMR (400 MHz, DMSO-d$_6$): δ 10.94 (s, 1H), 9.38 (s, 1H), 8.76 (m, 1H), 8.43 (t, J=1.8 Hz, 1H), 8.24-8.05 (m, 6H), 7.79 (m, 1H), 7.70 (ddd, J=1.6, 4.8, 7.6 Hz, 1H), 7.63 (t, J=8.0 Hz, 1H), 7.57 (dt, J=1.6, 7.6 Hz, 1H). MS (ESI): Calcd. for C$_{20}$H$_{16}$N$_4$O: 327. found 327 (M+H)$^+$.

Example 12

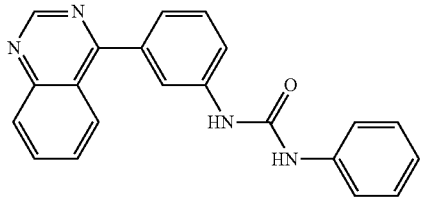 [SMILES: O=C(Nc1ccccc1)Nc1cccc(-c2ncnc3ccccc23)c1]

Phenyl isocyanate (37 μL, 0.339 mmol) was added dropwise to a solution of 3-(quinazolin-4-yl)aniline (50 mg, 0.226 mmol) in DCM (7.53 mL) at room temperature. The reaction mixture was stirred for 4 h. The solvent was removed under reduced pressure and the residue was purified by flash column chromatography on silica gel (DCM/MeOH 99:1 to 95:5) to yield the desired compound (27 mg, 35% yield) as a white solid. $^1$H NMR (400 MHz, DMSO-d$_6$): δ 9.36 (s, 1H), 8.95 (s, 1H), 8.74 (s, 1H), 8.18 (d, J=8.0 Hz, 1H), 8.08 (m, 2H), 7.99 (s, 1H), 7.77 (m, 1H), 7.64 (m, 1H), 7.54 (t, J=8.0 Hz, 1H), 7.46 (d, J=7.6 Hz, 2H), 7.39 (d, J=7.6 Hz, 1H), 7.28 (t, J=8.0 Hz, 2H), 6.97 (t, J=7.6 Hz, 1H). MS (ESI): Calcd. for C$_{21}$H$_{17}$N$_4$O: 341. found 341 (M+H)$^+$.

Example 13

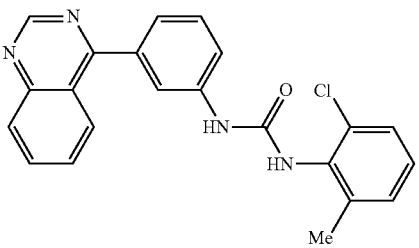 [SMILES: Cc1cccc(Cl)c1NC(=O)Nc1cccc(-c2ncnc3ccccc23)c1]

1-Chloro-2-isocyanato-3-methylbenzene (78 μL, 0.565 mmol) was added dropwise to a solution of 3-(quinazolin-4-yl)aniline (50 mg, 0.226 mmol) in DCM (7.53 mL) at room temperature. The reaction mixture was stirred for 6 h. The precipitate was collected by filtration under reduced pressure and washed with DCM and hexane to yield the desired compound (57 mg, 65% yield) as a pale yellow solid. $^1$H NMR (400 MHz, DMSO-d$_6$): δ 9.34 (s, 1H), 9.20 (s, 1H), 8.16 (m, 1H), 8.10 (dd, J=0.8, 8.4 Hz, 1H), 8.05 (m, 2H), 7.98 (t, J=1.8 Hz, 1H), 7.76 (m, 1H), 7.66 (m, 1H), 7.52 (t, J=8.0 Hz, 1H), 7.36 (m, 2H), 7.24 (m, 1H), 7.19 (q, J=7.6 Hz, 1H), 2.27 (s, 3H). MS (ESI): Calcd. for C$_{22}$H$_{18}$ClN$_4$O: 389. found 389 (M+H)$^+$.

Example 14

Hedgehog Signaling Inhibition Assays

Hh-Dependent C3H10T1/2 Differentiation Assay:

C3H10T1/2 cells are multipotent mesenchymal progenitor cells that have the potential to differentiate into osteoblasts upon stimulation of the Hh pathway. Osteoblasts produce substantial alkaline phosphatase (AP) that can easily be measured with an enzymatic assay. Briefly, mouse embryonic mesoderm fibroblasts C3H10T1/2 cells (obtained from ATCC Cat# CCL-226) were cultured in Basal MEM Media (Gibco/Invitrogen) supplemented with 10% heat inactivated FBS (Hyclone), 50 units/ml penicillin, 50 μg/ml streptomycin (Gibco/Invitrogen) and 2 mM Glutamine (Gibco/Invitrogen) at 37° C. with 5% CO2 in air atmosphere. Cells were dissociated with 0.05% trypsin and 0.02% EDTA in PBS for passage and plating. C3H10T1/2 cells were plated in 96 wells with a density of 8×103 cells/well. Cells were grown to confluence (72 h). Media containing 5 μM of 20(S)-hydroxycholesterol and 5 μM of 22(S)-hydroxycholesterol and/or compound was added at the start of the assay and left for 72 h. Media was aspirated and cells were washed once in PBS. Alkaline phosphatase was measured by adding 100 μL Tropix CDP-Star with Emerald II (0.4 mM Cat # MS100RY) to the well and the plate was incubated at room temperature in the dark for one hour. The plates were read on an Envision plate reader at 405 nm. The percent inhibition with respect to compound concentration was plotted using Prism graphing software on a semi-log plot and EC50s determined by non-linear regression analysis with a four-parameter logistic equation.

What is claimed is:

1. A compound as shown in Formula (I)

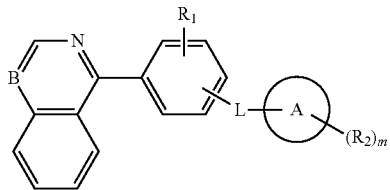

or a pharmaceutically acceptable salt thereof, wherein:

B is N or CH;

$R_1$ represents hydrogen, halogen, hydroxyl, amino, nitro, cyano, alkyl, alkenyl, alkoxy, alkoxycarbonyl, carbamoyl, alkylthio, sulfonyl, sulfinyl, cycloalkyl or a heterocycle;

L is oxygen, $NR_3$, $NR_3CO$, $NR_3SO$, $SO_2NR_3$; $NR_3CONH$, $NR_3CSNH$, $CONR_3$, $CSNR_3$, $NR_3$ $CHR_4$, $NR_3PO$ or $NR_3PO(OH)$;

Ring A is aryl or heteroaryl;

$R_2$ represents hydrogen, hydroxyl, halogen, amino, nitro, cyano, acyl, alkyl, alkenyl, alkynyl, alkylthio, sulfonyl, sulfinyl, alkoxy, alkoxycarbonyl, carbamoyl, acylamine, sulfamoyl or sulfonamide;

or $R_2$ is aryl, heterocycle or heteroaryl that is optionally substituted with hydroxyl, halogen, amino, nitro, cyano, acyl, alkyl, alkanoyl, sulfonyl, sulfinyl, alkoxy, carbamoyl, acylamine, sulfamoyl and sulfonamide;

$R_3$ and $R_4$ are independently selected from hydrogen or an optionally substituted C1-4 alkyl group;

m is 0-4.

2. A compound as shown in Formula (Ia)

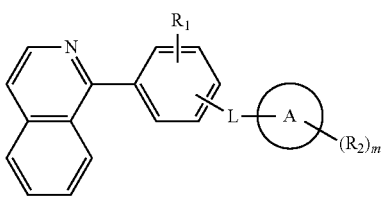

or a pharmaceutically acceptable salt thereof, wherein:

A, $R_1$, $R_2$, L, and m are as defined in claim 1.

3. A compound as shown in Formula (Ib)

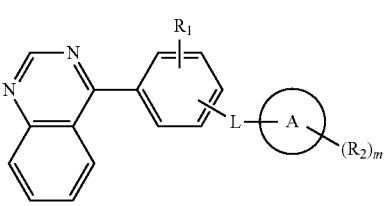

or a pharmaceutically acceptable salt thereof, wherein:

A, $R_1$, $R_2$, L, and m are as defined in claim 1.

4. A compound as shown in Formula (A):

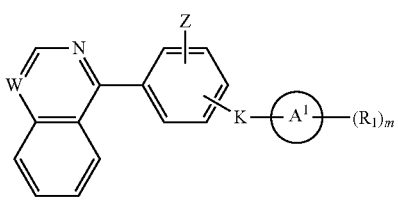

or a pharmaceutically acceptable salt thereof, wherein:

K is selected from $NR_3C(O)$, $C(O)NR_3$, $SO_2NR_3$, and $NR_4C(O)NR_5$;

$A^1$ is selected from aryl, heterocyclyl, and heteroaryl;

$R_1$ is selected from H, halo, nitro, $-OR_4$, $C_1$-$C_6$ alkyl, $C_1$-$C_6$ alkylsulfonyl, and $C_1$-$C_6$ haloalkyl;

m=0-4;

$R_3$, $R_4$, and $R_5$ are each independently selected from H and $C_1$-$C_6$ alkyl;

W is selected from CH and N;

Z is selected from H, halo, and $C_1$-$C_6$ alkyl, $C_1$-$C_6$ alkylthio, $-NR_4R_5$, $-OR_4$, and cyano.

5. A compound or pharmaceutically acceptable salt of claim 4, wherein:

K is selected from $NR_3C(O)$, $C(O)NR_3$, $SO_2NR_3$, and $NR_4C(O)NR_5$;

$A^1$ is selected from phenyl and pyridyl;

$R^1$ is selected from H, halo, nitro, $C_1$-$C_6$ alkylsulfonyl, and $C_1$-$C_6$ alkyl;

m=0-4;

$R_3$, $R_4$ and $R_5$ are each independently selected from H and $C_1$-$C_6$ alkyl;

W is selected from CH and N;

Z is selected from H, halo, and $C_1$-$C_6$ alkyl.

6. A compound as shown in Formula (B):

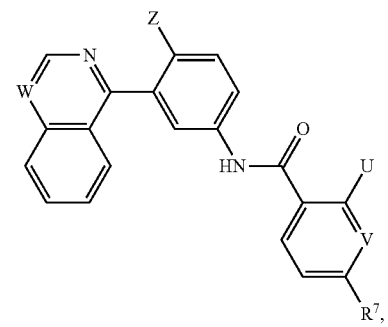

or a pharmaceutically acceptable salt thereof, wherein:

$R_3$, $R_4$, and $R_5$ are each independently selected from H and $C_1$-$C_6$ alkyl;

$R_7$ is selected from heterocyclyl, haloalkyl, $NR_3C(O)R_4$, $NR_3C(O)NR_4R_5$, $NR_3C(O)[C(R_3)(R_4)]_nO[C(O)]pR_4$, $(CH_2)_nSO_2R_3$, $NR_3SO_2R_4$, $NR_3C(O)$-Q-$R_4$, and $N(OR_3)C(O)R_4$;

n is 1-2;

p is 0 or 1;

Q is heterocyclyl;

U is selected from H, halo, $C_1$-$C_6$ alkyl, $C_1$-$C_6$ alkylthio, $-NR_4R_5$, $-OR_4$, and cyano;

V is selected from CH and N;

W is selected from CH and N;

Z is selected from H, halo, and $C_1$-$C_6$ alkyl.

7. A compound as shown in Formula (C):

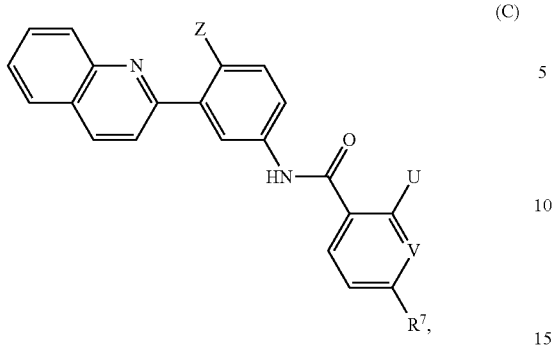

or a pharmaceutically acceptable salt thereof, wherein:
$R_3$, $R_4$, and $R_5$ are each independently selected from H and $C_1$-$C_6$ alkyl;
$R_7$ is selected from heterocyclyl, haloalkyl, $NR_3C(O)R_4$, $NR_3C(O)NR_4R_5$, $NR_3C(O)[C(R_3)(R_4)]_nO[C(O)]pR_4$, $(CH_2)_nSO_2R_3$, $NR_3SO_2R_4$, $NR_3C(O)$-Q-$R_4$, and $N(OR_3)C(O)R_4$;
n is 1-2;
p is 0 or 1;
Q is heterocyclyl;
U is selected from H, halo, $C_1$-$C_6$ alkyl, $C_1$-$C_6$ alkylthio, —$NR_4R_5$, —$OR_4$, and cyano;
V is selected from CH and N;
Z is selected from H, halo, and $C_1$-$C_6$ alkyl.

8. A compound having the structure shown in Formula (i):

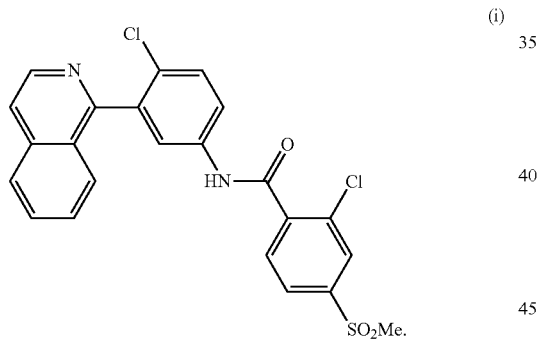

9. The compound of claim 6, wherein the compound is as shown in Formula (ii):

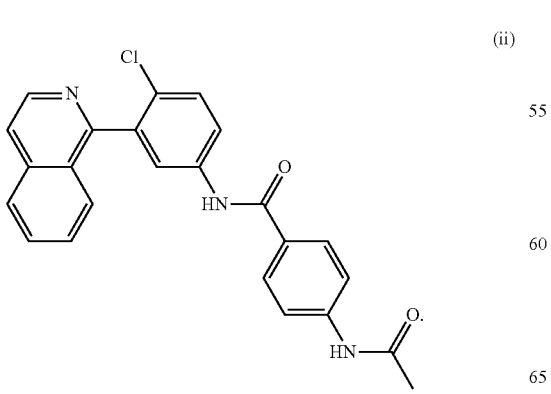

10. The compound of claim 6, wherein the compound is as shown in Formula (iii):

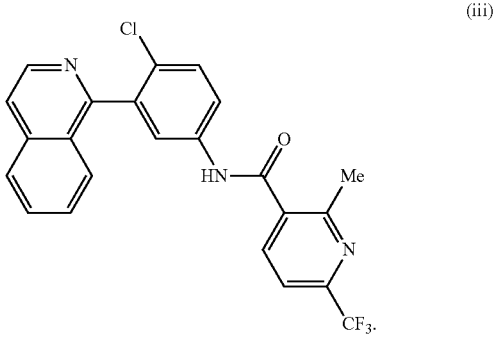 [SMILES: Cc1nc(C(F)(F)F)ccc1C(=O)Nc1ccc(Cl)c(-c2nccc3ccccc23)c1]

11. The compound of claim 6, wherein the compound is as shown in Formula (iv):

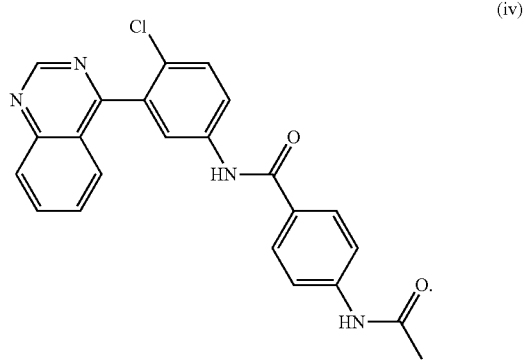 [SMILES: CC(=O)Nc1ccc(C(=O)Nc2ccc(Cl)c(-c3ncnc4ccccc34)c2)cc1]

12. The compound of claim 6, wherein the compound is as shown in Formula (v):

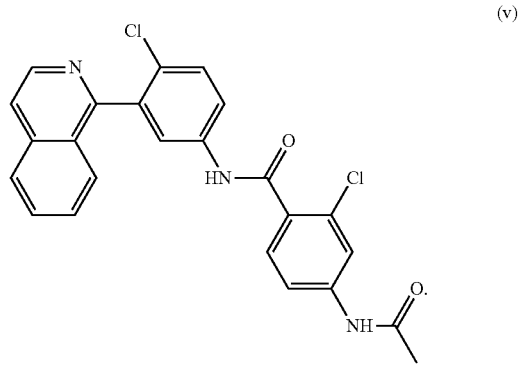 [SMILES: CC(=O)Nc1ccc(C(=O)Nc2ccc(Cl)c(-c3nccc4ccccc34)c2)c(Cl)c1]

13. The compound of claim 6, wherein the compound is as shown in Formula (vi):

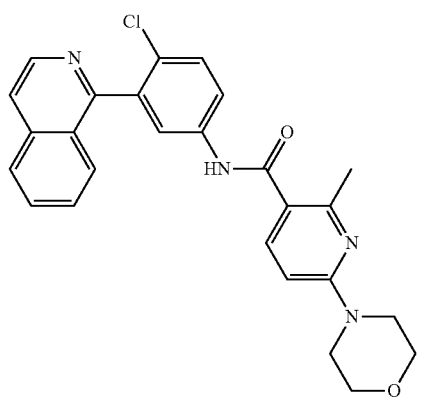
(vi)
14. The compound of claim 6, wherein the compound is as shown in Formula (vii):
(vii)
15. The compound of claim 6, wherein the compound is as shown in Formula (viii):
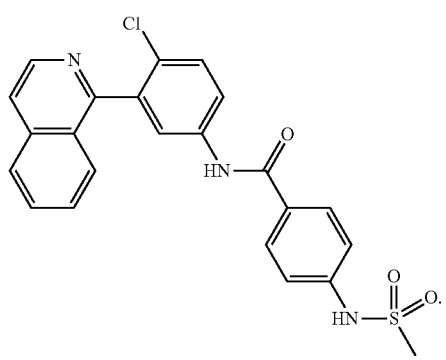
(viii)
16. The compound of claim 6, wherein the compound is as shown in Formula (ix):
(ix)
17. The compound of claim 6, wherein the compound is as shown in Formula (x):
(x)
18. The compound of claim 6, wherein the compound is as shown in Formula (xi):
(xi)

19. The compound of claim 6, wherein the compound is as shown in Formula (xii):

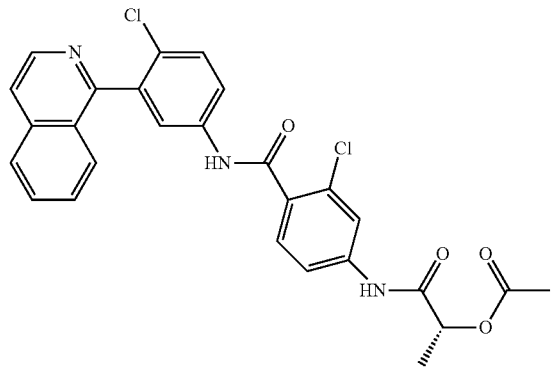

(xii)

20. The compound of claim 6, wherein the compound is as shown in Formula (xiii):

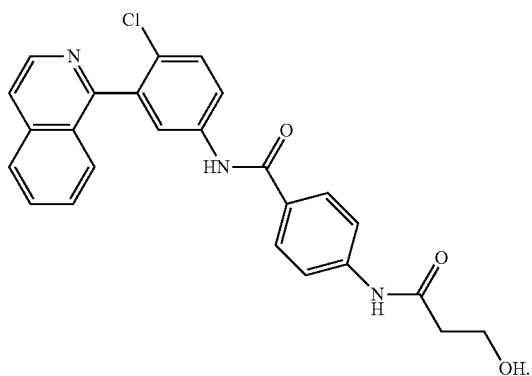

(xiii)

21. The compound of claim 6, wherein the compound is as shown in Formula (xiv):

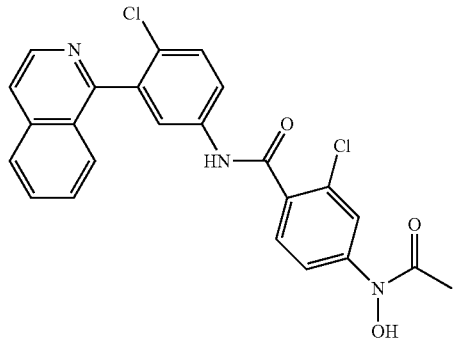

(xiv)

22. The compound of claim 7, wherein the compound is as shown in Formula (xv):

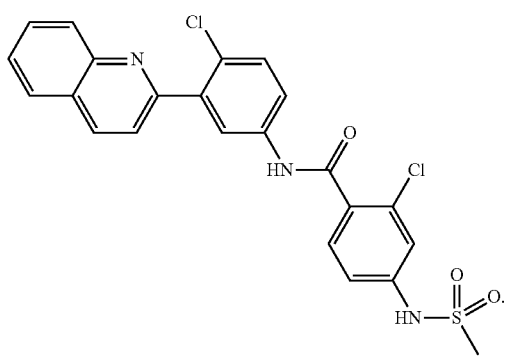

(xv)

23. A process for making a compound of claim 1 or its pharmaceutically acceptable salts, hydrates, solvates, crystal forms, salts and individual diastereomers thereof.

24. A pharmaceutical composition comprising at least one compound of claim 1 or its pharmaceutically acceptable salts, hydrates, solvates, crystal forms, salts and individual diastereomers thereof, and a pharmaceutically acceptable carrier.

* * * * *